US008282937B2

(12) United States Patent
Maassab et al.

(10) Patent No.: US 8,282,937 B2
(45) Date of Patent: Oct. 9, 2012

(54) COLD-ADAPTED (CA) REASSORTANT INFLUENZA VIRUS

(75) Inventors: Hunein Maassab, Ann Arbor, MI (US); Martha Louise Herlocher, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 729 days.

(21) Appl. No.: 11/690,498

(22) Filed: Mar. 23, 2007

(65) Prior Publication Data

US 2007/0172929 A1 Jul. 26, 2007

Related U.S. Application Data

(60) Division of application No. 08/573,569, filed on Dec. 14, 1995, now Pat. No. 7,344,722, which is a continuation of application No. 08/082,846, filed on Jun. 29, 1993, now abandoned.

(51) Int. Cl.
*A61K 39/145* (2006.01)
*C12N 7/04* (2006.01)

(52) U.S. Cl. .................................... 424/206.1; 435/236

(58) Field of Classification Search ........................ None
See application file for complete search history.

(56) References Cited

OTHER PUBLICATIONS

Maassab, H., et al., 1982, Evaluation of a cold-recombinant influenza virus vaccine in ferrets, J. Infect. Dis. 146(6):780-790.*
Cox, N., et al., 1988, Identification of sequence changes in the cold-adapted, live attenuated influenza vaccine strain, A/Ann Arbor/6/60, Virol. 167:554-567.*

* cited by examiner

*Primary Examiner* — Jeffrey S. Parkin
(74) *Attorney, Agent, or Firm* — Marshall, Gerstein & Borun LLP

(57) ABSTRACT

The cold-adapted master strain A/Ann Arbor/6/60 7PI (H2N2) and progenitor wild type E2(3) viral strains have been deposited and their genomic sequences identified. Seven nucleotide differences were found between the sequences identified herein and the previously published sequences for cold-adapted A/Ann Arbor/6/60 genes. The cold-adapted live influenza virus of the present invention can be reasserted with a variety of epidemic wild type influenza viruses and used to produce vaccines to prophylactically and therapeutically treat influenza.

5 Claims, 2 Drawing Sheets

COLD-ADAPTED (CA) REASSORTANT INFLUENZA VIRUS

This application is a divisional of patent application Ser. No. 08/573,569 filed Dec. 14, 1995, allowed, which is a continuation of application Ser. No. 08/082,846 filed Jun. 29, 1993, abandoned, each of which are incorporated by reference.

Work on this invention has been supported since 1976 by the contract office of the National Institute of Allergy and Infectious Diseases with Contract Nos. 1-AI-72521, 1-AI-52564, and 1-AI-05053; by Public Health Service Research Grant AI-20591 from the National Institute of Allergy and Infectious Diseases; by Cancer Center Support (CORE) Grant CA-21765; by American Lebanese Syrian Associated Charities (ALSAC) of St. Jude Children's Research Hospital; and Pittsburgh Supercomputing Centers through the National Institutes of Health Division of Research Resources cooperative agreement U41 RR04154. The United States Government has certain rights in the invention.

BIOLOGICAL DEPOSITS

The following viral strains have been deposited under the Budapest Treaty with the American Type Culture Collection (ATCC), 12301 Parklawn Drive, Rockville, Md. 20852:

| VIRUS | ACCESSION NO. | DATE OF DEPOSIT |
|---|---|---|
| Wild type A/Ann Arbor/6/60 (H2N2) egg passage 2(3) | | Jun. 10, 1993 |
| Cold-adapted "Master Strain" A/Ann Arbor/6/60 7PI (H2N2) | | Jun. 10, 1993 |

FIELD OF THE INVENTION

The present invention relates generally to cold-adapted influenza virus and, more particularly, to a cold-adapted influenza virus vaccine and methods of preventing and treating influenza by employing the vaccine.

BACKGROUND OF THE INVENTION

The tremendous impact of influenza virus infections on the public health is widely recognized. Control of influenza has relied primarily on the use of inactivated influenza vaccines. More current approaches, however, have moved towards the use of live attenuated vaccine. Kilbourne, E. D. "Influenza" (Plenum Publishing Corp. New York), p. 291-332 (1987). The most promising efforts in the development of an effective live vaccine have centered on adapting the virus to grow at sub-optimal temperatures. Maassab, H. F., et al., *Vaccine* 3:355-369 (1985). Using this approach, cold-adapted attenuated influenza viruses have been developed in both the former Soviet Union and the United States. Alexandrova, G. I., et al., *Rev. Roum. Inframicrobil.* 2:179-189 (1965); Maassab, H. F. *Nature* (London) 213: 612-614 (1967).

In particular, cold adaptation (ca) has permitted the A/Ann Arbor/6/60 (H2N2) (A/AA/6/60) virus of the present invention to grow as well at 25° C. as it does at 33° C. Maassab, H. F. *Nature* (London) 213:612-614 (1967); Maassab, H. F. "Biology of Large RNA Viruses" (Academic Press, New York), p. 542-565 (1970). The ca A/AA/6/60 virus is also temperature-sensitive (ts), a property that impedes replication at higher temperatures in the lungs and thus is highly desirable for live vaccines. Maassab, H. F., "Biology of Large RNA Viruses" (Academic Press, New York), p. 542-565 (1970); Mulder, J., et al., "Influenza" (Wolters-Noordhoff, Amsterdam), 1-6:78-80 (1972). Single-gene studies of this cold-adapted virus in a background of A/Korea/1/82 (H3N2) have identified the genes responsible for the ca and ts phenotypes and for attenuation in that gene constellation. Snyder, M. H., et al., *J. Virol.* 62(2):488-495 (1988).

Live attenuated vaccines are produced by reassorting the six internal genes of the cold-adapted A/Ann Arbor/6/60 influenza virus with the two surface genes of the currently circulating wild type (wt) virus, thereby producing a reassortant strain. Maassab, H. F. "Negative Strand Viruses" (Academic Press, New York), p. 755-763 (1975); Davenport, F. M., et al., *J. Infect. Dis.* 136:17-25 (1977). Vaccines prepared from ca A/AA/6/60 have proven both non-reactogenic and non-transmissible in preliminary field trials at six different medical centers involving over 20,000 people. Couch, R. B., et al., "Options for the Control of Influenza" (Alan R. Liss, New York), p. 223-241 (1986); Wright, P. F., et al., "Options for the Control of Influenza" (Alan R. Liss, New York), p. 243-253 (1986). These vaccines also provide higher IgA levels than the killed vaccines and afford longer-lasting protection in children. Murphy, B. R., et al., *Infect. Immun.* 36(3): 1102-1108 (1982); Johnson, P. R., et al., *J. Infect. Dis.* 154 (1):121-127 (1986). Currently, the ca A/AA/6/60 7PI (plaque-purified seven times) master strain preparation is under development for use as a live vaccine in children and other live virus vaccines are being developed using the live ca influenza vaccine as a model.

Cold-adapted reassortant vaccines have thus been shown to have the proper level of attenuation, immunogenicity, and non-transmissibility combined with proven genetic stability and are produced in acceptable tissue culture substrates. In general, live cold-adapted reassortant vaccines offer several advantages over the existing inactivated vaccine. These include the possible use of a single dose, and administration by the natural route of infection, i.e. intranasally. In addition, ca vaccines stimulate a wide range of antibody responses, and result in induction of both local and humoral immunity. Furthermore, these vaccines are cost-effective and can be rapidly produced and updated in the event of antigenic changes. In addition, laboratory guidelines are available for the assessment of virulence (reactogenicity in ferrets) and attenuation can be reproducibly achieved. Moreover, the presence of two phenotypic markers (the temperature-sensitive and cold-adapted phenotypes) allows for the evaluation of virulence and monitoring of the vaccine in the field.

However, despite the above-described advantages, until now virtually nothing has been known about the molecular basis of cold adaptation. Published information indicates that cold adaptation has produced one or more mutations in each of the genes encoding the internal proteins of the A/AA/6/60 master strain. Cox, N. J., et al., "Genetic Variation Among Influenza Viruses" (Academic Press), p. 639-652 (1981). However, all of the work has been done on viruses passaged 28 to 32 times in eggs in parallel with the virus passaged in primary chick kidney cells during cold adaptation. Cox, N. J., et al., *Virol.* 167:554-567 (1988). Studies, however, have shown a gradual buildup of mutations in the RNA1 of sequential 35° C. egg passages 2 through 28 of wild type viruses, and recent findings have shown the influence of host cell variation on influenza viruses passaged in chicken eggs. Katz, J. M., et al., *Virol.* 156:386-395 (1987). Thus, the mutations leading to cold adaptation and attenuation have heretofore been unknown.

It would thus be desirable to isolate and provide the wild type A/Ann Arbor/6/60 progenitor virus and determine the accurate nucleic acid sequence of its genome. It would further be desirable to identify the mutations leading to cold adaptation, thus accurately characterizing the nucleic acid sequence of the ca master strain. It would also be desirable to produce and provide cold-adapted influenza strains through reassortment with currently circulating wild type strains. It would also be desirable to produce and use a cold-adapted influenza vaccine to prevent and/or treat influenza.

SUMMARY OF THE INVENTION

The cold-adapted A/Ann Arbor/6/60 7PI (H2N2) influenza strain ("master strain") has been isolated and deposited, and its genome accurately sequenced and compared to its progenitor temperature-sensitive wild type E2(3) (wt 2(3)) virus. The A/Ann Arbor/6/60 virus is a single-stranded RNA virus having eight gene segments. During investigation of the virus leading to the vaccines of the present invention, unexpected deviations from previously reported sequences of the ca and wt were also identified. In particular, in the ca master strain sequences, seven nucleotide differences were found, occurring in the nucleoprotein gene (NP), the gene encoding an acidic polymerase protein (PA) and the gene encoding a basic polymerase polypeptide (PB2). The wt progenitor strain and ca master strain have both been deposited with the American Type Culture Collection, as set forth above.

In comparing the cold-adapted master strain to the wt progenitor strain, four nucleotide differences encoding two amino acid differences were found in three gene segments. Computer-predicted RNA folds projected different secondary structures between the cold-adapted and wild type molecules based on the two silent differences between them. Genes coding for the PA, matrix (M), and non-structural (NS) proteins were identical between the two viruses. The differences suggest that cold adaptation may serve to provide conformational changes in the RNA structure advantageous to growth at 25° C. and provide a new form of genetic stability to the highly variable RNA genome.

With the identification of the correct nucleotide sequence of the ca master strain and its deposit, reassortant strains can now be produced which can be used as vaccines, to prophylactically and therapeutically treat influenza. Reassortant strains are produced by genetically combining the ca master strain with a variety of epidemic wild type viruses to yield reassortants which contain the hemagglutinin (HA) and neuraminidase (NA) gene segments of the wild type virus and the other six genome segments of the ca master strain. The reassortants thus contain the epidemic wild type strain genes that code for immunizing antigens found on the surface of the virus particle and the ca master strain genes that are responsible for the attenuated phenotype in humans and animals. To produce the vaccines of the present invention, a cold-adapted reassortant vaccine strain is passed once to prepare a virus seed lot which is used to produce vaccine pools.

In practicing the present invention, the amount of vaccine to be used or administered, alone or in combination with other agents, may vary with the patient being treated and may be monitored on a patient-by-patient basis by the physician. The vaccines of the present invention may also be administered in combination with other vaccines. Generally, a therapeutically effective amount of the vaccine will be administered for a therapeutically effective duration. By "therapeutically effective amount" and "therapeutically effective duration" is meant an amount and duration to achieve the desired therapeutic or prophylactic result in accordance with the present invention with medically acceptable side effects, which can be determined by those skilled in the medical arts.

The vaccines of the present invention may comprise the reassortant virus as well as a pharmaceutical formulation, together with a pharmaceutically acceptable carrier therefor. Each carrier must be "acceptable" in the sense of being compatible with the other ingredients of the formulation and not injurious to the patient. Formulations include those suitable for oral, nasal, topical (including transdermal, buccal and sublingual), parenteral (including subcutaneous) and pulmonary administration. The formulations may conveniently be presented in unit dosage form and may be prepared by any methods well known in the art of pharmacy.

It will be appreciated that administration of the vaccines of the present invention will also be by procedures well-established in the pharmaceutical arts, e.g. preferably intranasally or orally, and most preferably intranasally. Intramuscular, intravenous and intradermal administration is also contemplated by the present invention, either alone or in combination.

The present invention thus comprises isolated nucleic and amino acids with sequences corresponding to the ca master and wild type strain sequences set forth in Sequence ID Listings 1-40. By "isolated" is meant substantially purified from the natural state through chemical, biochemical, immunological or other means, or obtained in substantially pure form by other methods known to those skilled in the art. By "substantially pure" is meant substantially free from undesirable contaminants such as other proteins. Thus, these terms are not meant to exclude synthetic and recombinant nucleic and amino acids which are contemplated within the scope of the present invention. These terms are also not meant to exclude nucleic and amino acids which are linked, bound or intentionally combined with other moieties such as transgenes, labels, flanking amino acid sequences and the like. It will also be appreciated that although the viruses of the present invention are RNA viruses, the present invention further includes DNA sequences corresponding and complementary thereto.

The present invention further comprises isolated or substantially pure ca master strain and wild type E2(3) A/AA/6/60 virus. By "isolated" or "substantially pure strain" is meant the viral strain substantially free from other contaminants such as other viruses, bacteria, and the like.

The present invention further comprises reassortant viruses produced by combining the cold-adapted master strain with a variety of epidemic wild type viruses. The two surface protein genes of an epidemic wild type virus are operatively-linked to the six internal genes of the cold-adapted master strain. By "operatively-linked" is meant attached or assembled in a manner which allows for expression of the surface and internal genes. In the context of reassortant viruses, operative linkage will allow for the packaging of the reasserted RNA into virions. It will also be appreciated that the term "gene" is used comprehensively to include all polynucleotide sequences coding for the gene product or protein, and is not limited to naturally occurring coding and regulating elements.

In addition, the present invention comprises the production and use of cold-adapted influenza vaccines to prevent and/or treat influenza.

Additional objects, advantages, and features of the present invention will become apparent from the following description and appended claims, taken in conjunction with the accompanying drawings and Sequence ID Listings.

BRIEF DESCRIPTION OF THE DRAWINGS

The various advantages of the present invention will become apparent to one skilled in the art by reading the following specification and subjoined claims and by referencing the following drawings in which:

DETAILED DESCRIPTION OF THE INVENTION

Overview

Figure 1:
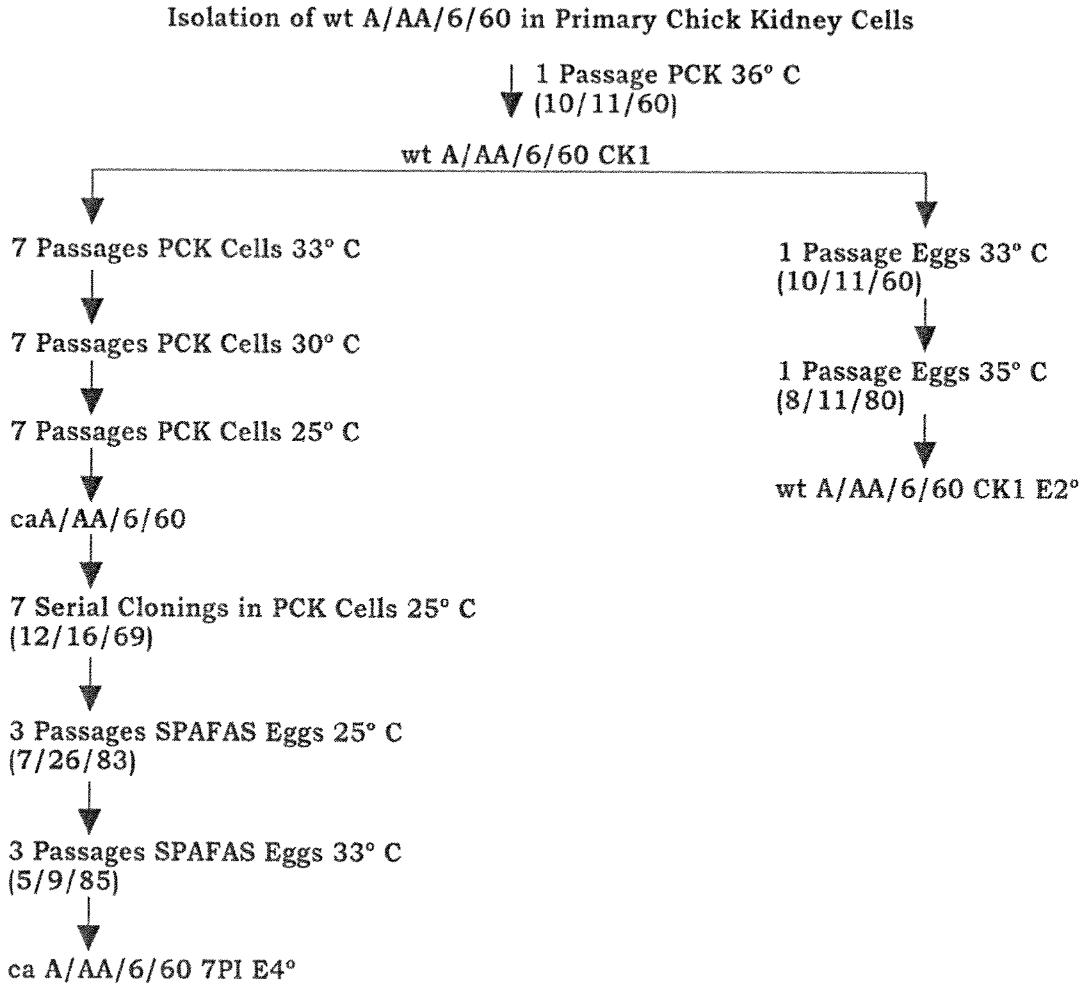
FIG. 1 shows the derivation of the progenitor wild type and cold-adapted master strain A/AA/6/60 in PCK cells.

The nucleic and amino acid sequences for the eight genes of the cold-adapted master strain A/Ann Arbor/6/60 7PI (H2N2) are set forth in Sequence ID Listings 1-20. The nucleic and amino acid sequences for the eight genes of the wild type A/Ann Arbor/6/60 (H2N2) Egg Passage 2(3) are set forth in Sequence ID Listings 21-40. Table 1 summarizes the gene products of influenza A and B virus genes. The cold-adapted master strain and wild type 2(3) progenitor have been deposited with the ATCC, as described above.

TABLE 1

Gene Products of Influenza A and B Viruses

| RNA | Gene Product(s) | Function |
|---|---|---|
| 1 | P82 | Viral polymerase component involved in RNA transcription |
| 2 | PB1 | Viral polymerase component with RNA transcription and replication activities |
| 3 | PA | Viral polymerase component involved in RNA replication |
| 4 | HA | Virion surface attachment and fusion glycoprotein, major antigenic determinant |
| 5 | NA | Virion surface glycoprotein with receptor-destroying enzyme activity, major antigenic determinant |
| 6 | NP | Major nucleocapsid structural component and type-specific antigen |
| | NB | Glycoprotein pututive membrane ion channel found only in type B |
| 7 | M1 | Membrane matrix protein and type-specific antigen |
| | M2 | Nonglycosylated membrane ion channel, found only in type A |
| 8 | NS1 | RNA-binding non-structural protein of transport function |
| | NS2 | Cellular and virion protein of unknown function |

The A/Ann Arbor/6/60 virus contains six internal genes, NS, M, NP, PA, basic polymerases (PB1 and PB2), and two surface genes, HA and NA. Seven nucleotide differences were found between the sequences of the present invention and those previously published for cold-adapted A/Ann Arbor/6/60: three in the NP gene, one in the PA gene and three in the PB2 gene. The eight viral genes and the discrepancies in the previously published sequences can be summarized as follows:

NS. The non-structural (NS) gene is the smallest RNA segment of influenza virus, 890 nucleotides long, and codes for the two non-structural proteins (NS1 and NS2) (nucleic acid Sequence ID Listing 1 and 3; amino acid Sequence ID Listings 2 and 4). There were no errors in the previously published sequences for the ca A/AA/6/60 NS1 and NS2 genes.

M. The matrix gene (M) is a 1,027 base nucleic acid sequence (nucleic acid Sequence ID Listings 5 and 7; amino acid Sequence ID Listings 6 and 8). There were also no errors in the previously published sequences for the ca A/AA/6/60 M gene.

NP. The nucleoprotein gene (NP) (nucleic acid Sequence ID Listing 9) is 1566 nucleotides in length and encodes a basic structural protein of 498 amino acid residues (amino acid Sequence ID Listing 10) which specifically interacts with RNA molecules to form ribonucleoprotein complexes and has sequences that direct its migration into the nuclei of infected cells. Despite previous reports, nucleotide 627 of NP is actually cytosine not adenine, and nucleotide 909 is guanine, not cytosine. In addition, nucleotide 113 was previously published as an adenine, although in GenBank it is reported as a cytosine. Cox, N. J. et al., *Virol.* 167:554-567 (1988). Regardless of this discrepancy, it is now known that nucleotide 113 is actually a cytosine.

PA. The polymerase acidic protein gene (PA) RNA sequence (nucleic acid Sequence ID Listing 11) is 2233 nucleotides in length and encodes an acidic polymerase protein 716 amino acids in length (amino acid Sequence ID Listing 12). Although previous publications indicate thymine at nucleotide 75 of PA, guanine is actually present at that position.

PB1. The polymerase basic 1 gene (PB1) RNA sequence (nucleic acid Sequence ID Listing 13) is 2341 nucleotides in length and encodes a basic polymerase protein 757 amino acids in length (amino acid Sequence ID Listing 14). No errors in the previously published sequence were found.

PB2. The polymerase basic 2 gene (PB2) RNA sequence (nucleic acid Sequence ID Listing 15) is 2341 nucleotides in length and encodes a basic polymerase polypeptide of 759 amino acids (amino acid Sequence ID Listing 16). There are three errors in the previously published sequence for PB2: thymine at 714 instead of the previously published cytosine at that position; guanine at 936 instead of adenine; and cytosine instead of thymine is the predominant base at 1933, with thymine as the secondary base.

HA and NA. The hemagglutinin gene (HA) and neuraminidase gene (NA) code for surface receptors. HA is 1773 nucleotides long and codes for a 562 amino acid sequence (nucleic acid Sequence ID Listing 17; amino acid Sequence ID Listing 18). See Schäfer, J. R. et al. *Virol.* 194:781-788 (1993). NA is 1467 nucleotides long and codes for a 469 amino acid sequence (nucleic acid Sequence ID Listing 19; amino acid Sequence ID Listing 20).

Results from previous studies indicate that cold adaptation causes mutations in every gene of the A/AA/6/60 master strain, thus ensuring the genetic stability of the virus. There are actually, however, four base differences in three of the internal genes of A/AA/6/60 after 28 passages in primary chicken kidney (PCK) cells and four passages in eggs. Two of the substituted bases are silent and two result in single amino acid differences in two of the genes. Moreover, the wt 2(3) progenitor virus is attenuated in ferrets. Hence, the stability and immunogenicity of the ca A/AA/6/60 vaccine appears to reflect inherent properties of the wt AIAA/6/60 E2(3) virus selected as the progenitor for the master strain. This interpretation is supported by the large number of amino acids unique to both wt 2(3) and ca viruses (see Table 3), some of which may be attenuating.

By attempting to identify changes arising from cold adaptation using the ca master strain and the wt 2(3) virus, there is at least one further critical variable—passage of the virus in different host tissues. It has been shown that the host cell influences the selection of antigenic variants of influenza viruses. Katz, J. M., et al., *Virol.* 156:386-395 (1987). In studies of the HA gene of H3N2 viruses, passage in Madin-Darby canine kidney (MDCK) cells and in primary chick kidney (PCK) cells selected populations that were homogeneous and true to the original isolate for this gene whereas passage in eggs selected heterogeneous populations. Katz, J. M., et al., *J. Gen. Virol.* 73:1159-1165 (1992). Thus, the changes observed could relate to the number of passages of each virus. The wild type 2(3) virus, with only two egg passages, is the only virus among all of those listed in GenBank to have isoleucine encoded by base 1276 of RNA2 and asparagine encoded by base 113 of NP. The positions of those two amino acids in the cold-adapted virus, with 29 PCK passages and 4 egg passages, are the same as those of all other viruses listed in GenBank. This finding suggests that the valine encoded by base 1276 in the cold-adapted PB1 is a host adaptation change rather than a cold adaptation change; the same holds for the threonine encoded by base 113 of the cold-adapted NP gene.

Differences between the wt 2(3) sequence as set forth herein and the wt 28-32 previously sequenced reflect mutations acquired during high passage in eggs at 35° C. Cox, N. J., et al., *Virol.* 167:554-567 (1988). These mutations may be the result of host adaptation in the egg or simply selection of the highly variable RNA population with the highest relative fitness. Clarke, D. K., et al., *J. Virol.* 67:222-228 (1993).

Since only the ca RNA1 has guanine (G) at position 141 and cytosine (C) at position 1933, by comparison with all other human RNA1 's in GenBank, the two base changes between the wt 2(3) and ca RNA1's may in fact be cold-adapted changes. No wild type human viruses, including the wt 2(3) progenitor, have G at 141 or C at 1933. This suggests that cold adaptation may operate at the RNA level. Recent findings indicate that unique RNA structures in influenza viruses may have common regulatory functions. Parvin, J. D., et al., *J. Virol.* 63:5142-5149 (1989). The more stable conformation of the ca molecule predicted by base pairing might provide a growth advantage over the predicted conformation of the wt 2(3) molecule. The importance of RNA structure to biological function has been well documented for poliovirus. Racaniello, V. R., et al., *Virol.* 155:498-507 (1986). The presence of a hairpin structure at the 5' noncoding end has been shown to be necessary for the ts phenotype of the virus.

Although RNA viruses have notoriously high mutation rates and have been referred to as "quasi-species," Holland, J. J., et al., *Cur. Topics Microbiol. Immunol.* (Springer-Verlag) 176:1-20 (1992), the ca A/AA/6/60 virus showed unusual stability after cold adaptation in PCK cells. In 33 passages there were only four sequence changes in the six internal genes, yielding a mutation rate of $2\times10^{-6}$. Compared to expected chance mutation rates calculated for the NS gene in MDCK cells, one would have expected 21 sequence changes. Parvin, J. D., et al., *J. Virol.* 59(2):377-383 (1986). Since RNA viruses have not been shown to have proofreading functions, this low mutation rate may be an inherent property of the wild type polymerases or a result of the cold adaptation process, or both. Suarez has shown that wild type viruses comprise subgroups with different mutation rates. Suarez, P., et al., *J. Virol.* 66(4):2491-2494 (1992). The wt A/AA/6/60 may have a dominant population with a more error-free polymerase. In addition, certain positions may simply be difficult for the polymerase to read, owing to conformation of the RNA molecule. Lowering the growth temperature by 10° C. slows the whole replicative process including the speed at which the polymerase unit is moving. *Thermus aquaticus* (Taq) polymerase is notorious for its high error rate due in part to the high temperature of its use, and it has been shown that a 5° C. reduction in temperature increases the fidelity of Tub polymerase. Kainz, P., et al., *Anal. Biochem.* 202:46-49 (1992). The lower temperature may provide a slowed-down environment conducive to faithful copying even in areas with conformational bends and twists. Thus the A/AA/6/60 polymerase might exhibit greater fidelity at 25° C. than at 35° C.

Single gene cold-adapted reassortants, constructed to identify the genetic basis of the ca and ts phenotypes and of attenuation, should be interpreted with care. For instance, in the study by Snyder et al., conducted in a background of A/Korea/1/82 genes, both PA and M were implicated in attenuation. Snyder, M. H., et al., *J. Virol.* 62(2):488-495 (1988). Neither gene showed sequence differences from its wt 2(3) counterpart in the present analysis. This would suggest that single gene wt 2(3) PA or wt 2(3) M in an A/Korea background would react similarly to the ca PA and M single genes. From the sequence data, one would also expect that RNA1 encoding PB2 would contribute to the ca phenotype in single gene studies and yet only PA was involved. Snyder, M. H., et al., *J. Virol.* 62(2):488-495 (1988). Gene constellation studies suggest that single gene studies in one wild type may be applicable to only that wild type. Subbarao, E. K., et al., *Virus Res.* 25:37-50 (1992). In a different wild type background, the assignment of phenotype to specific ca genes might change because other wild type genes might be dominant or carry natural extragenic suppressor mutations. This emphasizes the need for the presence of six genes from the ca virus rather than five in ca reassortants to ensure maximum stability. Maassab, H. F., et al., *J. Infect. Dis.* 146(6):780-790 (1982).

SPECIFIC EXAMPLE 1

Sequencing

A. Materials and Methods

Viruses. All viruses were supplied by Professor H. F. Maassab at the University of Michigan and the ca master strain and wild type progenitor strain viruses have now been deposited with the ATCC as previously set forth. Steps in the preparation of the ca master strain A/AA/6/60 7PI (H2N2) live influenza virus and the wt A/AA/6/60 (H2N2) egg passage 2(3) virus are shown in FIG. 1. In FIG. 1, PCK cells refers to primary chick kidney cells, SPAFAS refers to specific pathogen-free eggs and PI refers to plaque-purified. To guard against any possibility of mix-up in the two viruses, the passage history of both viruses was carefully traced and their separate identities were verified. Moreover, the two viruses were grown in different institutions and sequenced separately. The authenticity of the wt A/AA/6/60 E2(3) virus is supported by sequence differences between the HA's and NA's of the cold-adapted and wild type viruses. Viruses grown in 11-day old embryonated chicken eggs and virion RNA were prepared as previously described. Bean, W. J., et al., *Anal. Biochem.* 102:228-232 (1980).

Growth and Infectivity of Viruses. Plaque titrations were performed with both viruses in PCK cells at 25° C., 33° C., and 39° C., and in MDCK cells at 33° C. and 39° C. Mills, J., et al., *J. Infect. Dis.* 123:145-157 (1971). Plaque counts obtained at each of the three temperatures were compared to assess the ca and ts phenotypes of both viruses.

Ferret Studies. One week before infection with virus, 4 female ferrets were bled and screened for influenza antibody against A/Taiwan/1/86 (H1N1), A/Beijing/353/89 (H3N2), wt A/AA/6/60 (H2N2) E2(3) and B/Victoria/2/87. The animals' temperatures were taken twice a day for 1 week preceding their inoculation with $1\times10^{9}$ $EID_{50}$ of wt E2(3), and then until they were sacrificed at either 3 or 8 days after infection. Lungs and turbinates of the ferrets were examined by previously reported methods. Maassab, H. F., et al., *J. Infect. Dis.* 146(6):780-790 (1982).

Gene Cloning. Double-stranded cDNA was prepared as previously described. Huddleston, J. A., et al., *Nucleic Acids Res.* 10:1029-1039 (1982). Full-length double-stranded copies of genes 4 through 8 (HA, NA, NP, M, NS) were blunt-end ligated into the Pvu II site of vector Pvu II, obtained from C. Naeve at St. Jude Children's Research Hospital.

For the polymerase genes (PB1, PB2, PA), the first-strand cONA was amplified by the polymerase chain reaction (PCR) using phosphorylated primers. "Gene-cleaned" PCR product was blunt-end ligated into the Pvu II site of pATX.

Nucleic Acid Sequencing. Nucleotides of all eight cloned genes of each virus were sequenced by the method of Chen and Seeburg using alkali-denatured DNA templates. Chen, E. Y., et al., *DNA* 4:165-170 (1985). Due to the extreme heterogeneity of RNA viruses, several clones of each gene were sequenced to avoid reporting the sequence of a minor mutant population. Clones of each orientation were sequenced for each gene. If the two clones differed at any position, as many as 7 clones of each gene were sequenced and the consensus sequence was reported. Compressions were resolved by the addition of 42% formamide to the gels.

Differences between the cold-adapted virus and the wild type E2(3) virus were confirmed by direct sequencing of the virion RNA, a method which would expose any mutations introduced by use of the Taq polymerase. Air, G. M. *Virol.* 97:468-472 (1979).

Sequence Analysis. The IntelliGenetics software package (Palo Alto, Calif.) was used to analyze nucleotide sequence data. Chou-Fasman two-dimensional protein structure predictions were made with programs available at the St. Jude Molecular Biology Computing Center. The reliability of protein folding by this method is predicted to be approximately 60%. Fasman, G. D. "Prediction of Protein Structure and the Principals of Protein Confirmation" (Plenum, New York), p. 417-467 (1986).

The Zuker Fold program on the Cray Y-MP supercomputer at the Pittsburgh Supercomputing Center was used to study the folding of RNA molecules. Optimal foldings were obtained using the Zuker algorithm which calculates the structure exhibiting minimal free energy. Zuker, M., et al., *Nucleic Acids Res.* 9:133-148 (1981). This program calculates the structure that is energetically most favorable and has a predicted accuracy of 80%, although the structure with the lowest free energy may not represent all biologically active structures. Zuker, M., et al., *Nucleic Acids Res.* 9:133-148 (1981).

B. Results

Biological Properties. The ca and ts characteristics of the viruses in PCK cells was first examined. The ca master strain reached essentially the same titer at 25° C. ($3.0\times10^8$) as it did at 33° C., but failed to grow at 39° C. (see Table 2), fulfilling accepted criteria for cold adaptation and temperature sensitivity. By contrast, on day 6, the wt E2(3) virus had produced fewer than $1.0\times10^5$ plaques at 25° C., although by day 8 it had generated $5.0\times10^6$ plaques, indicating a subpopulation of virus capable of growth at low temperatures. The 4-log reduction in growth at 39° C. compared with that at 33° C. demonstrates the ts phenotype of the wt 2(3) virus. Similar results were obtained in MDCK cells at 33° C. and 30° C. (data not shown).

The pathogenicity of the wild type 2(3) virus was studied in ferrets. The virus was not recovered from lung tissue in any of the 4 animals examined, and it was recovered from turbinates in only the 2 animals sacrificed on day 3 (data not shown). None of the ferrets showed physical signs of illness, such as coryza, lethargy or sneezing. Rises in temperature ranging from 1° C. to 1.5° C. were observed, but they persisted for only several hours and were not considered significant since normal temperatures fluctuated by 1° C. These results, which correspond to findings with the ca virus, indicate that the wt 2(3) virus was attenuated before cold adaptation. Maassab, H. F., et al., *J. Infect. Dis.* 146(6):780-790 (1982).

TABLE 2

Infectivity Titers of A/AA/6/60 (H2N2)

| | Number of Plaques in Primary Chick Kidney Chick Cells[a] | | |
|---|---|---|---|
| Virus | 33° C.[b] | 39° C.[b] | 25° C. |
| ca Master Strain A/AA/6/60 (H2N2) 7PI (SE4) | $6.0\times10^8$ | $<1.0\times10^4$ | $5.0\times10^7$ on day 6[c]<br>$8.0\times10^7$ on day 7<br>$3.0\times10^8$ on day 8 |
| wt A/AA/6/60 (H2N2) E2(3) | $1.5\times10^8$ | $2.0\times10^4$ | $<1.0\times10^5$ on day 6<br>$8.0\times10^6$ on day 7<br>$5.0\times10^6$ on day 8 |

[a]Similar results were obtained in MDCK cells at 33° C. and 39° C.
[b]Infectivity titers at 33° C. and 39° C. were determined on post-infection day 4.
[c]Post-infection days.

Tests were also performed employing ferrets to determine whether the cold-adapted vaccine would interfere with or block growth of the influenza virus. The experimental protocol and results of this study are set forth in U.S. Pat. No. 5,149,531, issued Sep. 22, 1992 to Younger et al., hereby incorporated by reference.

Sequencing. Table 3 compares sequencing results of the ca master strain with wt E2(3) virus. The data represent consensus DNA sequencing of multiple clones. If the clone consensus indicated a difference between the two viruses, RNA sequence data were used to support the findings. Positions reported as mixed populations in Table 3 show the distribution of the clones.

Between the internal genes of the ca and the wt 2(3) viruses, no differences were found in the genes coding for PA, M or NS, even though PA and M were previously reported to be important for attenuation of the ca master strain and cold adaptation was attributed to PA. Snyder, M. H., et al., *J. Virol.* 62(2):488-495 (1988). Differences were found in the genes coding for PB2, PB1 and NP.

TABLE 3

Sequence Differences between wt 2(3) and ca A/Ann Arbor/6/60 Viruses

| | | | wt A/AA/6/60 E2 | | ca A/AA/6/60 | |
|---|---|---|---|---|---|---|
| Gene | Base No. | Amino Acid No. | Base | Amino Acid | Base | Amino Acid |
| PB2 | 141 | | A/g(4/2) | | G (5) | |
| | 1933 | | T/c(4/2) | | C/t(4/1) | |
| PB1 | 1276 | 418 | A (5) | Ile | G/a(4/3) | Val |
| PA | | | — | — | — | — |
| HA | 144 | 34 | A (2) | Asn | T (2) | Ile |
| | 455 | 138 | G (2) | Ala | A (2) | Thr |
| | 729 | 229 | A (2) | Lys | C (2) | Thr |
| NA | 394 | | C (2) | | T (4) | |
| | 604 | | A (2) | | T (4) | |
| NP | 113 | 23 | A/c(2/1) | Asn | C/a(3/1) | Thr |
| M | | | — | — | — | — |
| NS | | | — | — | — | — |

In Table 3 above, in positions with mixed bases, the capital letter represents the dominant base. The distribution of the clones representing the positions with differences between the wt 2(3) and the ca internal genes are shown next to the bases.

RNA1 (PB2). Two nucleotide differences, in bases 141 and 1933, were found between the ca and wt 2(3) RNA1 genes, which encode a basic polymerase protein 759 amino acids in length. Called PB2, this protein is part of the transcriptase complex and has been identified as recognizing and binding the cap structure of the host-cell primer RNA. Plotch, S. J., et al., *Cell* 23:847-858 (1981). Both changes are in the coding region but are silent. Moreover, bases 141 and 1933 of the ca RNA1 are unique among all other human RNA1 sequences in GenBank. Position 1933 in the wt 2(3) and ca RNA1 segments is a mixed population of two bases; however, the darker band in the RNA sequence (thymine M) in wt 2(3) and cytosine (C) in ca) conforms with the consensus DNA sequence reported in Table 3.

Figure 2:
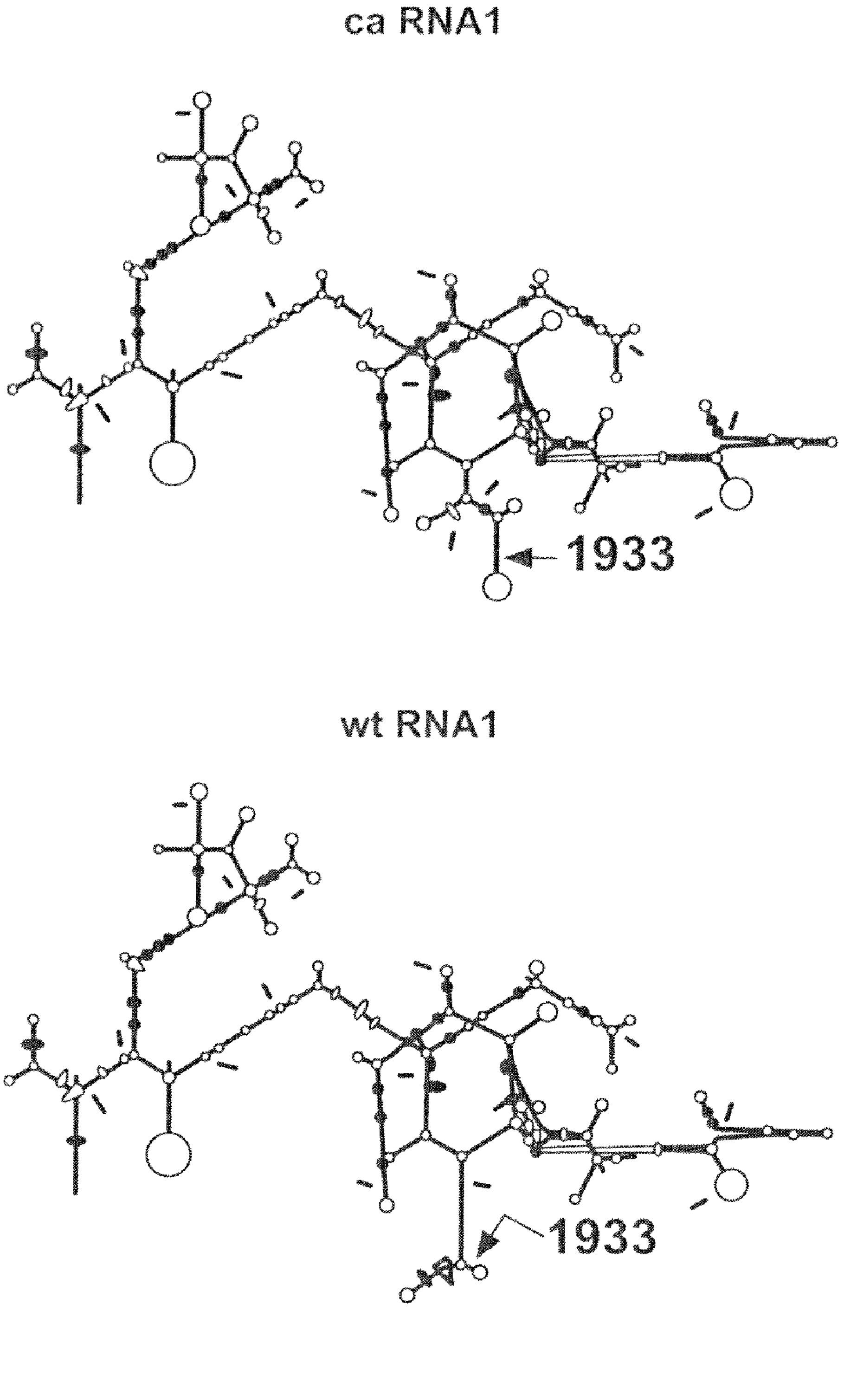
FIG. 2 shows the computer-projected RNA fold of cold-adapted and wild type 2(3) RNA1's (PB2's).

To assess the potential functional significance of the two nucleotide sequence differences between the ca and the wt 2(3) viruses, the Zuker RNA-fold algorithm and computer modeling techniques were used to predict RNA secondary structures. As shown in FIG. 2, the difference at base 141 does not impinge on the predicted structure of RNA1 because it is part of an unpaired loop in both molecules; however, the change at nucleotide 1933, T in wt 2(3) to C in ca (shown by arrows in FIG. 2), does affect the predicted fold of RNA1. The RNA fold of the ca virus has greater stability than the analogous fold of wt 2(3), as judged by its lower free energy of −736.2 compared to −733.6 for the wt 2(3) molecule. Both folds were pivoted −25° at pair 1068/1381 and 180° at pair 1675/1861 to better visualize the area of difference between the two molecules. The single base change at 1933 causes a cascade of 163 pairing differences, from base 1888 to base 2151, and thus might constitute a true cold adaptation. Similar RNA1 sequencing results were obtained for a wt A/AA/6/60 E3(4) passage virus.

RNA2 (PB1). The only nucleotide change found between the RNA2 genes of the ca and wt 2(3) viruses occurred at base 1276, resulting in a substitution of valine (ca) for isoleucine (wt 2(3)), both of which are hydrophobic and uncharged. RNA2 encodes a basic polymerase (PBl1) that mediates transcription and elongation of the mRNA chain. Braam, J., et al., *Cell* 34:609-618 (1983). Analysis of protein secondary structures predicted by Chou-Fasman and Garnier-Osguthorpe methods, as well as computer-predicted RNA structures, failed to reveal differences between the ca and wt 2(3) RNA2's. Valine is not an amino acid unique to the ca virus because later passages of the wt A/AA/6/60 virus (both wt E6 and wt E28) also have valine at this position, as do all other RNA2's in GenBank. Both DNA clones and RNA sequencing show that base 1276 comprises a mixed population of adenine (A) and guanine (G) in the ca RNA2; however, the G predominates.

RNA6 (NP). The nucleoprotein gene (RNA6) encodes a basic protein 498 amino acids in length which specifically interacts with RNA molecules to form ribonucleoprotein complexes. Huddleston, J. A., et al., *Nucleic Acids Res.* 10:1029-1039 (1982). NP is necessary for transcription and is a major determinant of host range. Huang, T. S., et al., *J. Virol.* 64:5669-5673 (1990); Scholtissek, C., et al., *Virol.* 147:287-294 (1985). There was one difference between the vv 2(3) and the ca NP molecules, at base 113 leading to substitution of threonine for asparagine, neither of which is hydrophobic or charged. The reverse change was reported in Cox, N. J., et al., *Virol.* 167:554-567 (1988).

Although having similar protein secondary structures by Chou-Fasman and Garnier-Osguthorpe predictions, the two RNA molecules showed a distinct difference in their predicted RNA structures. In wt 2(3) RNA6, base 113 creates a larger unpaired loop making the molecule less stable than ca RNA6 (structure not shown). DNA cloning and RNA sequencing revealed that base 113 is a mixed population of A and C in both the wt 2(3) and the ca RNA6's; however, in the wt 2(3) the consensus base is A and in the ca the consensus base is C.

The asparagine in the wt 2(3) virus is unique among all reported NP molecules (see Table 3), but not the threonine of the ca virus. The A/AA/6/60 (wt and ca) viruses are the only viruses in 54 GenBank sequences with an inserted A at base 1550 near the putative polyadenlyation signal.

RNA4 (HA) and RNA5 (NA). The sequences of ca RNA4 (HA) and ca RNA5 (NA) have not been previously reported, as neither molecule is included in ca reassortant vaccines. RNA4 encodes the hemagglutinin (HA) surface glycoprotein (562 amino acids in length), while RNA5, encodes the neuraminidase (NA) surface glycoprotein (469 amino acids in length). Two silent nucleotide differences were observed between ca RNA5 and wt 2(3) RNA5 at bases 394 and 604. Three additional differences seen at bases 144, 455, and 729 of ca RNA4 and wt 2(3) RNA4 coded for amino acid changes: asparagine to isoleucine (position 34), alanine to threonine (position 138) and lysine to threonine (position 229). The presence of clear differences in these two surface genes underscores the different passage histories of the two viruses and provides additional evidence for their separate identities.

SPECIFIC EXAMPLE 2

Sequence Comparisons

Sequence of Wild Type Progenitor. Table 4 presents positions for each gene where the ca and wt 2(3) viruses have unique amino acids, by comparison to previous GenBank sequences. Webster, R. G., et al., *Microbiol. Rev.* 56(1):152-179 (1992). In Table 5, a comparison to data previously published is shown and differences between the wt 2(3) and ca sequences as set forth herein, and the previously published sequences, are shown in bold type and bracketed. In positions with mixed bases, the capital letter represents the predominant base. Some of these amino acids found only in the two ts A/AA/6/60 viruses may be attenuating. However, many of the viruses reported in GenBank have been extensively passaged in the laboratory and will have accumulated mutations related to high relative fitness and host adaptation. Comparison to the A/AA/6/60 wt 28 virus previously sequenced provides further insight into attenuating lesions. Cox, N. J., et al., *Virol.* 167:554-567 (1988).

TABLE 4

Unique Amino Acid Differences between Temperature-sensitive and Attenuated wt 2(3) and ca A/AA/6/60 Viruses and Other Influenza Viruses in GenBank

| Gene | No. in GenBank | Base No. | A/AA/6/60 ca/wt 2(3) | A/AA/6/60 wt 28 | GenBank Viruses[b] |
|---|---|---|---|---|---|
| PB2[a] | 27 | 821 | Ser | Asn | Asn |
| | | 954 | Glu | Glu | Asp |
| PB1 | 23 | 215 | His | His | Pro |
| | | 1096 | Lys | Lys | Glu |
| | | 1276 | Val/Ile | Val | Val |
| | | 1395 | Asp | Glu | Glu |
| | | 1660 | Leu | Leu | Met |
| PA | 21 | 599 | His | His | Arg |
| | | 2167/8 | Pro | Leu | Leu |
| NP | 54 | 113 | Thr/Asn | Thr | Thr |
| | | 1550 | A | — | — |
| M1 | 44 | 453 | Val | Val | Ala |
| | | 457 | Leu | Leu | Phe |
| | | 678/9 | Val | Val | Ala |
| M2 | 44 | 847 | His | His | Arg |
| | | 969 | Ser | Ala | Ala |
| NS1 | 73 | 35 | Pro | Pro | Ser |
| | | 483 | Thr | Ala | Glu |

[a]Five other silent differences.

[b]Sources of GenBank viruses for each gene used in phylogenetic analysis are reported in Webster R.G., et al., *Microbiol. Rev.* 56(1):152-179 (1992).

TABLE 5

Summary of Comparative Sequence Data for A/Ann Arbor/6/60 Wild Type and Cold-Adapted Viruses

| | | Data from Study | | | | Data Previously Published[a] | | | |
|---|---|---|---|---|---|---|---|---|---|
| | | wt A/AA/6/60 E2(3) | | ca A/AA/6/60 | | ca A/AA/6/60 | | wt A/AA/6/60 E28 | |
| Gene | Base No. | Base | AA | Base | AA | Base | AA | Base | AA |
| PB2 | 141[+] | A/g | | G | | G | | A | |
| | 426 | C | | C | | C | | T | |
| | 714 | T | | [T] | | [C] | | [C] | |
| | 821 | G 265 | ser | G | ser | G | ser | A | asp |
| | 963 | G | | [G] | | [A] | | [A] | |
| | 1182 | T | | T | | T | | A | |
| | 1212 | T | | T | | T | | C | |
| | 1353 | G | | G | | G | | T | |
| | 1923 | G | | G | | G | | A | |
| | 1933[−] | T/c | | [C]/t | | [T] | | T | |
| PB1 | 123 | G | | G | | G | | A | |
| | 486 | T | | T | | T | | C | |
| | 1195 | G 391 | glu | G | glu | G | glu | A | lys |
| | 1276[^] | A/g 418 | ile | G/a | val | G | val | G | val |
| | 1395 | T 457 | asp | T | asp | T | asp | G | glu |
| | 1766 | G 581 | gly | G | gly | G | gly | A | glu |
| | 2005 | A 661 | thr | A | thr | A | thr | G | ala |
| | 2019 | T | | T | | T | | C | |
| PA | 20 | C | | C | | C | | T | |
| | 75 | G | | [G] | | [T] | | [T] | |
| | 1861 | G 613 | glu | G | glu | G | glu | A | lys |
| | 2167 | C 715 | pro | C | pro | C | pro | T | leu |
| | 2168 | C | | C | | C | | T | |
| HA | 144 | A 34 | asn | T | ile | | | | |
| | 455 | G 138 | ala | A | thr | | | | |
| | 729 | A 229 | lys | C | thr | | | | |
| NA | 394 | C | | T | | | | | |
| | 604 | A | | T | | | | | |
| NP | 113[<] | A/c 23 | asn | C/[a] | thr | [A] | asn | C | thr |
| | 146 | G 34 | gly | G | gly | G | gly | A | asp |
| | 627 | C | | [C] | | [A] | | A | |
| | 909 | G | | [G] | | [C] | | C | |
| | 1550 | A | | A | | A | | — | |
| M | 969 | T | ser | T | ser | T | ser | G | ala |
| NS | 483 | A 153 | thr | A | thr | A | thr | G | ala |
| | 813 | G | | G | | G | | A | |

[a]Cox, N.J., et al., Virol. 167: 554-567 (1988).

The distribution of the clones representing the positions with the differences between the wt 2(3) and the ca viruses are listed below:

[+]wt 2(3) PB2 141 four clones A, two clones G ca PB2 141 five clones G

[−]wt 2(3) PB2 1933 four clones T, two clones C ca PB2 1933 four clones C, one clone T

[^] wt 2(3) PB1 1276 five clones A ca PB1 1276 four clones G, three clones A

[<]wt 2(3) NP 113 two clones A, one clone C ca NP 113 three clones C, one clone A

SPECIFIC EXAMPLE 3

Reassortant Schemes

A. Type A Reassortants

The following is a procedure for developing Type A 6/2 cold-adapted influenza virus vaccine (CAIV) reassortants.

Materials

Media. The media used in this sample were prepared using the following components: a) HBSS −500 ml HBSS (BioWhitaker 10-508); 0.5 ml gentamicin sulfate 50 mg/ml (BioWhitaker 17-518); and adjust pH to 7.0 using 0.5N NaOH; b) 2× Eagle's −500 ml HBSS (BioWhitaker 10-508); 10 ml BME amino acids (GIBCO 320-1051); 10 ml BME vitamins (GIBCO 320-1040); 10 ml L-glutamine (GIBCO 320-5030); and 0.5 ml gentamicin sulfate 50 mg/ml (BioWhitaker 17-518); adjust pH to 7.0 using 0.5N NaOH; c) 0.5N NaOH-2 g NaOH; 100 ml Type I deionized water; sterilize by autoclaving 250° C. for 15 min, liquid cycle.

Inoculum. Inocula were prepared as follows: Cold-adapted Master Strain Parent (A/Ann Arbor/6/60-7PI)—make a $10^{-2}$ dilution in 2× Eagle's. Wild Type Parent—make a $10^{-1}$ dilution in 2× Eagle's. Combine equal volumes of the two diluted parents (1:1 dilution) and use this as the inoculum.

Cells. Use SPAFAS-derived primary chick kidney (SPF-PCK) cells grown in 16×125 mm tissue culture tubes on the fifth day after seeding.

Passages

SPF-CK1 Passage. SPF-CK1 passages were performed as follows: 1) remove growth media from ten SPF-PCK tubes; 2) wash SPF-PCK tubes with 1 ml of HBSS media; 3) inoculate with 0.3 ml of inoculum per tube; 4) adsorb at room temperature for 90 min while continuously rocking at low speed; 5) remove inoculum; 6) wash SPF-PCK tubes with 1 ml of HBSS media; 7) add 1 ml of 2× Eagle's media and incubate at 33° C.; 8) after 24 hr feed tubes with 0.3 ml of 2× Eagle's media; and 9) observe cells daily for cytopathic effect (CPE). When CPE is >75%, pass the tubes to CK2 (usually 48-72 hr).

SPF-CK2 Passage. SPF-CK2 passages were performed as follows: 1) remove growth media from the SPF-PCK tubes; 2) wash SPF-PCK tubes with 1 ml of HBSS media; 3) serially pass the CK1 passage with 0.3 ml of inoculum per tube; 4) adsorb at room temperature for 90 min while continuously rocking at low speed; 5) remove inoculum; 6) wash SPF-PCK tubes with 1 ml of HBSS media; 7) add 0.3 ml of ferret antisera against A/AA/6/60-7PI which has been treated by the trypsin-periodate method to remove nonspecific inhibitors which has been filter sterilized (0.22 μ). Use a 1:32-1:56 final dilution of sera (note that the treated sera is a 1:8 dilution); 8) adsorb at room temperature for 15 min while continuously rocking at low speed; 9) add 1 ml of 2× Eagle's media and incubate at 33° C.; and 10) observe cells daily for CPE. When CPE is >75%, pass the tubes to CK3 (usually 48-72 hr).

SPF-CK3 Passage. The procedure for this passage was identical to the CK2 passage. When the CPE of this passage is >75%, plaque-purify the material in SPF-PCK cells.

Plaque Purification/Genotype Screening

1PI (1st) Plaque Purification. First plaque purification and genotype screening were performed as follows: 1) serially dilute the CK3 passage in 2× Eagle's media through a $10^{-4}$ dilution, one ml of each dilution is needed per flask infected; 2) plaque the $10^{-3}$ and $10^{-4}$ dilution of each tube at 33° C. following the procedure for plaquing in PCK cells; 3) pick several plaques for each tube. Using a sterile cotton plugged Pasteur pipet which has been bent to a 90° angle remove the agar and cells surrounding a well-isolated plaque. Draw a small volume of HBSS into the Pasteur pipet prior to picking the plaque to facilitate the expulsion of the plaque from the Pasteur pipet. Transfer the plaque material to a sterile capped tube containing 0.5 ml of 2× Eagle's media. One plaque from each tube is passed in SPAFAS eggs and the other plaques should be frozen at −70° C. as backup material; 4) pass one plaque in two SPAFAS eggs (0.2 ml of inoculum per egg) at 33° C. for 72 hr. Refrigerate eggs at 4° C. for at least one hr prior to harvesting the allantoic fluid. Determine the hemagglutinin titer (HA) of the egg pool to confirm the presence of virus and determine plaquing dilutions for the next purification. Two eggs will provide all the virus needed; and 5) genotype the 1PI egg material following the genotype procedure to identify potential 6/2 candidates.

2PI (2nd) Plaque Purification. Second plaque purification and genotype screening were performed as follows: 1) plaque the 1PI egg material in SPF-PCK cells at 33° C. following the procedure for plaquing in PCK cells, using the following appropriate dilutions to obtain well-isolated plaques:

TABLE 6

| HA Titers | Approximate Dilutions |
|---|---|
| <1:32 | $10^{-3}$ and $10^{-4}$ |
| ≦1:128 | $10^{-4}$ and $10^{-5}$ |
| ≦1:512 | $10^{-5}$ and $10^{-6}$ |
| >1:512 | $10^{-5}$, $10^{-6}$ and $10^{-7}$ |

2PI plaques should be derived from the same material which is genotyped since the egg passage may exert selective pressure on the plaques; and 2) pick several plaques following the procedure previously described. One plaque from each tube will be replaqued in SPF-PCK cells and the other plaques should be frozen at −70° C. as backup material.

3PI (3rd) Plaque Purification. Third plaque purification and genotype screening were performed as follows: 1) plaque the 2PI plaques in SPF-PCK cells at 33° C. following the procedure for plaquing in PCK cells. The appropriate dilutions for this passage are $10^{-1}$ and $10^{-2}$; 2) pick several plaques following the procedure previously described. At this time you should know which are potential 6/2's and non-candidates can be discarded. One plaque will be amplified in SPAFAS eggs at 33° C. and the others should be frozen at −70° C. as backup material; 3) genotype the 6/2 candidates to confirm that 3PI passages have the 6/2 gene configuration; and 4) characterize the phenotypic profile of the 6/2 vaccine candidates at 25° C., 33° C. and 39° C. to confirm the presence of the ca and ts markers.

B. Type B Reassortants

The following is a procedure for developing Type B 6/2 cold-adapted influenza virus vaccine (CAIV) reassortants.

Materials

Media. The media used in part B of this example were prepared as described in part A above.

Inocula. Inocula of the ca master strain parent and wild type are diluted to $10^{-2}$.

Cells. SPAFAS primary chick kidney (SPF-PCK) were grown as described in part A above.

Passages

SPF-CK1 Passage. SPF-CK1 passages were performed as follows: 1) remove growth media from ten SPF-PCK tubes; 2) wash SPF-PCK tubes with 1 ml of HBSS media; 3) inoculate with 0.3 ml of inoculum per tube; 4) adsorb at room temperature for 90 min while continuously rocking at low speed; 5) remove inoculum; 6) wash SPF-PCK tubes with 1 ml of HBSS media; 7) add 0.3 ml of ferret antisera against B/AA/1/66 CL 4-1-7PI treated by the trypsin-periodate method to remove nonspecific inhibitors and filter sterilized (0.22 μ). Use a 1:56 final dilution of sera (note that the treated sera is a 1:8 dilution); 8) adsorb at room temperature for 15 min while continuously rocking at low speed; 9) add 1 ml of 2× Eagle's media and incubate at 25° C.; and 10) observe cells daily for cytopathic effect (CPE). When CPE is >75%, pass the tubes to CK2 (usually 72-96 hr).

SPF-CK2 Passage. SPF-CK2 passages were performed as follows: 1) remove growth media from the SPF-PCK tubes; 2) wash SPF-PCK tubes with 1 ml of HBSS media; 3) serially pass the CK1 passage with 0.3 ml of inoculum per tube; 4) adsorb at room temperature for 90 min while continuously rocking at low speed; 5) remove inoculum; 6) wash SPF-PCK tubes with 1 ml of HBSS media; 7) add 0.3 ml of ferret antisera against B/AA/1/66 CL 4-1-7PI treated by the trypsin-periodate method to remove nonspecific inhibitors which has been filter sterilized (0.22 μ). Use a 1:56 final dilution of sera (note that the treated sera is a 1:8 dilution); 8) adsorb at room temperature for 15 min while continuously rocking at low speed; 9) add 1 ml of 2× Eagle's media and incubate at 33° C.; and 10) observe cells daily for CPE. When CPE is >75%, pass the tubes to CK3 (usually 48-72 hr).

Plaque Purification/Genotype Screening

1PI (1st) Plaque Purification. First plaque purifications and genotype screening were performed as follows: 1) serially dilute the CK2 passage in 2× Eagle's media through a $10^{-4}$ dilution, one ml of each dilution is needed per flask infected; 2) plaque the $10^{3}$ and $10^{-4}$ dilution of each tube at 33° C. following the procedure for plaquing in PCK cells; 3) pick several plaques for each tube. Using a sterile, cotton-plugged Pasteur pipet which has been bent to a 90° angle, remove the agar and cells surrounding a well-isolated plaque. Draw a small volume of HBSS into the Pasteur pipet prior to picking the plaque to facilitate the expulsion of the plaque from the Pasteur pipet. Transfer the plaque material to a sterile capped tube containing 0.5 ml of 2× Eagle's media. One plaque will be passed in SPAFAS eggs and the others should be frozen at −70° C. as backup material; 4) pass one plaque in two SPAFAS eggs (0.2 ml of inoculum per egg) at 33° C. for 72 hr. Refrigerate eggs at 4° C. for at least one hr prior to harvesting the allantoic fluid. Determine the hemagglutinin titer (HA) of the egg pool to confirm the presence of virus and determine plaquing dilutions for the next purification. Two eggs will provide all the virus needed; and 5) genotype the 1PI egg material following the genotype procedure to identify potential 6/2 candidates.

2PI (2nd) Plaque Purification. Second plaque purification and genotype screening were performed as follows: 1) plaque the 1PI egg material in SPF-PCK cells at 33° C. following the procedure for plaquing in PCK cells. Use the appropriate dilutions to obtain well-isolated plaques, such as the following:

TABLE 7

| HA Titers | Approximate Dilutions |
|---|---|
| <1:32 | $10^{-3}$ and $10^{-4}$ |
| ≦1:128 | $10^{-4}$ and $10^{-5}$ |
| ≦1:512 | $10^{-5}$ and $10^{-6}$ |
| >1:512 | $10^{-5}$, $10^{-6}$ and $10^{-7}$ |

2PI plaques should be derived from the same material which is genotyped since the egg passage may exert selective pressure on the plaques; and 2) pick several plaques following the procedure previously described. One plaque will be replaqued in SPF-PCK cells and the others should be frozen at −70° C. as backup material.

3P1 (3rd) Plaque Purification. Third plaque purification and genotype screening were performed as follows: 1) plaque the 2PI plaques in SPF-PCK cells at 33° C. following the procedure for plaquing in PCK cells. The appropriate dilutions for this passage are $10^{-1}$ and $10^{-2}$; 2) pick several plaques following the procedure previously described. At this time you should know which are potential 6/2's and non-candidates can be discarded. One plaque will be amplified in SPAFAS eggs at 33° C. and the others should be frozen at −70° C. as backup material; 3) genotype the 6/2 candidates to confirm that 3PI passages have the 6/2 gene configuration; and 4) characterize the phenotypic profile of the 6/2 vaccine candidates at 25° C., 33° C. and 37° C. to confirm the presence of the ca and ts markers.

C. Influenza Virus

A number of cold-adapted reassortants and cold-adapted influenza vaccines (CAIV) have been produced and clinically tested using the general scheme set forth above with modifications known to or easily devisable by those skilled in the art without undue experimentation. In addition, the cold-adopted influenza vaccines that have proven efficacious are set forth in Table 10. The following Table sets forth the Type A and Type B reassortants:

TABLE 8

| CAIV | |
|---|---|
| TYPE A REASSORTANT | TYPE B REASSORTANT |
| A/Victoria/75 (H3N2) | B/Tecumseh/63/80 |
| A/Victoria/75 (H3N2) | B/Texas/1/84 |
| A/Swine/New Jersey/8/76/ (H1N1) | B/Ann Arbor/1/86 |
| A/Alaska/6/77 (H3N2) | B/Yamagata/16/88 |
| A/Alaska/6/77 (H3N2) | B/Bangkok/163/90 |
| A/USSR/90/77 (H1N1) | B/Panama/45/90 |
| A/Hong Kong/77 (H1N1) | B/Panama/45/90 |
| A/California/10/78 (H1N1) | |
| A/Alaska/6/77 (H3N2) | |
| A/Peking/2/79 (H3N2) | |
| A/Washington D.C./897/80 (H3N2) | |
| A/Shanghai/31/80 (H3N2) | |
| A/Korea/1/82 (H3N2) | |
| A/Dunedin/6/83 (H1N1) | |
| A/Bethesda/1/85 (H3N2) | |
| A/Texas/1/85 (H1N1) | |
| A/Kawasaki/9/86 (H1N1) | |
| A/Wyoming/1/87 (H3N2) | |
| A/Los Angeles/2/87 (H3N2) | |
| A/Shanghai/11/87 (H3N2) | |
| A/Shanghai/16/89 (H3N2) | |
| A/Guizhou/54/89 (H3N2) | |
| A/Chick/Germany/N/49 (H10N7) | |
| A/Equine/Miami/1/63 (H3N8) | |
| A/Beijing/352/89 (H3N2) | |
| A/Yamagata/32/89 (H1N1) | |
| A/Texas/36/91 (H1N1) | |
| A/Beijing/352/89 (H3N2) | |
| A/Los Angeles/2/87 (H3N2) | |

SPECIFIC EXAMPLE 4

CA Influenza Virus Reassortant

Vaccine Pools

Facilities. The inoculation, harvesting, pooling, and filling operations were performed in a Biohazard Laminar Flow Hood (Type A/B3). All containers and equipment utilized were sterilized within 72 hr prior to use.

Production Substrate. Ten-day old incubated, specific pathogen free—complement fixation avian leukosis (SPF-COFAL) negative embryonated hens' eggs from SPAFAS, Inc. (Norwich, Conn.) were used. Quality Control Sheets for the flocks were obtained and retained to maintain traceability of eggs.

Cold-adapted Reassortant Vaccine Donor Strain. The cold-adapted reassortant vaccine donor strain passage will vary between SPF egg passage 1 (SEl1) and SE4. These passages (SE1-SE4) of the donor virus were produced as follows: The virus was thawed and diluted 1:100 to 1:10,000 (strain-dependent) in HBSS. Ten-day old embryonated eggs were inoculated via the allantoic route with 0.1 ml of the indicated diluent. All eggs were incubated at 33° C. for 40-72 hr (strain-dependent) at which time they were chilled at 4° C. for 1-2 hr prior to the harvesting of the allantoic fluid. This material was passed once to prepare the seed lot.

A. Virus Seed Production

The virus seed lot was used as the seed for the production of all vaccine pools. All work was done in production facilities.

Inoculation. The seed virus was thawed and diluted 1:100 to 1:10,000 (strain-dependent) in HBSS containing 1% of 10×SPG (sucrose, 2.18M; $KH_2PO_4$, 0.038M; $K_2HPO_4$, 0.072M; potassium glutamate, 0.049M). The ten-day old embryonated eggs were inoculated via the allantoic route with 0.1 ml of the indicated diluent. All eggs were incubated at 33° C. for 40-72 hr (strain-dependent) at which time they were candled and any dead embryo was discarded. All live eggs were chilled overnight at 4° C. prior to the harvesting of the allantoic fluid.

Harvest and Clarification. Allantoic fluids were harvested and pooled in approximately 180 ml amounts. The harvested allantoic fluid was incubated at 37° C. (water bath) for 60 min to elute any virus adsorbed to red blood cells. Each bottle was then clarified by centrifugation at 1400 g for 15 min. 10×SPG was added to each harvest to achieve a 10% v/v suspension for virus stabilization. The harvest bottles were pooled. Sterility assays were carried out on the pool (dual sterility tests in both fluid thioglycolate and tryptone soya broth at 33° C. and 22° C.). The seed pool was assayed for hemagglutinin activity and aliquotted in the appropriate volumes needed for vaccine production.

B. Virus Pool Production

Inoculation. The seed virus was thawed and diluted 1:100 to 1:10,000 (strain-dependent) in HBSS containing 1% of 10×SPG. The ten-day old embryonated eggs were inoculated via the allantoic route with 0.1 ml of the indicated diluent. For negative controls, approximately 30 eggs were inoculated via the allantoic route with 0.1 ml of the indicated diluent. All eggs were incubated at 33° C. for 40-72 hr (strain-dependent) at which time they were candled and dead embryos were discarded. All live eggs were chilled overnight at 4° C. prior to the harvesting of the allantoic fluid.

Harvest and Clarification. Allantoic fluids were harvested and pooled in approximately 180 ml amounts. The harvested allantoic fluid was incubated at 37° C. (water bath) for 60 min to elute any virus adsorbed to red blood cells. Each bottle (control and infected) was then clarified by centrifugation at 1400 g for 15 min. 10×SPG was added to each harvest to achieve a 10% v/v suspension for virus stabilization. Aliquots were removed from each harvest bottle to form a sample master pool. Sterility assays were carried out on each individual bottle and on the sample master pool; dual sterility tests in both fluid thioglycolate and tryptone soya broth at 33° C. and 22° C. were conducted. The master pool was assayed for hemagglutinin activity and virus characterization (phenotype and genotype assays).

Pooling, Treatment and Dispensation. When the preliminary tests (sterility and virus characterization) proved satisfactory, the sterile harvests were thawed and pooled. Fluids were passed through sterile gauze pads to remove any membranous material that may be present. Antibiotics were added to the final pools to achieve the following concentrations: neomycin 100 mcg/ml, amphotericin B (I.V.) 5 mcg/ml.

Control Fluids: This pool was distributed into the appropriate aliquots needed for subsequent testing for adventitious agents. During dispensation the fluid was kept chilled in an ice-water bath. The fluids were stored at <−75° C. in a mechanical freezer.

Virus-infected Fluids: This pool was distributed into the appropriate aliquots needed for subsequent safety testing. The remainder of the fluid was distributed into aliquots for use as a live cold-adapted influenza virus vaccine. During dispensation the fluid was kept chilled in an ice-water bath. The fluids were stored at <−75° C. in a mechanical freezer.

Tests for Adventitious Agents. The following are microbial sterility tests: 1) pre-antibiotic testing for bacteria with fluid thioglycolate at 22° C. and 33° C., and tryptone soya broth media at 22° C. and 33° C.; and 2) post-antibiotic testing for bacteria in Lowenstein-Jensen egg medium, and for mycoplasma and brucella.

Identity in tissue culture is tested using serum-neutralization in Primary African Green Monkey Kidney (AGMK) cells.

Tissue culture tests for adventitious agents are performed using: 1) Primary African Green Monkey Kidney (AGMK) cells; 2) Primary Bovine Embryonic Kidney (BEK) cells; 3) Primary Human Amnion (PHA) cells; 4) Primary Rabbit Kidney (PRK) cells; 5) Human Diploid Fibroblast (MRC-5) cells; and 6) Human Carcinoma of the Cervix (HeLa) cells.

Animal tests for adventitious agents are performed using: 1) adult mice (ICR); 2) suckling mice (CD-1); and 3) adult guinea pigs. Guinea pig tests are conducted for *M. tuberculosis*, Q-fever and *B. abortus* antibodies.

A test for reverse transcriptase by assaying for the detection of RNA-dependent DNA-polymerase activity is also performed.

Final container/pool testing is performed by the following tests: microbial sterility is tested with fluid thioglycolate at 22° C. and 33° C. and fluid soybean-casein digest; COFAL testing is performed to test for avian leukosis virus; general safety testing using mice and guinea pigs; virus characterization including infectivity with $TCID_{50}$ in Madin-Darby Canine Kidney (MDCK) cells, plaquing efficiency with Madin-Darby Canine Kidney (MDCK) cells with Plaque Forming Unit (PFU) determination at 34, 36, 37, 38 and 39° C., and SPF derived Primary Chick Kidney (SPCK) cells with Plaque Forming Unit (pfu) determination at 25, 33 and 39° C. for confirmation of phenotypic markers; antigenic analyses using hemagglutinin inhibition assay and neuraminidase inhibition assay; reactogenicity in ferrets; hemagglutinin activity; and passage level, wherein the final passage of the vaccine will vary between SPF Egg Passage 3 (SE3) and SE6.

SPECIFIC EXAMPLE 5

Characterization of CA Vaccines

A. CA Vaccine Evaluation

Production lots of cold-adapted influenza vaccines were evaluated prior to distribution to certify that they were identical to the seed strains from which they were produced. The production lots underwent three different tests to certify that they were identical to the seed strains: phenotypic evaluation, genotypic evaluation and ferret reactogenicity studies.

Phenotypic Evaluation of Cold-adapted Influenza Vaccines. Cold-adapted influenza vaccines contain two stable phenotypic markers, the cold-adapted (ca) marker and the temperature-sensitive (ts) marker. Presence of the ca marker is confirmed by comparable viral growth at 25° C. and 33° C. The ts marker is confirmed by a minimum 100-fold decrease in viral growth at 39° C. as compared to 33° C. for the Type A cold-adapted influenza vaccine. Viral growth is quantified as plaque-forming units/milliliter (pfu/ml) in primary chick kidney cells. Production lots are checked to certify that they have both of the phenotypic markers.

Genotypic Evaluation of Cold-adapted Influenza Vaccines. Influenza viruses are negative-stranded RNA viruses with eight unique strands of RNA, each of which corresponds to an individual gene. As described above, the cold-adapted influenza vaccine is a 6/2 reassortant which contains the six attenuated internal genes of the master strain parent with the two genes coding for the surface antigens of the wild type parent. Since the genes have different electrophoretic mobilities, they can be differentiated via polyacrylamide gel electrophoresis. Production lots are checked to certify that they have the 6/2 gene constellation of the seed strain.

Ferret Reactogenicity Studies. The ferret is the animal model of choice for testing the potential virulence of influenza viruses. The cold-adapted influenza vaccine is attenuated in ferrets and is characterized by an asymptomatic infection with viral growth restricted to the nasal turbinates. In this study, a ferret was infected with a high multiplicity of infection dose and monitored twice daily for symptoms of influenza. On day 3, the peak day for viral replication, the ferret was euthanized and the turbinate and lung were checked for viral growth. Production lots were checked to confirm that they are attenuated in the ferret model.

B. Materials and Methods

Preparation of PCK Cells

Media and Materials. The media used in this example are prepared with the following components: a) 199 with 10% FBS—450 ml sterile Type I deionized water; 50 ml Fetal Bovine Sera—heat inactivated; 50 ml 10×199 (GIBCO #330-1181); 10 ml L-glutamine (GIBCO 320-5030); 0.5 ml gentamicin sulfate (50 mg/ml) (M.A. Bioproducts 17-518); and 16 ml 1.4% $NaHCO_3$, pH to 6.8 with 0.5N NaOH. HBSS w/P&S—500 ml HBSS (M.A. Bioproducts 10-508); and 0.5 ml gentamicin sulfate (50 mg/ml) (M.A. Bioproducts 17-518); b) 0.25% trypsin—1 L HBSS (M.A. Bioproducts 10-508); and 2.5 g trypsin 1:250 (Difco 0152-15-9). Dissolve in HBSS by stirring at room temperature, filter sterilize (0.22 μ), pH to 7.6 with 0.5N NaOH after filtering; c) 0.5N NaOH—2 g NaOH; and 100 ml Type I deionized water; sterilize by autoclaving 250° C. for 15 min, liquid cycle; d) 1.4% $NaHCO_3$—100 ml Type I deionized water; 1.4 g $NaHCO_3$; and 0.1 ml 4% Phenol Red. Sterilize—autoclave 250° C. for 15 min, liquid cycle; e) 4% Phenol Red—2 g Phenol Red (Difco 0203-11-2); 39 ml Type I deionized water; and 11 ml 0.5N NaOH; sterilize by autoclaving 250° C. for 15 min, liquid cycle.

The following materials are also used: sterile instruments; sterile cotton balls; sterile gauze; sterile Petri dish; sterile 50 ml centrifuge tubes; ether jar and diethyl ether; dissecting boards and pins; and 70% ethanol.

Procedure. The following procedures are performed: 1) sacrifice 1 to 3-day old chicks with ether; 2) place chicks on dissecting board (backs against board) and pin the wings and feet; 3) wash chick with 70% ethanol; 4) cut away skin starting at throat to totally expose chest and abdomen using one set of sterile instruments; 5) using a second set of sterile instruments, cut along each side of the rib cage, peel down rib cage and omentum to expose internal organs; 6) with new sterile instruments cut the esophagus and trachea, peel down internal organs to expose the kidneys; 7) swab the body cavity with sterile cotton balls to remove blood; 8) with new sterile instruments remove kidneys and place in a Petri dish with HBSS; 9) with new sterile instruments remove connective tissue from the kidneys; 10) transfer kidneys to a 50 ml centrifuge tube. Keep the kidneys near the top for mincing; 11) mince the kidneys with a new set of instruments, using recurved scissors; 12) wash the kidneys three times with HBSS (10 ml per wash) and discard all washes; 13) add 5 ml of 0.25% trypsin per chick and incubate at 35° C. for ten min with occasional shaking; 14) shake vigorously by hand for three minutes. (The trypsinization times can vary with the activity of each lot of trypsin used); 15) centrifuge for 10 min at 1000-1200 RPM; 16) pour off supernatant and resuspend cells in 10 ml of 199 w/10% FBS; 17) filter through sterile gauze into 20 ml per chick of 199 w/10% FBS, and dispense into culture flasks, tubes or plates and incubate at 35° C.; 18) feed 100% with 199 w/10% FBS after 72 hr; and 19) incubate at 35° C., cells should be usable 96 hr after seeding.

Plaquing PCK Cells

Media. The following media are used: a) Kilbourne—350 ml sterile Type I deionized water; 100 ml 10×199 (GIBCO #330-1181); 20 ml MEM amino acids (50×) (M.A. Bioproducts 13-606); 7.5 ml 5% $NaHCO_3$;10 ml MEM vitamins (100×) (M.A. Bioproducts 13-607); 2.86 ml 35% Bovine Sera Albumin (SIGMA A-8918); and 0.5 ml gentamicin sulfate (50 mg/ml) (M.A. Bioproducts 17-518) adjust pH to 7.0 using 0.5N NaOH; b) 2× Eagle's—500 ml HBSS (M.A. Bioproducts 10-508); 10 ml BME amino acids (GIBCO 320-1051); 10 ml BME vitamins (GIBCO 320-1040); 10 ml L-glutamine (GIBCO 320-5030); and 0.5 ml gentamicin sulfate 50 mg/ml (M.A. Bioproducts 17-518) adjust pH to 7.0 using 0.5N NaOH; c) 1% DEAE dextran—1 g DEAE dextran (Pharmacia 17-0350-01); and 100 ml sterile Type I deionized water (Filter Sterilize (0.221 μfilter)); d) 1% Neutral Red—1 g Neutral Red (DIFCO Bacto Neutral Red 0208-13); 100 ml sterile Type I deionized water; 1) dissolve in $H_20$ by stirring at room temperature for several hours; 2) filter through Whatman #1 filter paper to remove undissolved particulates; 3) aliquot into light-proof bottles and autoclave to sterilize (15 psi for 15 min); and 4) store at room temperature (works best when the stain has aged; unlimited shelf life); e) HBSS—500 ml HBSS (M.A. Bioproducts 10-508); and 0.5 ml gentamicin sulfate 50 mg/ml (M.A. Bioproducts 17-518), adjust pH to 7.0 using 0.5N NaOH); f) 0.5N NaOH—2 g NaOH; and 100 ml Type I deionized water. Sterilize by autoclaving 250° C. for 15 min, liquid cycle; g) 1.6% purified agar—1.6 g BBL agar purified (Becton Dickison 11853); and 100 ml sterile Type I deionized water. Autoclave to sterilize and prepare while virus is adsorbing—make volume needed for overlay.

Procedure. The following procedure was used: 1) set up water bath to keep media and agar at proper temperature (39-41 ° C.); 2) make serial dilutions of the virus in 2× Eagle's (1 ml of diluted virus per 25 $cm^2$ tissue culture flask); 3) remove media from tissue culture flasks and wash once with HBSS, 2 ml per 25 $cm^2$ flask; 4) add 1 ml of diluted virus per 25 $cm^2$ flask; 5) adsorb virus at room temperature for 1 hr with gentle rocking; 6) remove virus inoculum from flask; 7) overlay with a 1:1 mixture as described below; 5 ml per 25 $cm^2$ flask (1st Overlay—see below); 8) cool bottles until agar gels at room temperature, approximately 10 min; 9) incubate at desired temperatures (Type A Influenza—Phenotype 25°, 33° and 39° C.; Type B Influenza—Phenotype 25°, 33° and 37° C.); 10) after appropriate incubation overlay with 1:1 mixture as described below, 4 ml per 25 $cm^2$ flask (2nd Overlay—see below);

TABLE 9

| Temperature | Incubation until 2nd overlay |
|---|---|
| 25° C. | 96 hr |
| 33°,37°,39° C. | 48 hr |

11) cool bottles until agar gels at room temperature, approximately 10 min; 12) incubate at desired temperature; and 13) check daily for plaques. At 33°, 37° and 39° C., all plaques should be visible within 48 hr after the second overlay. At 25° C., it can take up to 168 hr (7 days) after the second overlay for all plaques to be visible.

The 1st Overlay is prepared by a 1:1 mixture of the following media mixture with 1.6% purified agar: 100 ml Kilbourne media and 3 ml 1% DEAE dextran. The amount of DEAE dextran needed will vary with the batch of purified agar. This concentration should work for most batches.

The 2nd Overlay—Neutral Red is prepared by a 1:1 mixture of the following media mixture with 1.6% purified agar: 100 ml Kilbourne media; 3 ml 1% DEAE dextran. The amount of DEAE dextran needed will vary with the batch of purified agar. This concentration should work for most batches; and 2 ml 1% Neutral Red. The amount of Neutral Red needed can vary with the batch. For long-term consistency, enough Neutral Red can be made at one time to last several years.

RNA Labelling

Media and Solutions. The following media and solutions are used: a) HBSS—500 ml HBSS (M.A. Bioproducts 10-508); and 0.5 ml gentamicin sulfate 50 mg/ml (M.A. Bioproducts 17-518) (adjust pH to 7.0 using 0.5N NaOH); b) 2× Eagle's—500 ml HBSS (M.A. Bioproducts 10-508); 10 ml BME amino acids (GIBCO 320-1051); 10 ml BME vitamins (GIBCO 320-1040); 10 ml L-glutamine (GIBCO 320-5030); 0.5 ml gentamicin sulfate 50 mg/ml (M.A. Bioproducts 17-518) (adjust pH to 7.0 using 0.5N NaOH); c) $^3$H-uridine-[5,6-$^3$H] Uridine—1.0 mCi/ml (Amersham, Inc. TRK 410); d) 5 M NaCl-146.1 g NaCl (Bring the volume to 500 ml with Type I deionized water); e) 1 M Tris-HCl (pH 7.4)—60.55 g Trizma Base (Sigma T-1503); 400 ml Type I deionized water; 35 ml concentrated HCl; and 0.5 ml diethylpyrocarbonate (Sigma D-5758); Allow solution to cool to room temperature. Adjust pH to 7.4 with HCl. Bring the volume up to 500 ml with Type I deionized water. Sterilize by autoclaving 250° C. for 15 min, liquid cycle; e) 0.5 M EDTA—186.1 g disodium EDTA (Sigma ED2SS); 800 ml Type I deionized water; and 20 g NaOH. Mix and adjust the pH to 7.4 with NaOH, sterilize by autoclaving 250° C. for 15 min, liquid cycle; f) 30% sucrose—150 g sucrose (Sigma S-9378); 10 ml 5 M NaCl; 5 ml 1 M Tris-HCl, pH 7.4; and 1 ml 0.5 M disodium EDTA (ethylenediaminetetraacetic acid) (Sigma ED2SS). Bring up to 500 ml with Type I deionized water; g) STE (Sodium-Tris-EDTA)—1 ml 0.5 M disodium EDTA (Sigma ED2SS); 10 ml 5.0 M NaCl; and 5 ml of 1 M Tris-HCl, pH 7.4 (Trizma Base) (Sigma T-1503). Add 484 ml of Type I deionized water; h) proteinase-K—proteinase-K 20 mg/ml (Beckman-340321). Dilute 100 mg in 5 ml of sterile Type I deionized water; i) SDS—sodium dodecyl sulfate (Sigma L-5750), 10% (w/v) in Type I deionized water; j) 1/10×TBE loading buffer—0.5 ml 10×TBE; 0.5 ml 10% SDS; 1.0 g ficoll (Sigma F-4375); 2.5 ml glycerol (Baker 2140-03); and 0.125 g Bromophenol Blue (Bio-Rad 161-0404). Bring up to 50 ml with Type I deionized water.

ProtocoL The following protocol is used:

Day 1: 1) Use 2-25 $cm^2$ flasks of primary chick kidney cells; 2) remove media and wash with HBSS, 2 ml/flask; 3) infect cells with virus—2 ml virus diluted 1:2 in 2×Eagle's; 4) rock cells gently for 1 hr at room temperature; 5) remove inoculum; 6) add label, use 0.2 mCi—0.25 mCi $^3$H-uridine/flask. Diluted in 2×Eagle's, total volume 1.5 ml/flask; 7) place in 33° C. incubator for 4 hr; 8) after 4 hr, add 3.5 ml 2× Eagle's to each flask; and 9) incubate at 33° C. for 48 hr.

Day 3: 1) Transfer fluid from the 2 flasks into a 15 ml centrifuge tube; 2) centrifuge at 500 g for 15 min at 4° C.; 3) pour supernatant into 30 ml Oakridge tubes; 4) underlay supernate with 7.5 ml 30% sucrose; 5) balance tubes with STE; 6) spin at 22,500 rpm for 2-½ hr in a Beckman type 30 rotor; 7) pour fluid from tubes into beaker ($^3$H aqueous waste—discard); 8) let. tubes sit on paper inverted for 5-10 min; 9) mark pellet—dry tube with Kimwipe; 10) resuspend each pellet in 200 μl STE, place suspension in a 1.5 ml centrifuge tube; 11) add 8 μl proteinase K (0.16 mg) to each tube, mix and incubate at 37° C. for 10 min; 12) add 10 μl of 10% SDS. Mix and incubate at 37° C. for 10 min; and 13) add 0.65 ml of 95% EtOH. Mix and place at −20° C. overnight.

Day 4: 1) Pellet the RNA in a microcentrifuge for 15 min at 4° C.; 2) empty EtOH into beaker—drain tubes upside down for several min; 3) dry the tubes in a Speedvac concentrator for approximately 10-20 min; 4) resuspend pellet in 32 μl of 1/10×TBE loading buffer; 5) heat at 56° C. for 2-3 min; 6) remove 2 μl sample and mix with 2 ml of liquid scintillation fluid; 7) count on Channel 1 for 0.5 min in liquid scintillation counter to get CPM (counts per min); 8) freeze sample until used at −70° C.; 9) heat at 56° C. for 2-3 min before loading; and 10) load 150,000-200,000 CPM.

Mixed Agarose-PAGE

Reagents. The following reagents were employed: a) 30% acrylamide, 1.5% bis-acrylamide—30 g acrylamide (Bio-Rad 115009B); and 1.5 g bis-acrylamide (Bio-Rad 41936B). Bring up to 100 ml with Type I deionized water; b) 10×TBE Buffer—54 g Trizma Base (0.89 M) (Sigma T-1503); 27.5 g boric acid (0.89 M) (Mallinckrodt CAS10043-35-3); 4.65 g EDTA disodium salt (20 mM); (ethylenediaminetetraacetic acid) (Sigma ED2SS). Bring up to 500 ml with Type I deionized water; c) 10% w/v SDS—10 g sodium dodecyl sulfate (Sigma L-5750). Bring up to 100 ml with Type I deionized water; d) diethylpyrocarbonate—diethyl pyrocarbonate 50 ml in 100 ml deionized water (Sigma D-5758); e) 1×TBE running buffer—216 g Trizma Base (89 mM) (Sigma T-1503); 110 g boric acid (0.89 M) (Mallinckrodt CAS10043-35-3); 18.6 g EDTA disodium salt (20 mM) (Sigma ED2SS); (ethylenediaminetetraacetic acid); and 20 g sodium dodecyl sulfate (SDS) (0.1%) (Sigma L-5750). Bring up to 20 liters with Type I deionized water and mix well; f) 10% ammonium persulfate—0.3 g ammonium persulfate (Bio-Rad M3992); bring up to 3.0 ml. Stable for 7 days at 4° C.; g) TEMED—tetramethylethylenediamine (Bio-Rad 161-0801); h) agarose—Type V—high gelling temperature (SIGMA A-3768); i) salicylic acid—0.3 g salicylic acid (Sigma S-3007); 36 g hexadecyltrimethylammonium bromide (Sigma H-5882); and 300 ml Type I deionized water.

Procedure. The following procedure is used for mixed acrylamide/agarose gel (3.0% acrylamide/0.6% agarose): Note that for proper polymerization of the gel, it must be at 56° C. for 20 min after pouring. The standard procedure is to place the plates vertically in a 56° C. water bath such that the water is within 1 inch of the plate tops 1) Combine and mix for 15 min: 0.6 g agarose Type V high gelling temperature, 92 ml Type I deionized water, and 50 μl diethylpyrocarbonate; 2) boil until volume is below 79 ml; 3) measure in graduated cylinder, bring volume to 79 ml with sterile Type I deionized water, allow to cool slightly; 4) add: 10 ml of 10×TBE, 10 ml of 30% Acrylamide/1.5% bis acrylamide, 1 ml of 10% SDS, 0.3 ml of 10% ammonium persulfate; and 30 μl TEMED; and 5) gently mix and pour the gel immediately. After the gels have polymerized (20 min at 56° C.), they are stored overnight in running buffer prior to use.

The gels are run at a constant temperature in a circulating buffer system. Since the gels are run for extended periods (17 to 21 hr) the circulation of the running buffer is critical. The gels are run at temperatures ranging from 26° C. to 40° C., and at either 230 or 240 volts (constant voltage) for 17 to 24 hr. The following are general guidelines for genotyping cold-adapted influenza vaccines: Type A: 30° C. and 37° C. (two gels run) at 230 volts for 17 hr. Type B: 26° C. and 36° C. (two gels run) at 240 volts for 21 hr.

After gels are run they are enhanced in salicylic acid for 45 min and then dried. The dried gels are placed in cassettes with X-ray film at −70° C. and exposed for 24 to 72 hr. The film is developed and genotypes are read.

Ferret Reactogenicity Testing

Media and Materials. The following media and materials are used: a) 2× Eagle's—500 ml HBSS (M.A. Bioproducts 10-508); 10 ml BME amino acids (GIBCO 320-1051); 10 ml BME vitamins (GIBCO 320-1040); 10 ml L-glutamine (GIBCO 320-5030); and 0.5 ml gentamicin sulfate 50 mg/ml (M.A. Bioproducts 17-518) adjust pH to 7.0 using 0.5N NaOH. b) sodium pentobarbital—sodium pentobarbital injection (65 mg/ml) Anthony Products Co.; c) alundum—60 mesh norton alundum "RR" (Fisher Scientific Co. A-620); sterilize by autoclaving at 250° C. for 15 min, dry cycle. Ferrets—8 to 10-week old ferrets, male, castrated, and vaccinated against distemper (Marshall Research Animals). If the ferrets are not barrier-raised, they may have had an influenza infection during the influenza season. The animals will thus need to be treated with Penicillin G (30,000 units/day) for 7 days prior to use. (Durapen™ combination antibiotic (Vedco); and Penicillin G Benzathine and Penicillin G Procaine, 300,000 units/ml.) Miscellaneous—sterile instruments; sterile scalpel; diethyl ether for anesthesia; lysol; sterile Petri dishes; sterile mortar and pestle; and digital thermometer Model 8110-20 (Cole Parmer Instrument Company).

Protocol. The following protocol is used:

Day 1: 1) Dilute the stock virus $10^{-1}$ in 2× Eagle's; 2) lightly anesthetize the ferret with diethyl ether. Inoculate ferret intranasally with 1 ml of the $10^{-1}$ dilution of stock virus (0.5 ml in each nostril); 3) determine the $EID_{50}$/ml (Egg Infectious Dose—50%/ml) titer of the inoculum; serially dilute the inoculum in 2×Eagle's; inoculate 9-11 day old embryonated chicken eggs with dilutions $10^{-5}$ through $10^{-8}$, four eggs per dilution (0.1 ml per egg); incubate the eggs at 33° C. to 35° C. for 72 hr; after 72 hr cool the eggs for several hr at 4° C.; remove 1 ml of allantoic fluid from each egg and place in individual Kahn tubes; add 0.5 ml of 0.5% chicken red blood cells to each tube and mix; allow the blood to precipitate for 45 min and determine which tubes are positive for hemagglutinin activity. Calculate the $EID_{50}$ titer using the Reed-Meunch method; and 4) take rectal temperatures twice a day for 3 days.

Day 3: 1) The ferret is euthanized via heart puncture with sodium pentobarbital (130 mg/ferret); 2) place ferret on its back and clamp feet to immobilize; 3) wash abdomen with Lysol®; 4) using sterile forceps and scalpel make a 4-5 inch incision lengthwise down the sternum and pull skin back; 5) with new set of sterile forceps and scissors cut the ribs to make an opening large enough to remove the left lower lobe of lung; remove and place in a sterile Petri dish; 6) cut a section of the left lobe into small pieces and place into a freezable storage tube; 7) turn ferret over and wash head with Lysol®; 8) with scalpel and forceps remove the skin from the end of nose to below eyes; 9) cut off snout at the base of the septum; 10) cut the nasal bone on both sides of the septum—approximately ⅛ to ¼ inch with sterile bone cutter; 11) scrape out the turbinate using sterile currette and place in freezable storage tube; 12) weigh the tubes containing the lung and turbinate samples and record; 13) place the tissues in sterile mortars and weigh the empty tube. The difference in the weight is the weight of tissues; 14) add sterile alundum to the mortars and grind (homogenize) the tissues with a sterile pestle; 15) dilute tissue with 2× Eagle's to make 10% weight/volume suspension; 16) centrifuge the homogenate at 500×g for 10 min at 4° C.; 17) remove supernatant and freeze at −70° C.; 18) thaw the supernatant and determine the $EID_{50}$/ml as previously described. A general range for inoculation is: 3-day turbinate dilutions of $10^{-3}$ to $10^{-6}$ dilution, 3-day lung dilutions of $10^{-1}$ to $10^{-4}$ dilution; and 19) harvest the eggs from the inoculum and calculate the $EID_{50}$ as described previously.

Day 6: 1) Harvest the eggs from the 3-day turbinate and lung and calculate the $EID_{50}$'s as described previously.

Ferret Serum Collection

Materials. The following materials are used: B-D Vacutainer brand Winged Collection Set, 19 gauge needle, with luer; adapter and 12-inch tubing (B-D #4919); B-D Vacutainer brand needle holder for 16 mm tube (B-D #364888); B-D Vacutainer brand SST (Serum Separation Tube) 16×125 mm (B-D #6512); diethyl ether for anesthesia; and 70% ethanol.

Procedure. The following protocol is employed: 1) assemble collection set and needle holder; 2) lightly anesthetize the ferret with diethyl ether; 3) place ferret on its back and hold firmly; 4) wash chest with 70% ethanol; 5) palpate for heartbeat (left side, between 3rd and 4th rib from base of sternum; 6) insert needle into ferret's heart; when blood is seen entering the collection tube insert the SST tube onto needle; collect the desired amount for test procedures; 3-4 ml of blood will provide 1-2 ml of serum; 7) allow blood to completely clot at room temperature (approx. 30 min); 8) centrifuge tube at room temperature for 10 min at 1000-1300 g; and 9) collect serum, aliquot, and store at −70° C. Note that ferret serum should be treated using the trypsin-periodate method described below to remove nonspecific inhibitors prior to use.

Trypsin-Periodate Treatment for Ferret Sera

Materials. The following materials are used: a) phosphate buffer for trypsin; Solution A consists of $NaH_2PO_4.H_20$ (MW 138.01); 6.99 g $NaH_2PO4.H_20$; and 500 ml sterile Type I deionized water. Solution B consists of Na2HPO4 (MW 141.97); 7.1 g $Na_2HPO_4$; and 500 ml sterile Type I deionized water; b) working buffer consists of 1 volume of Solution A+31 volumes of Solution B (pH=8.2); c) Trypsin solution—0.4 g trypsin 1:250 (DIFCO 0152-13-1); and 100 ml phosphate buffer. Solution is stable when frozen at −20° C.; d) potassium periodate solution—0.255 g $KIO_4$ (MW 230.02); and 100 ml sterile Type I deionized water. Store in a light-proof bottle. Stable at room temperature for one month; e) 1% glycerol saline—1 ml glycerol; and 99 ml phosphate buffered saline (PBS) (M.A. Bioproducts 17-516).

Sera Treatment—1) mix 1 volume of serum+1 volume of trypsin solution; 2) heat immediately to 56° C. for 30 min; 3) cool to room temperature; 4) add 3 volumes of potassium periodate solution; 5) mix and incubate at room temperature for 15 min; and 6) add 3 volumes of 1% glycerol saline; serum is a 1:8 dilution and is ready to use for HI tests. If serum is going to be used for making reassortants it needs to be filter sterilized through a 0.221μ filter (low protein binding).

Hemagglutinin Inhibition Screening of Ferret Sera

Procedure. The ferrets are screened prior to use to certify that they are immunologically naive to influenza virus. Follow the hemagglutinin inhibition procedure as described in: "Concepts and Procedures for Laboratory-Based Influenza Surveillance", U.S. Department of Health and Human Services, Public Health Service, Centers for Disease Control (July 1982).

Ferrets are screened for exposure to influenza strains which have circulated in the last 12 months and/or strains which are presently circulating. The ferret sera should always be screened against a Type A H1N1 strain, a Type A H3N2 strain, and the most recent Type B strain.

SPECIFIC EXAMPLE 6

Clinical Results

Since 1976 the clinical development of the cold-adapted influenza virus vaccines has included the testing of multiple reassortant vaccines in over 20,000 people between the ages of 4 months to over 80 years. A summary of the cold-adapted influenza vaccines tested in the United States is set forth in Table 10. These studies have cornsistently demonstrated the ca vaccines to be genetically stable, and rion-transmissible in all populations tested. More recently, studies on the ca vaccine have focused in three broad areas: 1) evaluating the range and extent of the immunologic response; 2) determining the protective efficacy of the vaccine in the overall population as well as in targeted subsets; and 3) evaluating the immunologic and efficacious consequences of administrating divalent/trivalent ca influenza virus vaccines.

The following is a standard procedure for the clinical evaluation of and collection of specimens from volunteers in attenuated influenza vaccine studies.

A. Clinical Observations

Two observers should independently evaluate the clinical status of the volunteer. Optimally, each evaluator should see the patient daily before and during the first four days after virus administration.

Categories of Illness. 1) Fever—Oral temperature of greater than 37.7° C. (100° F.) will be considered a febrile reaction. Any temperature should be confirmed using a second thermometer, 5 minutes after the first measurement. If positive, measurement should be repeated every four hours. 2) Systemic Illness—Occurrence of myalgias, and/or chills and sweats are required for the assignment of systemic illness to a volunteer. Additional information should be gathered concerning feverishness, malaise, headache, anorexia, etc. It is recognized that these observations are subjective. 3) Pharyngitis—Sore, painful throat observed in 2 consecutive days. All volunteers reporting this symptom should receive appropriate bacterial diagnostic workups. 4) Rhinitis—Occurrence of rhinorrhea on two consecutive days. Presence of nasal obstruction and sneezing are supporting of this illness designation. 5) Lower Respiratory Tract Illness—A symptom complex consisting of substernal pain, cough (paroxysmal), sputum production.

Administration of Virus to Volunteers. An appropriate therapeutic dose, ie. 0.25 ml, is administered to each nostril of a supine volunteer who should remain supine for at least ten minutes. Preferably the vaccine should be administered to all volunteers by the same individual.

B. Clinical Specimens

1) For virus isolation, nasal wash (NW) consisting of 5 ml of veal infusion broth, containing no antibiotics, is administered to each nostril. 0.25 ml of this wash should be inoculated into each of 4 tubes of an appropriate tissue culture (RMK or MDCK). The remaining NW should be divided into three aliquots and stored at −7° C. 2) At least 20 ml of blood should be collected before immunization and at 21 to 28 days after immunization. An alternative method is the use of a nasopharyngeal swab and 2 ml of veal infusion broth with antibiotics for viral isolation. 3) Nasal wash for local antibody determination—5 ml of a physiologic salt solution is instilled into each nostril and collected. A second specimen is collected at least 30 minutes later. These two collections are pooled. The timing of the pre- and post-immunization collections is the same as for serum. The specimens should be concentrated approximately 10 fold.

C. Determination of Serum and Nasal Wash Antibody Levels

The tests and antigens for screening the volunteers and evaluating serum and nasal wash antibodies is as follows: Screening of volunteers—All volunteers should be HI and NI negative to the influenza subtypes that are being evaluated in the study. The antigens to be used are the A/Denver/57 and A/USSR/90/77 (Parke Davis vaccine). NI antibody determinations are performed on the specimens.

TABLE 10

Summary of Cold-adapted (ca) Influenza Vaccines Tested In the United States

| ca Vaccine | | Results: Attenuated | Antigenic | Genetic Stability | Efficacy |
|---|---|---|---|---|---|
| B/Hong Kong/73, CR-7 | Adults | + | + | + | + |
| | Children | ND | ND | ND | ND |
| A/Victoria/75, (H3N2) CR-22 | Adults | + | + | + | + |
| | Children | + | + | + | + |
| A/Alaska/77, (H3N2) CR-29 | Adults | + | + | + | + |
| | Children | + | + | + | + |
| A/Hong Kong/77, (H1N1) CR-35 | Adults | + | + | + | ± |
| | Children | + | + | + | ± |
| A/California/78, (H1N1) CR-37 | Adults | + | + | + | + |
| | Children | + | + | + | + |
| A/Washington/80, (H3N2) CR-48 | Adults | + | + | + | + |
| | Children | + | + | + | + |
| A/Korea/82, (H3N2) CR-59 | Adults | + | + | + | ± |
| | Children | + | + | + | ± |
| A/Dunedin/83, (H1N1) CR-64 | Adults | + | + | + | ± |
| | Children | + | + | + | ND |
| B/Texas/84, CRB-87 | Adults | + | + | + | + |
| | Children | + | + | + | ND |
| A/Bethesda/85, (H3N2) CR-90 | Adults | + | + | + | + |
| | Children | + | + | + | + |
| A/Texas/85, (H1N1) CR-98 | Adults | + | + | + | + |
| | Children | + | + | + | + |
| A/Kawasaki/86, (H1N1) CR-125 | Adults | + | + | + | + |
| | Children | + | + | + | + |
| B/Ann Arbor/86, CRB-117 | Adults | + | + | + | ND |
| | Children | + | + | + | ND |
| A/Los Angeles/87, (H3N2) CR-149 | Adults | + | + | + | + |
| | Children | + | + | + | + |
| B/Yamagata/88 | Adults | + | + | + | ND |
| | Children | ND | ND | ND | ND |

ND = not done

SPECIFIC EXAMPLE 7

Simultaneous Adminstration with Other Vaccines

One of the pressing needs for the development of the ca vaccine is to determine if protective immunogenicity is compromised when a bivalent or trivalent preparation is administered, and if so, if this interference can be overcome. Previous studies comparing monovalent and bivalent ca A vaccine (H1N1 and H3N2) administration in seronegative children demonstrated that the frequency of seroconversion was higher when vaccines were administered individually rather than simultaneously. Wright, P. F. et al., *J. Infect. Dis.* 146: 71-79 (1982); Wright, P. F. et al., *Vaccine* 3:305-308 (1985). Using simultaneous administration of $10^5$ tissue culture infectious doses ($TCID_{50}$) of each of three ca vaccines (H1N1, H3N2 and B), (less than 10 human infectious doses {$HID_{50}$}/vaccine component) Belshe and coworkers evaluated the question of trivalent vaccine interference in infants. Belshe, R. B. et al., *J. Infect Dis.* 165:727-732 (1992). Among the seropositive children, few children shed vaccine virus and few increases in antibody to any of the three vaccine components was observed. Within the triply seronegative infant group, 47% shed all three ca vaccine viruses and 75% of these infants had a significant antibody rise to all three ca vaccine components. Of those that showed either shedding or antibody rise to two of the three ca vaccine components, no strain pair preference was observed. These results suggest that in infants and children not previously exposed to influenza, it may be possible to identify an appropriate dose (e.g. 100 $HID_{50}$/vaccine component) which could stimulate antibody response to all three components.

The question of serological and/or protective interference in the adult population has been raised in relationship to the bivalent ca A vaccine efficacy studies. Edwards, K. M. et al. "A Randomized Controlled Trial of Cold-Adapted and Inactivated Vaccines for the Prevention of Influenza A Disease" (submitted for publication); Clover, R. D. et al., *J. Infect. Dis.* 163:300-304 (1991). Trivalent vaccine administration has recently been evaluated in adults having low antibody levels to all three components. In the adult population significant interference with virus shedding and a trend toward lower antibody responses, particularly against the ca B vaccine component, was observed in vaccinees receiving the trivalent ca vaccine when compared to either a bivalent A or monovalent B controls. Keitel, W. A. et al., "Trivalent Live Cold-adapted Influenza Virus Vaccine: Evidence for Virus Interference in Susceptible Adults." Manuscript in preparation). These results suggest that appropriate formulation may need to be developed to enhance the maximal response of each influenza vaccine component. Thus, the present invention contemplates the use of such appropriate formulations which may be made by those skilled in the art.

SPECIFIC EXAMPLE 8

Other Genetically-Engineered Vaccines

More recent techniques, such as recombinant DNA cloning and the transfection of in vitro mutagenized gene segments can be employed for the production of live virus vaccines. For example, the gene coding for the HA protein has been cloned into vaccinia virus and is expressed on the virus surface. Attenuated recombinant vaccinia viruses have been shown to provide protection to homologous wt virus challenge in hamsters. Smith, G. L. et al., *PNAS* (*USA*) 80:7155-7159 (1983). If necessary, other influenza genes cloned into the vaccinia virus carrier are also employed at the same time. Alternatively, master strains are comprised of a number of selected genes with specific mutations, including deletions to confer stability. Chanock, R. M. et al., *Prospects for Stabilization of Attenuation* in "The Molecular Virology and Epidemiology of Influenza", Stuart-Harris et al. (eds.) Academic Press, NY (1984). CR43-3 virus is a cold reassortant whose genome contains an NS gene with a deletion in the NS1 protein coding region and is restricted for growth in both Madin-Darby canine kidney cells and in ferrets. Buonagurio, D. A. et al., *J. Virol.* 49:418425 (1984); Maassab, H. F. et al., *Virology* 130: 342-350 (1983). Because the remaining non-(HA and NA) genes are derived from the ca master strain A/Ann Arbor/6/60 virus, CR43-3 may have the potential to be used as a new master strain.

Deletions are also generated through site specific mutagenesis in recombinant cDNA clones. The ability to introduce RNA transcripts of specifically mutagenized cDNA clones into the influenza viruses as stable parts of the genome has opened new areas of research into vaccine development. Enami, M. et al., *J. Virol.* 65:2711-2713 (1991); Enami, M. et al., *PNAS* (*USA*) 87:3802-3805 (1990). It is now thus possible to produce "ailor-made" influenza vaccines engineered for specific purposes in accordance with the principles of the present invention.

In particular, the ca A/Leningrad/47 virus is used as a model for the introduction of mutations. Klimov, A. I. et al., *Virol.* 186:795-797 (1992). The ca A/Leningrad/47 virus has been chosen as a model because 1) differences between the wt A/Leningrad, A/Leningrad/17, and A/Leningrad/47 viruses are published knowledge and they are one of the few H2N2 viruses sequenced and listed in GenBank; 2) these differences will not be lethal mutations; 3) these differences probably will not interfere with growth; 4) one or several of them may introduce another temperature sensitive (ts) lesion into the ca A/AA/6/60 genome. Since the PA, M, and NS genes of the ca and the wt 2(3) A/AA/6/60 viruses are identical, those three genes have been targeted for mutation. The ca A/Leningrad/47 PA gene has three differences from the wt A/Leningrad virus; the M gene has two differences and a ts lesion; and the NS gene has one difference and a ts lesion. The ca A/AA/6/60 virus has the nucleotides at these positions of the wt A/Leningrad virus, with the exception of 969 in the matrix gene. Because a helper virus is available which will facilitate the selection of clones bearing a mutated NS gene, that gene is mutated first and rescued using the techniques of reverse genetics known to those in the art. Nucleotide 798 of the ca NS gene will be mutated from guanine to adenine, coding for methionine to isoleucine in NS2. Although this nucleotide has not been definitively identified as responsible for the ts lesion residing on the NS gene of ca Leningrad, it is the only difference from the wt Leningrad sequence. After the mutation has been successfully rescued, the mutated ca A/AA/6/60 virus is evaluated for the retention of the ca and ts markers and for retention of antigenicity, as described above.

SPECIFIC EXAMPLE 9

Viral Vectors

The viruses of the present invention are also useful as vectors for foreign proteins. For example, the use of either the HA or NA genes as vectors for foreign viral proteins has been suggested. Li, S. et al. *J. Virol.* 66(1):399-404 (1992) and Castrucci, M. A. et al., *J. Virol.* 67(2):759-764 (1993). H3N2 amino acids and H2N2 amino acids were introduced into the HA of an H1N1 virus, thus constructing a chimeric HA influenza molecule. Li, S. et al., *J. Virol.* 66(1):399-404 (1992). Although foreign viral amino acids or additional amino acids were not introduced into the $HA_1$ a chimeric HA can be constructed with antigenic sites important for the current H1N1 and current H3N2 viruses in the same virus. Thus, one virus with a chimeric HA could be given instead of giving a divalent vaccine.

It has been shown that insertion of 28 amino acids into the neuraminidase stalk does not interfere with growth of the virus in eggs; in fact, the longer the stalk, the better it grew. This suggests use of the influenza virus as a vaccine vector to immunize against other unrelated infectious agents. Since the NA is a glycoprotein on the surface of the virus and is one of the two major antigenic proteins for the influenza virus, it may be an excellent site for presentation of a foreign antigenic epitope. Likewise, the ca A/AA/6/60 virus may also be used as a vaccine vector, Castrucci, M. A. et al., Abstract 15-4;

ASV 12th Annual Meeting, Jul. 10-14 (1993), i.e. a vector for the human immunodeficiency virus, HIV.

SPECIFIC EXAMPLE 10

Clinical Studies

As previously stated, many clinical studies have been performed using cold-adapted vaccines. In this study, a live attenuated trivalent combination of vaccines was evaluated to see if a single intranasal administration of $\leq 10$ TCID$_{50}$ of each vaccine virus could successfully immunize triply seronegative children. A detailed description of this study is also set forth in Beishe, R. B. et al., *J. Infect. Dis.* 165:727-732 (1992).

Materials and Methods. The cold-recombinant (CR) influenza A vaccines and the CR influenza B vaccine included in the trivalent vaccine were derived from cold-adapted parent strains of influenza using methods previously described. Maassab, H. F., *J. Immunol.* 102:728-732 (1969); Cox, N. J. et al., *Virol.* 97:190-194 (1979); Maassab, H. F. et al., *Virol.* 130:342-350 (1983); Maassab, H. F. et al., *J. Infect Dis.* 146:780-790 (1982); Donabedian, A. M. et al., *Microb. Pathog.* 3:97-108 (1987). Influenza A/Kawasaki/9/86 (H1N1) and influenza A/Korea/1/82 (H3N2) were derived from the cold-adapted influenza A/Ann Arbor/6/60 parent virus, while influenza B/Texas/1/84 was produced from influenza B/Ann Arbor/1/66 cold-adapted parent virus. The vaccine viruses, designated CR125 (H1N1), CR59 (H3N2), and CRB-87, possessed the six internal genes of their parent cold-adapted virus, A/Ann Arbor/6/60 or B/Ann Arbor/1/66, and the hemagglutinin and neuraminidase genes of their respective wild type strains. Vaccinees received 0.5 ml of the cold-adapted trivalent influenza vaccine consisting of a mixture of CR125 and CRB-87, each diluted 1:100, and CR59 diluted 1:50. To ensure that an equal titer of each viral strain was incorporated into the trivalent vaccine, each of the three vaccines was diluted separately on the day of vaccination. Subsequently, an equal volume of each was pooled to make the vaccine for administration to the volunteers. Assays were done on an aliquot of each component of the trivalent vaccine to assess the titer of each of the influenza strains incorporated into the vaccine. Titering of vaccine on each of six vaccination dates revealed H1 vaccine to contain a mean of $10^{5.0}$ TCID$_{50}$, H3 vaccine to contain a mean of $10^{4.9}$ TCID$_{50}$, and B vaccine to contain a mean of $10^{5.5}$ TCID$_{50}$ per half mil of a vaccine stock before being combined into trivalent vaccine. Thus the final concentration was one-third of the above (H1, $10^{4.5}$; H3, $10^{4.4}$; and B, $10^{5.0}$ TCID$_{50}$/0.5-ml dose of vaccine).

Vaccination and Clinical Observations. Healthy infants and children aged 6 months to 13 years were recruited to join the study. Volunteers were randomized to receive vaccine or vaccine diluent as placebo in a double-blinded way. One of every three to four children received placebo.

Children were placed in a supine position and 0.5 ml of vaccine was instilled into the nose as previously described. Beishe, R. B. et al. *J. Infect. Dis.* 149:735-740 (1984); Anderson, E. L. et al., *J. Clin. Microbiol.* 27: 909-914 (1989). After vaccination, the children were observed in their homes for 11 days by the vaccine center nursing staff with daily sampling by nasopharyngeal swabbing for isolation of influenza virus. Serum for antibody determinations was obtained on days 0 and 28-31. One post-vaccine serum sample was obtained on day 60.

Potential adverse reactions were defined as: (1) fever, rectal temperature>38.3° C. (infants and young children) or oral temperature>37.8° C. (older children); (2) cough, two or more episodes noted during examination visits on 2 consecutive days; (3) rhinorrhea, fluid or mucus exiting nostrils on 2 consecutive days; (4) wheeze, sustained musical sound during expiration and confirmed by a physician investigator; (5) otitis media, red, immovable ear drum diagnosed by a physician using pneumootoscopy; (6) rhonchi, continuous low-pitched sound heard by auscultation of lung fields; (7) rales, discontinuous, interrupted explosive sounds, fine or coarse crackles heard by auscultation of lung fields and confirmed by a physician; and (8) pneumonia, a new alveolar consolidation seen radiographically.

Laboratory Studies. Serologic tests for antibody to each vaccine strain were assayed by hemagglutination inhibition (HAI) and ELISA. HAI assays used homologous, tissue-culture-grown antigen for each of the vaccine strains in the trivalent vaccine as previously described. World Health Organization, "The hemagglutination inhibition test for influenza virus." U.S. Department of Health, Education and Welfare Procedure Manual, Atlanta:Center for Disease Control (1975). Prevaccination immune status of the vaccinees was based on HAI titers; a titer<1:4 was considered seronegative. Purified hemagglutinin from heterologous influenza strains, consisting of influenza Taiwan (A/H1N1), influenza Shanghai (A/H3N2), and influenza B/Yamagata (Connaught Laboratories, Swiftwater, Pa.), was used for the ELISA. Briefly, microtiter plates (Dynatech, Chantilly, Va.) were coated with antigen (1 µg/ml) overnight at 4° C. The remaining steps of the ELISA procedure were done the next day as follows: (1) antigen was removed but the plates were not washed; (2) plates were blocked with 0.1% bovine serum albumin in PBS and washed with PBS-Tween; (3) four-fold dilutions of test samples were added to the plates and the plates were incubated at 37° C. for 2 hr; (4) after plates were washed with PBS-Tween, goat anti-human IgG was added for a 2 hr incubation at 37° C.; and (5) plates were washed, developed using a phosphatase substrate kit (Kirkegaard & Perry, Gaithersburg, Md.), and read in a microtiter plate reader after 30 min for IgG and 90 min for IgA. An antibody response was defined as a seroconversion by HAI or ELISA (<1:4 to $\geq$1:8 by HAI; <1:20 to $\geq$1:20 by ELISA) or as a four-fold increase in titer.

Viral shedding was monitored by isolation in cell-culture tubes of primary rhesus monkey kidney (RhMK) cells as previously described. Belshe, R. B. et al., *J. Infect. Dis.* 150: 834-840 (1984). Cell cultures were incubated at 32° C. for 14 days. Hemadsorption of monolayers with 0.4% guinea pig erythrocytes was done on days 5, 9 and 14. In addition, some specimens were inoculated into RhMK tubes containing combinations of polyvalent antiserum specific for two of the three subtypes to permit selective growth of the third subtype. Viral subtype was identified by HAI or by indirect immunofluorescence using monoclonal antibodies (see below). Harmon, N. W. et al., *Influenza Viruses* in "Diagnostic Procedures for Viral Rickettsial and Chlamydial Infections." Schmidt, N. J. et al. (eds.) Washington, D.C.: American Public Health Association 651-653 (1989); Riggs, R. L., *Immunofluorescence Staining* in "Diagnostic Procedures for Viral Rickeftsial and Chlamydial Infections." Schmidt, N. J. et al. (eds.) Washington, D.C.: American Public Health Association 651-653 (1989).

To enumerate the viral subtypes shed by each vaccinee, plaque assays were done using subtype-specific monoclonal antibodies in an immunoperoxidase-staining procedure. Confluent monolayers of RhMK cells in 24-well plates were rinsed with sterile PBS, pH 7.2, and then infected in triplicate with 0.2 ml/well of specimen. After absorption for 1 h at 33° C., each well was overlaid with L-15 medium (Whittaker M.A. Bioproducts, Walkersville, Md.) containing 1% agarose (SeaKem; FMC Bioproducts, Rockland, Me.), 200 mM L-glutamine (Whittaker M.A. Products), and 50 μg/ml gentamicin. Infected plates were incubated at 33° C. for 3 days. Subsequently, plates were fixed, the agarose overlay was removed, and the plates were stained by a modification of an immunoperoxidase procedure developed by William Gruber (Department of Pediatrics, Vanderbilt Unitersity, Nashville, Tenn.). Infected monolayers were first fixed sequentially with 80% and 100% methanol for 15 min at 4° C., and then were overlaid with 5% skim milk (Difco, Detroit) in PBS for 30 min at 37° C. After removal of the skim milk, each well was overlaid with 0.2 ml of subtype-specific monoclonal antibody diluted 1:2000 (v/v, in PBS for 1 hr at 37° C. Monoclonal antibodies designated as (B/AA/1/86 [B/M] 1/2; A/Mem/2/85 [H3 M2-7]; A/Baylor/11515/82 [H1 AB/28] were provided by Robert Webster, St. Jude Children's Research Hospital (Memphis). After two washes with 5% skim milk, 0.2 ml of peroxidase-conjugated rabbit anti-mouse antibody (1:35, Dako, Carpinteria, Calif.) was added to each well for 30 min at 37° C. Plates were washed twice with 5% skim milk after which each well was overlaid with 0.2 ml of peroxidase-conjugated swine anti-rabbit antibody (1:90; Dako) for 30 min at 37° C. After two 5% skim milk washes, each well was overlaid with 0.2 ml of AEC substrate (Dako) prepared according to manufacturer's instructions. Plates were incubated at room temperature until positive control wells showed satisfactory color development (~5 min.). Plates were washed with distilled water and read under a dissecting microscope for the presence of red-stained plaques. Uninfected wells were stained in parallel to control for background staining.

Results. The clinical and serologic response of vaccinees is summarized in Table 11. As in other trials, some background mild respiratory illness was seen in both vaccinees and controls and was more frequent among children<12 months old. There was no suggestion of influenza-like symptoms or temporal clustering to suggest that illness was related to vaccine.

The majority of triply seronegative vaccinees exhibited an antibody response to each vaccine component by HAI; fewer antibody rises to H3 and B hemagglutinins (heterologous antigens were used, see Materials and Methods) were detected by ELISA than HAI (Table 11). Of 17 triply seronegative vaccinees, 8 (47%) developed an antibody response to all three strains of the vaccine by HAI or ELISA. Mean postvaccination serum HAI titers were significantly higher for the H3 component than for the other two vaccine strains (Table 11). In contrast to seronegative children, ELISA was more sensitive than HAI at detecting antibody increases in seropositive children (Table 11). Of the 15 seropositive children, by ELISA 4 (27%) had antibody increases to H1, 4 (27%) to H3, and 5 (33%) to B hemagglutinin.

TABLE 11

Clinical and Serologic Responses After Intranasal Vaccination With Cold-Adapted Trivalent Influenza Vaccine

| Finding | Group | | |
|---|---|---|---|
| | Seronegative[b] (n = 17) | Seropositive[b] (n = 15) | Control (n = 17) |
| AGE RANGE, MONTHS | 7-23 | 10-116 | 6-60 |
| NO. WITH ILLNESS[a] | | | |
| Fever | 0 | 2 | 2 |
| Upper respiratory illness (RI) | 12[c] | 5 | 8 |
| Lower RI | 0 | 0 | 1 |
| Otitis media | 2 | 4 | 1 |

TABLE 11-continued

Clinical and Serologic Responses After Intranasal Vaccination With Cold-Adapted Trivalent Influenza Vaccine

| Finding | Group | | |
|---|---|---|---|
| | Seronegative[b] (n = 17) | Seropositive[b] (n = 15) | Control (n = 17) |
| SEROLOGIC RESPONSES TO VACCINE[d] | | | |
| H1N1/Kawasaki | | | |
| Before vaccination | <2 | 5.3 | 1.2 |
| After vaccination | 2.7[e,f] | 5.3 | 1.2 |
| No. with HAI response | 10 | 0 | 0 |
| No. with ELISA response | 10 | 4 | NT |
| H3N2/Korea | | | |
| Before vaccination | <2 | 5.5 | 1 |
| After vaccination | 4.1[e,f] | 6.1 | 1.2 |
| No. with HAI response | 12 | 2 | 0 |
| No. with ELISA response | 9 | 4 | NT |
| B/Texas | | | |
| Before vaccination | <2 | 3.4 | 1 |
| After vaccination | 2.5[f] | 4.2 | 1.2 |
| No. with HAI response | 8 | 4 | 0 |
| No. with ELISA response | 6 | 5 | NT |

HAI = hemagglutination inhibition assay; NT = not tested.

[a]Fever, rectal temperature >38.30° C.; upper RI, ≧2 consecutive days with rhinnorhea or pharyngitis; lower RI, wheezing or pneumonia; otitis media was diagnosed by a pediatrician.

[b]Seronegative (HAI < 1:4) or seropositive (HAI ≧ 1:4) to all three strains of virus. Two children were vaccinated and were doubly or singly seronegative; they are not included in the analysis.

[c]Significantly more rhinorrhea than seropositive vaccinees (12 of 17 vs. 5 of 17, x2 = 5.8; P < 0.05) but not significant when compared to controls (Fisher's exact test, P = 0.14).

[d]Antibody response defined as four-fold increase; for negative volunteers a titer rise from <1:4 to ≧1:8 by HAI or ≧1:20 by ELISA.

[e]P < 0.03, Student's t test.

[f]P < 0.02, Student's t test.

As shown in Table 12, viral shedding was observed in most seronegative volunteers and occurred significantly more often in seronegative recipients than in seropositive recipients (P≦0.02 for all comparisons between seronegatives and seropositives stratified by viral subtype). Sixteen of seventeen seronegative vaccinees shed at least one strain of virus; one vaccinee who failed to shed vaccine was infected with coxsackie B2 virus. Shedding of H1 and H3 was first observed 1 day after vaccination while type B shedding began on day 2. The number of children shedding vaccine virus peaked on day 4 for H1, on day 6 for H3, and day 5 for B.

TABLE 12

Viral Shedding After Intranasal Vaccination With Cold-Adapted Trivalent Influenza Vaccine

| Vaccine | Subjects | |
|---|---|---|
| | Seronegative[a] | Seropositive[a] |
| H1N1/Kawasaki | | |
| No. shedding/no, infected with vaccine virus[b] | 10/12 | 2/5 |
| Mean duration (days) | 7.8 | 9 |
| Mean peak titer (pfu/ml) | 12 | NT |
| H3N2/Korea | | |
| No. shedding/no, infected with vaccine virus[b] | 13/13 | 2/4 |
| Mean duration (days) | 8.8 | 6.5 |
| Mean peak titer (pfu/ml) | 74 | NT |
| B/Texas | | |
| No. shedding/no. infected with vaccine virus[b] | 11/13 | 2/6 |

TABLE 12-continued

Viral Shedding After Intranasal Vaccination With Cold-Adapted Trivalent Influenza Vaccine

| | Subjects | |
|---|---|---|
| Vaccine | Seronegative[a] | Seropositive[a] |
| Mean duration (days) | 9.4 | 3.5 |
| Mean peak titer (pfu/ml) | 41 | NT |

Eleven seronegative subjects were infected with all three vaccine viruses; NT = not tested.
[a]Hemagglutination inhibition assay seronegative and seropositive values, respectively, were <1:4 or ≧1:4.
[b]Indicated by viral shedding or antibody response by hemagglutination inhibition assay or by ELISA.

Plaque assays to quantitate each subtype shed by seronegative vaccinees were done on samples from 15 of 17 volunteers (Table 11). The minimum titer detectable by plaque assay was 5 pfu/ml. Specimens positive by tube culture but negative by plaque assay were considered to have a titer<5 pfu/ml. The highest mean viral titer was observed for H3 (74 pfu/ml), which was significantly higher than that of H1 (12 pfu/ml; p<0.02, Student's t test). The highest titers of H1 were shed early, on days 3 and 4 after vaccination. Peak H3 and B titers were found on days 7 and 4 after vaccination, respectively.

Overall, 12 (71%), 13 (76%), and 13 (76%) of seronegative children were infected by H1N1, H3N2, or B vaccine viruses, respectively, as indicated by viral shedding or by HAI or ELISA antibody responses (Table 12). Eleven (65%) were infected by all three strains. Among seropositive children five (33%), four (27%), and six (40%) were infected by H1N1, H3N2, or B vaccine viral strains, respectively, as indicated by viral shedding or by HAI or ELISA antibody responses. None of the seropositive children was infected by all three vaccine viruses.

Those skilled in the art can now appreciate from the foregoing description that the broad teachings of the present invention can be implemented in a variety of forms. Therefore, while this invention has been described in connection with particular examples thereof, the true scope of the invention should not be so limited since other modifications will become apparent to the skilled practitioner upon a study of the drawings, specification and following claims.

All applications and publications cited herein are incorporated by reference.

We claim:

1. A reassortant influenza virus comprising:

first and second polynucleotides encoding surface proteins HA and NA, respectively, of at least one wild type influenza virus; and third, fourth, fifth, six, seventh, eighth polynucleotides encoding six internal proteins of a cold-adapted influenza virus, wherein the third polynucleotide encodes influenza PB1, wherein the fourth polynucleotide encodes influenza PB2, wherein the fifth polynucleotide encodes influenza PA, wherein the sixth polynucleotide encodes influenza NP, wherein the seventh polynucleotide encodes influenza M, and wherein the eighth polynucleotide encodes influenza NS and wherein the fifth polynucleotide comprises the nucleotide sequence of SEQ ID NO:11 and the fourth polynucleotide comprises the nucleotide sequence of SEQ ID NO: 15.

2. The reassortant influenza virus of claim 1 wherein the third polynucleotide comprises the nucleotide sequence of SEQ ID NO:13, wherein the fourth polynucleotide comprises the nucleotide sequence of SEQ ID NO:15, wherein the sixth polynucleotide comprises the nucleotide sequence of SEQ ID NO:9, wherein the seventh polynucleotide comprises the nucleotide sequence of SEQ ID NO:5 or SEQ ID NO:7, and wherein the eighth polynucleotide comprises the nucleotide sequence of SEQ ID NO:1.

3. A vaccine comprising the influenza virus of claim 1 or 2.

4. The vaccine of claim 3 which is formulated for intranasal delivery.

5. The vaccine of claim 3, further comprising an influenza B virus.

* * * * *

UNITED STATES PATENT AND TRADEMARK OFFICE

CERTIFICATE OF CORRECTION

PATENT NO. : 8,282,937 B2
APPLICATION NO. : 11/690498
DATED : October 9, 2012
INVENTOR(S) : Maassab et al.

It is certified that error appears in the above-identified patent and that said Letters Patent is hereby corrected as shown below:

On the Title Page, in item (75), under "Inventors", in Column 1, Line 1, delete "Hunein" and insert -- Hunein F. --, therefor.

On the Title Page:

The first or sole Notice should read --

Subject to any disclaimer, the term of this patent is extended or adjusted under 35 U.S.C. 154(b) by 854 days.

On the Title Page, delete item "(60)" and insert item -- (62) --, therefor.

Signed and Sealed this
Ninth Day of December, 2014

Michelle K. Lee

Michelle K. Lee
*Deputy Director of the United States Patent and Trademark Office*

SEQUENCE LISTING

```
(1) GENERAL INFORMATION:

   (iii) NUMBER OF SEQUENCES: 40


(2) INFORMATION FOR SEQ ID NO: 1:

     (i) SEQUENCE CHARACTERISTICS:
          (A) LENGTH: 890 base pairs
          (B) TYPE: nucleic acid
          (C) STRANDEDNESS: single
          (D) TOPOLOGY: linear

    (ii) MOLECULE TYPE: RNA (genomic)

    (vi) ORIGINAL SOURCE:
          (A) ORGANISM: Influenza virus
          (B) STRAIN: cold-adapted "Master Strain" A/Ann Arbor/6/60 7PI
               (H2N2)

   (vii) IMMEDIATE SOURCE:
          (B) CLONE: NS

    (ix) FEATURE:
          (A) NAME/KEY: exon
          (B) LOCATION: 27..56
          (D) OTHER INFORMATION: /product= "nonstructural protein
               NS2"
               /gene= "NS"
               /note= "nonstructural protein NS2"
               /citation= ([1][2])

    (ix) FEATURE:
          (A) NAME/KEY: conflict
          (B) LOCATION: replace(483, "a")
          (D) OTHER INFORMATION: /note= "a in ca "master" strain and in
               wt2(3)"
               /citation= ([1][2])

    (ix) FEATURE:
          (A) NAME/KEY: exon
          (B) LOCATION: 529..861
          (D) OTHER INFORMATION: /product= "nonstructural protein
               NS2"
               /gene= "NS"
               /note= "nonstructural protein NS2"
               /citation= ([1][2])
```

(ix) FEATURE:
(A) NAME/KEY: conflict
(B) LOCATION: replace(813, "g")
(D) OTHER INFORMATION: /note= "g in ca "master" strain and in wt2(3)"
/citation= ([1][2])

(ix) FEATURE:
(A) NAME/KEY: CDS
(B) LOCATION: join(27..56, 529..861)
(D) OTHER INFORMATION: /product= "nonstructural protein NS2"
/gene= "NS"
/note= "nonstructural protein NS2"
/citation= ([1][2])

(ix) FEATURE:
(A) NAME/KEY: CDS
(B) LOCATION: 27..677
(D) OTHER INFORMATION: /product= "nonstructural protein NS1"
/gene= "NS"
/note= "nonstructural protein NS1"
/citation= ([1][2])

(x) PUBLICATION INFORMATION:
(A) AUTHORS: Herlocher, M L
Maassab, H F
Webster, R G
(B) TITLE: Molecular and biological changes in the cold adapted master strain A/AA/6/60 (H2N2) influenza virus
(C) JOURNAL: Proceedings of the National Academy of Sciences of the USA
(G) DATE: 1993
(K) RELEVANT RESIDUES IN SEQ ID NO:1: FROM 1 TO 890

(x) PUBLICATION INFORMATION:
(A) AUTHORS: Cox, N J
Kitame, F
Kendal, A P
Maassab, H F
Naeve, C
(B) TITLE: Identification of sequence changes in the cold-adapted live attenuated influenza vaccine strain, A/Ann Arbor/6/60(H2N2)
(C) JOURNAL: Virology
(D) VOLUME: 167
(F) PAGES: 554-567
(G) DATE: 1988
(K) RELEVANT RESIDUES IN SEQ ID NO:1: FROM 1 TO 890

(xi) SEQUENCE DESCRIPTION: SEQ ID NO: 1:

```
AGCAAAAGCA GGGUGACAAA GACAUA AUG GAU CCU AAC ACU GUG UCA AGC UUU      53
                             Met Asp Pro Asn Thr Val Ser Ser Phe
                               1               5

CAG GUA GAU UGC UUC CUU UGG CAU GUC CGC AAA CAA GUU GCA GAC CAA      101
Gln Val Asp Cys Phe Leu Trp His Val Arg Lys Gln Val Ala Asp Gln
 10                  15                  20                  25

GAA CUA GGU GAU GCC CCA UUC CUU GAU CGG CUU CGC CGA GAU CAG AAG      149
Glu Leu Gly Asp Ala Pro Phe Leu Asp Arg Leu Arg Arg Asp Gln Lys
                 30                  35                  40

UCC CUA AGG GGA AGA GGC AGU ACU CUC GGU CUG AAC AUC GAA ACA GCC      197
Ser Leu Arg Gly Arg Gly Ser Thr Leu Gly Leu Asn Ile Glu Thr Ala
             45                  50                  55

ACC CGU GUU GGA AAG CAG AUA GUG GAG AGG AUU CUG AAG GAA GAA UCC      245
Thr Arg Val Gly Lys Gln Ile Val Glu Arg Ile Leu Lys Glu Glu Ser
         60                  65                  70

GAU GAG GCA CUU AAA AUG ACC AUG GCC UCC GCA CCU GCU UCG CGA UAC      293
Asp Glu Ala Leu Lys Met Thr Met Ala Ser Ala Pro Ala Ser Arg Tyr
     75                  80                  85
```

-continued

```
CUA ACU GAC AUG ACU AUU GAG GAA AUG UCA AGG GAC UGG UUC AUG CUA      341
Leu Thr Asp Met Thr Ile Glu Glu Met Ser Arg Asp Trp Phe Met Leu
 90                 95                 100                 105

AUG CCC AAG CAG AAA GUG GCA GGC CCU CUU UGU AUC AGA AUG GAC CAG      389
Met Pro Lys Gln Lys Val Ala Gly Pro Leu Cys Ile Arg Met Asp Gln
                110                 115                 120

GCA AUC AUG GAU AAG AAC AUC AUA UUG AAA GCG AAU UUC AGU GUG AUU      437
Ala Ile Met Asp Lys Asn Ile Ile Leu Lys Ala Asn Phe Ser Val Ile
            125                 130                 135

UUU GAC CGG CUA GAG ACC CUA AUA UUA CUA AGG GCU UUC ACC GAA ACG      485
Phe Asp Arg Leu Glu Thr Leu Ile Leu Leu Arg Ala Phe Thr Glu Thr
        140                 145                 150

GGA GCA AUU GUU GGC GAA AUU UCA CCA UUG CCU UCU CUU CCA GGA CAU      533
Gly Ala Ile Val Gly Glu Ile Ser Pro Leu Pro Ser Leu Pro Gly His
    155                 160                 165

ACU AAU GAG GAU GUC AAA AAU GCA AUU GGG GUC CUC AUC GGA GGA CUU      581
Thr Asn Glu Asp Val Lys Asn Ala Ile Gly Val Leu Ile Gly Gly Leu
170                 175                 180                 185

GAA UGG AAU GAU AAC ACA GUU CGA GUC UCU AAA ACU CUA CAG AGA UUC      629
Glu Trp Asn Asp Asn Thr Val Arg Val Ser Lys Thr Leu Gln Arg Phe
                190                 195                 200

GCU UGG AGA AGC AGU GAU GAG AAU GGG AGA CCU CCA CUC ACU CCA AAA      677
Ala Trp Arg Ser Ser Asp Glu Asn Gly Arg Pro Pro Leu Thr Pro Lys
            205                 210                 215

UAGAAACGGA AAAUGGCGAG AACAAUUAGG UCAAAAGUUC GAAGAAAUAA GAUGGCUGAU    737

UGAAGAAGUG AGACACAAAU UGAAGAUAAC AGAGAAUAGU UUUGAGCAAA UAACAUUUAU    797

GCAAGCCUUA CAGCUGCUAU UUGAAGUGGA ACAAGAGAUA AGAACUUUCU CGUUUCAGCU    857

UAUUUAAUGA UAAAAAACAC CCUUGUUUCU ACU                                 890
```

(2) INFORMATION FOR SEQ ID NO: 2:

(i) SEQUENCE CHARACTERISTICS:
(A) LENGTH: 217 amino acids
(B) TYPE: amino acid
(D) TOPOLOGY: linear (ii) MOLECULE TYPE: protein (xi) SEQUENCE DESCRIPTION: SEQ ID NO: 2:

```
Met Asp Pro Asn Thr Val Ser Ser Phe Gln Val Asp Cys Phe Leu Trp
  1               5                  10                  15

His Val Arg Lys Gln Val Ala Asp Gln Glu Leu Gly Asp Ala Pro Phe
             20                  25                  30

Leu Asp Arg Leu Arg Arg Asp Gln Lys Ser Leu Arg Gly Arg Gly Ser
         35                  40                  45

Thr Leu Gly Leu Asn Ile Glu Thr Ala Thr Arg Val Gly Lys Gln Ile
     50                  55                  60

Val Glu Arg Ile Leu Lys Glu Glu Ser Asp Glu Ala Leu Lys Met Thr
 65                  70                  75                  80

Met Ala Ser Ala Pro Ala Ser Arg Tyr Leu Thr Asp Met Thr Ile Glu
                 85                  90                  95

Glu Met Ser Arg Asp Trp Phe Met Leu Met Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140
```

```
Ile Leu Leu Arg Ala Phe Thr Glu Thr Gly Ala Ile Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Arg Ser Ser Asp Glu
        195                 200                 205

Asn Gly Arg Pro Pro Leu Thr Pro Lys
    210                 215


(2) INFORMATION FOR SEQ ID NO: 3:

     (i) SEQUENCE CHARACTERISTICS:
          (A) LENGTH: 418 base pairs
          (B) TYPE: nucleic acid
          (C) STRANDEDNESS: single
          (D) TOPOLOGY: linear

    (ii) MOLECULE TYPE: RNA (genomic)

    (ix) FEATURE:
          (A) NAME/KEY: CDS
          (B) LOCATION: 27..389
          (D) OTHER INFORMATION: /product= "Nonstructural protein 2"
               /gene= "NS2"

    (xi) SEQUENCE DESCRIPTION: SEQ ID NO: 3:

AGCAAAAGCA GGGUGACAAA GACAUA AUG GAU CCU AAC ACU GUG UCA AGC UUU      53
                             Met Asp Pro Asn Thr Val Ser Ser Phe
                               1               5

CAG GAC AUA CUA AUG AGG AUG UCA AAA AUG CAA UUG GGG UCC UCA UCG      101
Gln Asp Ile Leu Met Arg Met Ser Lys Met Gln Leu Gly Ser Ser Ser
 10                  15                  20                  25

GAG GAC UUG AAU GGA AUG AUA ACA CAG UUC GAG UCU CUA AAA CUC UAC      149
Glu Asp Leu Asn Gly Met Ile Thr Gln Phe Glu Ser Leu Lys Leu Tyr
                 30                  35                  40

AGA GAU UCG CUU GGA GAA GCA GUG AUG AGA AUG GGA GAC CUC CAC UCA      197
Arg Asp Ser Leu Gly Glu Ala Val Met Arg Met Gly Asp Leu His Ser
             45                  50                  55

CUC CAA AAU AGA AAC GGA AAA UGG CGA GAA CAA UUA GGU CAA AAG UUC      245
Leu Gln Asn Arg Asn Gly Lys Trp Arg Glu Gln Leu Gly Gln Lys Phe
         60                  65                  70

GAA GAA AUA AGA UGG CUG AUU GAA GAA GUG AGA CAC AAA UUG AAG AUA      293
Glu Glu Ile Arg Trp Leu Ile Glu Glu Val Arg His Lys Leu Lys Ile
     75                  80                  85

ACA GAG AAU AGU UUU GAG CAA AUA ACA UUU AUG CAA GCC UUA CAG CUG      341
Thr Glu Asn Ser Phe Glu Gln Ile Thr Phe Met Gln Ala Leu Gln Leu
 90                  95                 100                 105

CUA UUU GAA GUG GAA CAA GAG AUA AGA ACU UUC UCG UUU CAG CUU AUU      389
Leu Phe Glu Val Glu Gln Glu Ile Arg Thr Phe Ser Phe Gln Leu Ile
                110                 115                 120

UAAUGAUAAA AAACACCCUU GUUUCUACU                                      418


(2) INFORMATION FOR SEQ ID NO: 4:

     (i) SEQUENCE CHARACTERISTICS:
          (A) LENGTH: 121 amino acids
          (B) TYPE: amino acid
          (D) TOPOLOGY: linear
```

(ii) MOLECULE TYPE: protein (xi) SEQUENCE DESCRIPTION: SEQ ID NO: 4:

```
Met Asp Pro Asn Thr Val Ser Ser Phe Gln Asp Ile Leu Met Arg Met
  1               5                  10                  15

Ser Lys Met Gln Leu Gly Ser Ser Ser Glu Asp Leu Asn Gly Met Ile
            20                  25                  30

Thr Gln Phe Glu Ser Leu Lys Leu Tyr Arg Asp Ser Leu Gly Glu Ala
        35                  40                  45

Val Met Arg Met Gly Asp Leu His Ser Leu Gln Asn Arg Asn Gly Lys
     50                  55                  60

Trp Arg Glu Gln Leu Gly Gln Lys Phe Glu Glu Ile Arg Trp Leu Ile
 65                  70                  75                  80

Glu Glu Val Arg His Lys Leu Lys Ile Thr Glu Asn Ser Phe Glu Gln
                 85                  90                  95

Ile Thr Phe Met Gln Ala Leu Gln Leu Leu Phe Glu Val Glu Gln Glu
            100                 105                 110

Ile Arg Thr Phe Ser Phe Gln Leu Ile
        115                 120
```

(2) INFORMATION FOR SEQ ID NO: 5:

(i) SEQUENCE CHARACTERISTICS:
(A) LENGTH: 1027 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: cold-adapted "Master Strain" A/Ann Arbor/6/60 7PI (H2N2)

(vii) IMMEDIATE SOURCE:
(B) CLONE: M (ix) FEATURE:
(A) NAME/KEY: exon
(B) LOCATION: 26..51
(D) OTHER INFORMATION: /product= "matrix protein M2"
/gene= "M"
/note= "matrix protein M2"
/citation= ([1][2])

(ix) FEATURE:
(A) NAME/KEY: exon
(B) LOCATION: 740..1004
(D) OTHER INFORMATION: /product= "matrix protein M2"
/gene= "M"
/note= "matrix protein M2"
/citation= ([1][2])

(ix) FEATURE:
(A) NAME/KEY: conflict
(B) LOCATION: replace(969, "u")
(D) OTHER INFORMATION: /note= "u in ca "master" strain and in wt2(3)"
/citation= ([1][2])

(ix) FEATURE:
(A) NAME/KEY: CDS
(B) LOCATION: join(26..51, 740..1004)
(D) OTHER INFORMATION: /product= "matrix protein M2"
/gene= "M"
/note= "matrix protein M2"
/citation= ([1][2])

```
    (ix) FEATURE:
         (A) NAME/KEY: CDS
         (B) LOCATION: 26..781
         (D) OTHER INFORMATION: /product= "matrix protein M1"
              /gene= "M"
              /note= "matrix protein M1"
              /citation= ([1][2])

     (x) PUBLICATION INFORMATION:
         (A) AUTHORS: Herlocher, M L
              Maassab, H F
              Webster, R G
         (B) TITLE: Molecular and biological changes in the cold
              adapted master strain A/AA/6/60 (H2N2) influenza
              virus
         (C) JOURNAL: Proceedings of the National Academy of Sciences
              of the USA
         (G) DATE: 1993
         (K) RELEVANT RESIDUES IN SEQ ID NO:5: FROM 1 TO 1027

     (x) PUBLICATION INFORMATION:
         (A) AUTHORS: Cox, N J
              Kitame, F
              Kendal, A P
              Maassab, H F
              Naeve, C
         (B) TITLE: Identification of sequence changes in the
              cold-adapted live attenuated influenza vaccine
              strain, A/Ann Arbor/6/60(H2N2)
         (C) JOURNAL: Virology
         (D) VOLUME: 167
         (F) PAGES: 554-557
         (G) DATE: 1988
         (K) RELEVANT RESIDUES IN SEQ ID NO:5: FROM 1 TO 1027

    (xi) SEQUENCE DESCRIPTION: SEQ ID NO: 5:

AGCAAAAGCA GGUAGAUAUU GAAAG AUG AGU CUU CUA ACC GAG GUC GAA ACG       52
                            Met Ser Leu Leu Thr Glu Val Glu Thr
                              1               5

UAC GUU CUC UCU AUC AUC CCG UCA GGC CCC CUC AAA GCC GAG AUC GCA      100
Tyr Val Leu Ser Ile Ile Pro Ser Gly Pro Leu Lys Ala Glu Ile Ala
 10                  15                  20                  25

CAG AGA CUU GAA GAU GUC UUU GCU GGG AAA AAC ACC GAU CUU GAG GCU      148
Gln Arg Leu Glu Asp Val Phe Ala Gly Lys Asn Thr Asp Leu Glu Ala
                 30                  35                  40

CUC AUG GAA UGG CUA AAG ACA AGA CCA AUC CUG UCA CCU CUG ACU AAG      196
Leu Met Glu Trp Leu Lys Thr Arg Pro Ile Leu Ser Pro Leu Thr Lys
             45                  50                  55

GGG AUU UUG GGA UUU GUA UUC ACG CUC ACC GUG CCC AGU GAG CGA GGA      244
Gly Ile Leu Gly Phe Val Phe Thr Leu Thr Val Pro Ser Glu Arg Gly
         60                  65                  70

CUG CAG CGU AGA CGC UUU GUC CAA AAU GCC CUC AAU GGG AAU GGG GAU      292
Leu Gln Arg Arg Arg Phe Val Gln Asn Ala Leu Asn Gly Asn Gly Asp
     75                  80                  85

CCA AAU AAC AUG GAC AGA GCA GUU AAA CUG UAU AGA AAG CUU AAG AGG      340
Pro Asn Asn Met Asp Arg Ala Val Lys Leu Tyr Arg Lys Leu Lys Arg
 90                  95                 100                 105

GAG AUA ACA UUC CAU GGG GCC AAA GAA AUA GCG CUC AGU UAU UCU GCU      388
Glu Ile Thr Phe His Gly Ala Lys Glu Ile Ala Leu Ser Tyr Ser Ala
                110                 115                 120

GGU GCA CUU GCC AGU UGU AUG GGC CUC AUA UAC AAC AGG AUG GGG GCU      436
Gly Ala Leu Ala Ser Cys Met Gly Leu Ile Tyr Asn Arg Met Gly Ala
            125                 130                 135

GUG ACC ACU GAA GUG GUC UUA GGC CUG GUA UGU GCA ACC UGU GAA CAG      484
Val Thr Thr Glu Val Val Leu Gly Leu Val Cys Ala Thr Cys Glu Gln
        140                 145                 150

AUU GCU GAC UCC CAG CAU AGG UCU CAU AGG CAA AUG GUG ACA ACA ACC      532
Ile Ala Asp Ser Gln His Arg Ser His Arg Gln Met Val Thr Thr Thr
    155                 160                 165
```

-continued

```
AAU CCA CUA AUA AGA CAU GAG AAC AGA AUG GUU CUG GCC AGC ACU ACA      580
Asn Pro Leu Ile Arg His Glu Asn Arg Met Val Leu Ala Ser Thr Thr
170                 175                 180                 185

GCU AAG GCU AUG GAG CAA AUG GCU GGA UCG AGU GAG CAA GCA GCA GAG      628
Ala Lys Ala Met Glu Gln Met Ala Gly Ser Ser Glu Gln Ala Ala Glu
                190                 195                 200

GCC AUG GAG GUU GCU AGU CAG GCC AGG CAA AUG GUG CAG GCA AUG AGA      676
Ala Met Glu Val Ala Ser Gln Ala Arg Gln Met Val Gln Ala Met Arg
            205                 210                 215

GUU AUU GGG ACU CAU CCU AGC UCC AGU GCU GGU CUA AAA AAU GAU CUU      724
Val Ile Gly Thr His Pro Ser Ser Ser Ala Gly Leu Lys Asn Asp Leu
        220                 225                 230

CUU GAA AAU UUG CAG GCC UAU CAG AAA CGA AUG GGG GUG CAG AUG CAA      772
Leu Glu Asn Leu Gln Ala Tyr Gln Lys Arg Met Gly Val Gln Met Gln
    235                 240                 245

CGA UUC AAG UGACCCUCUU GUUGUUGCCG CGAGUAUCAU UGGGAUCUUG              821
Arg Phe Lys
250

CACUUGAUAU UGUGGAUUCU UGAUCAUCUU UUUUUCAAAU GCAUUUAUCG CUUCUUUAAA    881

CACGGUCUGA AAAGAGGGCC UUCUACGGAA GGAGUACCAG AGUCUAUGAG GGAAGAAUAU    941

CGAAAGGAAC AGCAGAGUGC UGUGGAUUCU GACGAUAGUC AUUUUGUCAG CAUAGAGCUG   1001

GAGUAAAAAA CUACCUUGUU UCUACU                                        1027
```

(2) INFORMATION FOR SEQ ID NO: 6:

(i) SEQUENCE CHARACTERISTICS:
(A) LENGTH: 252 amino acids
(B) TYPE: amino acid
(D) TOPOLOGY: linear (ii) MOLECULE TYPE: protein (xi) SEQUENCE DESCRIPTION: SEQ ID NO: 6:

```
Met Ser Leu Leu Thr Glu Val Glu Thr Tyr Val Leu Ser Ile Ile Pro
  1               5                  10                  15

Ser Gly Pro Leu Lys Ala Glu Ile Ala Gln Arg Leu Glu Asp Val Phe
            20                  25                  30

Ala Gly Lys Asn Thr Asp Leu Glu Ala Leu Met Glu Trp Leu Lys Thr
        35                  40                  45

Arg Pro Ile Leu Ser Pro Leu Thr Lys Gly Ile Leu Gly Phe Val Phe
    50                  55                  60

Thr Leu Thr Val Pro Ser Glu Arg Gly Leu Gln Arg Arg Arg Phe Val
 65                  70                  75                  80

Gln Asn Ala Leu Asn Gly Asn Gly Asp Pro Asn Asn Met Asp Arg Ala
                 85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Val Leu
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190
```

```
Ala Gly Ser Ser Glu Gln Ala Ala Glu Ala Met Glu Val Ala Ser Gln
        195                 200                 205

Ala Arg Gln Met Val Gln Ala Met Arg Val Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250
```

(2) INFORMATION FOR SEQ ID NO: 7:

(i) SEQUENCE CHARACTERISTICS:
(A) LENGTH: 339 base pairs
(B) TYPE: nucleic acid
(C) STRANDEDNESS: single
(D) TOPOLOGY: linear (ii) MOLECULE TYPE: RNA (genomic)

(ix) FEATURE:
(A) NAME/KEY: CDS
(B) LOCATION: 26..316
(D) OTHER INFORMATION: /product= "Matrix M2"

(xi) SEQUENCE DESCRIPTION: SEQ ID NO: 7:

```
AGCAAAAGCA GGUAGAUAUU GAAAG AUG AGU CUU CUA ACC GAG GUC GAA ACG       52
                            Met Ser Leu Leu Thr Glu Val Glu Thr
                              1               5

CCU AUC AGA AAC GAA UGG GGG UGC AGA UGC AAC GAU UCA AGU GAC CCU      100
Pro Ile Arg Asn Glu Trp Gly Cys Arg Cys Asn Asp Ser Ser Asp Pro
 10                  15                  20                  25

CUU GUU GUU GCC GCG AGU AUC AUU GGG AUC UUG CAC UUG AUA UUG UGG      148
Leu Val Val Ala Ala Ser Ile Ile Gly Ile Leu His Leu Ile Leu Trp
                 30                  35                  40

AUU CUU GAU CAU CUU UUU UUC AAA UGC AUU UAU CGC UUC UUU AAA CAC      196
Ile Leu Asp His Leu Phe Phe Lys Cys Ile Tyr Arg Phe Phe Lys His
             45                  50                  55

GGU CUG AAA AGA GGG CCU UCU ACG GAA GGA GUA CCA GAG UCU AUG AGG      244
Gly Leu Lys Arg Gly Pro Ser Thr Glu Gly Val Pro Glu Ser Met Arg
         60                  65                  70

GAA GAA UAU CGA AAG GAA CAG CAG AGU GCU GUG GAU UCU GAC GAU AGU      292
Glu Glu Tyr Arg Lys Glu Gln Gln Ser Ala Val Asp Ser Asp Asp Ser
     75                  80                  85

CAU UUU GUC AGC AUA GAG CUG GAG UAAAAAACUA CCUUGUUUCU ACU            339
His Phe Val Ser Ile Glu Leu Glu
 90                  95
```

(2) INFORMATION FOR SEQ ID NO: 8:

(i) SEQUENCE CHARACTERISTICS:
(A) LENGTH: 97 amino acids
(B) TYPE: amino acid
(D) TOPOLOGY: linear (ii) MOLECULE TYPE: protein (xi) SEQUENCE DESCRIPTION: SEQ ID NO: 8:

```
Met Ser Leu Leu Thr Glu Val Glu Thr Pro Ile Arg Asn Glu Trp Gly
  1               5                  10                  15

Cys Arg Cys Asn Asp Ser Ser Asp Pro Leu Val Val Ala Ala Ser Ile
             20                  25                  30

Ile Gly Ile Leu His Leu Ile Leu Trp Ile Leu Asp His Leu Phe Phe
        35                  40                  45
```

```
Lys Cys Ile Tyr Arg Phe Phe Lys His Gly Leu Lys Arg Gly Pro Ser
     50                  55                  60

Thr Glu Gly Val Pro Glu Ser Met Arg Glu Glu Tyr Arg Lys Glu Gln
 65                  70                  75                  80

Gln Ser Ala Val Asp Ser Asp Asp Ser His Phe Val Ser Ile Glu Leu
                 85                  90                  95

Glu
```

(2) INFORMATION FOR SEQ ID NO: 9:

(i) SEQUENCE CHARACTERISTICS:
(A) LENGTH: 1566 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: cold-adapted "Master Strain" A/Ann Arbor/6/60 7PI (H2N2)

(vii) IMMEDIATE SOURCE:
(B) CLONE: NP (ix) FEATURE:
(A) NAME/KEY: mutation
(B) LOCATION: replace(113, "c")
(D) OTHER INFORMATION: /note= "c in ca "master" strain; a in wt2(3); a in 1988 reported ca vaccine strain (manuscript), but c reported in 1988 genbank"
/citation= ([1][2])

(ix) FEATURE:
(A) NAME/KEY: conflict
(B) LOCATION: replace(146, "g")
(D) OTHER INFORMATION: /note= "g in ca "master" strain and in wt2(3)"
/citation= ([1][2])

(ix) FEATURE:
(A) NAME/KEY: conflict
(B) LOCATION: replace(627, "c")
(D) OTHER INFORMATION: /note= "c in ca "master" strain and in wt2(3); a in 1988 reported ca vaccine strain"
/citation= ([1][2])

(ix) FEATURE:
(A) NAME/KEY: conflict
(B) LOCATION: replace(909, "g")
(D) OTHER INFORMATION: /note= "g in ca "master" strain and in wt2(3); c in 1988 reported ca vaccine strain"
/citation= ([1][2])

(ix) FEATURE:
(A) NAME/KEY: conflict
(B) LOCATION: replace(1550, "a")
(D) OTHER INFORMATION: /note= "a in ca "master" strain and in wt2(3)"
/citation= ([1][2])

(ix) FEATURE:
(A) NAME/KEY: CDS
(B) LOCATION: 46..1539
(D) OTHER INFORMATION: /product= "Nucleoprotein"
/gene= "NP"
/note= "nucleoprotein"
/citation= ([1][2])

(x) PUBLICATION INFORMATION:
(A) AUTHORS: Herlocher, M L
Maassab, H F
Webster, R W (B) TITLE: Molecular and biological changes in the cold adapted master strain A/AA/6/60 (H2N2) influenza virus
(C) JOURNAL: Proceedings of the National Academy of Sciences of the USA
(G) DATE: 1993
(K) RELEVANT RESIDUES IN SEQ ID NO:9: FROM 1 TO 1566

(x) PUBLICATION INFORMATION:
(A) AUTHORS: Cox, N J
Kitame, F
Kendal, A P
Maassab, H F
Naeve, C
(B) TITLE: Identification of sequence changes in the cold-adapted live attenuated influenza vaccine strain, A/Ann Arbor/6/60 (H2N2)
(C) JOURNAL: Virology
(D) VOLUME: 167
(F) PAGES: 554-567
(G) DATE: 1988
(K) RELEVANT RESIDUES IN SEQ ID NO:9: FROM 1 TO 1566

(xi) SEQUENCE DESCRIPTION: SEQ ID NO: 9:

```
AGCAAAAGCA GGGUAGAUAA UCACUCACUG AGUGACAUCA AAAUC AUG GCG UCC         54
                                                  Met Ala Ser
                                                    1

CAA GGC ACC AAA CGG UCU UAU GAA CAG AUG GAA ACU GAU GGG GAA CGC      102
Gln Gly Thr Lys Arg Ser Tyr Glu Gln Met Glu Thr Asp Gly Glu Arg
      5                  10                  15

CAG AAU GCA ACU GAA AUC AGA GCA UCC GUC GGG AAG AUG AUU GGU GGA      150
Gln Asn Ala Thr Glu Ile Arg Ala Ser Val Gly Lys Met Ile Gly Gly
 20                  25                  30                  35

AUU GGA CGA UUC UAC AUC CAA AUG UGC ACC GAA CUU AAA CUC AGU GAU      198
Ile Gly Arg Phe Tyr Ile Gln Met Cys Thr Glu Leu Lys Leu Ser Asp
                 40                  45                  50

UAU GAG GGG CGG CUG AUC CAG AAC AGC UUA ACA AUA GAG AGA AUG GUG      246
Tyr Glu Gly Arg Leu Ile Gln Asn Ser Leu Thr Ile Glu Arg Met Val
             55                  60                  65

CUC UCU GCU UUU GAC GAG AGG AGG AAU AAA UAU CUG GAA GAA CAU CCC      294
Leu Ser Ala Phe Asp Glu Arg Arg Asn Lys Tyr Leu Glu Glu His Pro
         70                  75                  80

AGC GCG GGG AAG GAU CCU AAG AAA ACU GGA GGA CCC AUA UAC AAG AGA      342
Ser Ala Gly Lys Asp Pro Lys Lys Thr Gly Gly Pro Ile Tyr Lys Arg
     85                  90                  95

GUA GAU GGA AAG UGG AUG AGG GAA CUC GUC CUU UAU GAC AAA GAA GAA      390
Val Asp Gly Lys Trp Met Arg Glu Leu Val Leu Tyr Asp Lys Glu Glu
100                 105                 110                 115

AUA AGG CGA AUC UGG CGC CAA GCU AAU AAU GGU GAU GAU GCA ACA GCU      438
Ile Arg Arg Ile Trp Arg Gln Ala Asn Asn Gly Asp Asp Ala Thr Ala
                120                 125                 130

GGU CUG ACU CAC AUG AUG AUC UGG CAU UCC AAU UUG AAU GAU ACA ACA      486
Gly Leu Thr His Met Met Ile Trp His Ser Asn Leu Asn Asp Thr Thr
            135                 140                 145

UAC CAG AGG ACA AGA GCU CUU GUU CGC ACC GGA AUG GAU CCC AGG AUG      534
Tyr Gln Arg Thr Arg Ala Leu Val Arg Thr Gly Met Asp Pro Arg Met
        150                 155                 160

UGC UCU UUG AUG CAG GGU UCG ACU CUC CCU AGG AGG UCU GGA GCC GCA      582
Cys Ser Leu Met Gln Gly Ser Thr Leu Pro Arg Arg Ser Gly Ala Ala
    165                 170                 175

GGC GCU GCA GUC AAA GGA GUU GGG ACA AUG GUG AUG GAG UUG AUC AGG      630
Gly Ala Ala Val Lys Gly Val Gly Thr Met Val Met Glu Leu Ile Arg
180                 185                 190                 195
```

-continued

```
AUG AUC AAA CGU GGG AUC AAU GAU CGG AAC UUC UGG AGA GGU GAG AAU      678
Met Ile Lys Arg Gly Ile Asn Asp Arg Asn Phe Trp Arg Gly Glu Asn
                200                 205                 210

GGG CGG AAA ACA AGG AAU GCU UAU GAG AGA AUG UGC AAC AUU CUC AAA      726
Gly Arg Lys Thr Arg Asn Ala Tyr Glu Arg Met Cys Asn Ile Leu Lys
            215                 220                 225

GGA AAA UUU CAA ACA GCU GCA CAA AGA GCA AUG AUG GAU CAA GUG AGA      774
Gly Lys Phe Gln Thr Ala Ala Gln Arg Ala Met Met Asp Gln Val Arg
        230                 235                 240

GAA AGC CGG AAC CCA GGA AAU GCU GAG AUC GAA GAU CUC AUC UUU CUG      822
Glu Ser Arg Asn Pro Gly Asn Ala Glu Ile Glu Asp Leu Ile Phe Leu
    245                 250                 255

GCA CGG UCU GCA CUC AUA UUG AGA GGG UCA GUU GCU CAC AAA UCU UGU      870
Ala Arg Ser Ala Leu Ile Leu Arg Gly Ser Val Ala His Lys Ser Cys
260                 265                 270                 275

CUG CCU GCC UGU GUG UAU GGA CCU GCC GUA GCC AGU GGG UAC GAC UUC      918
Leu Pro Ala Cys Val Tyr Gly Pro Ala Val Ala Ser Gly Tyr Asp Phe
                280                 285                 290

GAA AAA GAG GGA UAC UCU UUA GUA GGG AUA GAC CCU UUC AAA CUG CUU      966
Glu Lys Glu Gly Tyr Ser Leu Val Gly Ile Asp Pro Phe Lys Leu Leu
            295                 300                 305

CAA AAC AGC CAA GUA UAC AGC CUA AUC AGA CCG AAU GAG AAU CCA GCA     1014
Gln Asn Ser Gln Val Tyr Ser Leu Ile Arg Pro Asn Glu Asn Pro Ala
        310                 315                 320

CAC AAG AGU CAG CUG GUG UGG AUG GCA UGC AAU UCU GCU GCA UUU GAA     1062
His Lys Ser Gln Leu Val Trp Met Ala Cys Asn Ser Ala Ala Phe Glu
    325                 330                 335

GAU CUA AGA GUA UCA AGC UUC AUC AGA GGG ACC AAA GUA AUC CCA AGG     1110
Asp Leu Arg Val Ser Ser Phe Ile Arg Gly Thr Lys Val Ile Pro Arg
340                 345                 350                 355

GGG AAA CUU UCC ACU AGA GGA GUA CAA AUU GCU UCA AAU GAA AAC AUG     1158
Gly Lys Leu Ser Thr Arg Gly Val Gln Ile Ala Ser Asn Glu Asn Met
                360                 365                 370

GAU ACU AUG GGA UCA AGU ACU CUU GAA CUG AGA AGC AGG UAC UGG GCC     1206
Asp Thr Met Gly Ser Ser Thr Leu Glu Leu Arg Ser Arg Tyr Trp Ala
            375                 380                 385

AUA AGG ACC AGA AGU GGA GGA AAC ACU AAU CAA CAG AGG GCC UCU GCA     1254
Ile Arg Thr Arg Ser Gly Gly Asn Thr Asn Gln Gln Arg Ala Ser Ala
        390                 395                 400

GGU CAA AUC AGU GUA CAA CCU ACG UUU UCU GUG CAA AGA AAC CUC CCA     1302
Gly Gln Ile Ser Val Gln Pro Thr Phe Ser Val Gln Arg Asn Leu Pro
    405                 410                 415

UUU GAC AAA CCA ACC AUC AUG GCA GCA UUC ACU GGG AAU GCA GAG GGA     1350
Phe Asp Lys Pro Thr Ile Met Ala Ala Phe Thr Gly Asn Ala Glu Gly
420                 425                 430                 435

AGA ACA UCA GAC AUG AGG GCA GAA AUC AUA AGG AUG AUG GAA GGU GCA     1398
Arg Thr Ser Asp Met Arg Ala Glu Ile Ile Arg Met Met Glu Gly Ala
                440                 445                 450

AAA CCA GAA GAA GUG UCC UUC CAG GGG CGG GGA GUC UUC GAG CUC UCG     1446
Lys Pro Glu Glu Val Ser Phe Gln Gly Arg Gly Val Phe Glu Leu Ser
            455                 460                 465

GAC GAA AAG GCA ACG AAC CCG AUC GUG CCC UCU UUU GAC AUG AGU AAU     1494
Asp Glu Lys Ala Thr Asn Pro Ile Val Pro Ser Phe Asp Met Ser Asn
        470                 475                 480

GAA GGA UCU UAU UUC UUC GGA GAC AAU GCA GAG GAG UAC GAC AAU         1539
Glu Gly Ser Tyr Phe Phe Gly Asp Asn Ala Glu Glu Tyr Asp Asn
    485                 490                 495

UAAGGAAAAA AUACCCUUGU UUCUACU                                       1566
```

(2) INFORMATION FOR SEQ ID NO: 10:

(i) SEQUENCE CHARACTERISTICS:
(A) LENGTH: 498 amino acids
(B) TYPE: amino acid
(D) TOPOLOGY: linear (ii) MOLECULE TYPE: protein (xi) SEQUENCE DESCRIPTION: SEQ ID NO: 10:

```
Met Ala Ser Gln Gly Thr Lys Arg Ser Tyr Glu Gln Met Glu Thr Asp
  1               5                  10                  15

Gly Glu Arg Gln Asn Ala Thr Glu Ile Arg Ala Ser Val Gly Lys Met
             20                  25                  30

Ile Gly Gly Ile Gly Arg Phe Tyr Ile Gln Met Cys Thr Glu Leu Lys
         35                  40                  45

Leu Ser Asp Tyr Glu Gly Arg Leu Ile Gln Asn Ser Leu Thr Ile Glu
     50                  55                  60

Arg Met Val Leu Ser Ala Phe Asp Glu Arg Arg Asn Lys Tyr Leu Glu
 65                  70                  75                  80

Glu His Pro Ser Ala Gly Lys Asp Pro Lys Lys Thr Gly Gly Pro Ile
                 85                  90                  95

Tyr Lys Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Asn Ala Tyr Glu Arg Met Cys Asn
    210                 215                 220

Ile Leu Lys Gly Lys Phe Gln Thr Ala Ala Gln Arg Ala Met Met Asp
225                 230                 235                 240

Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Ser Ser Phe Ile Arg Gly Thr Lys Val
            340                 345                 350

Ile Pro Arg Gly Lys Leu Ser Thr Arg Gly Val Gln Ile Ala Ser Asn
        355                 360                 365
```

```
Glu Asn Met Asp Thr Met Gly Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Asp Lys Pro Thr Ile Met Ala Ala Phe Thr Gly Asn
            420                 425                 430

Ala Glu Gly Arg Thr Ser Asp Met Arg Ala Glu Ile Ile Arg Met Met
        435                 440                 445

Glu Gly Ala Lys Pro Glu Glu Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```

(2) INFORMATION FOR SEQ ID NO: 11:

(i) SEQUENCE CHARACTERISTICS:
(A) LENGTH: 2233 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: cold-adapted “Master Strain” A/Ann Arbor/6/60 7PI (H2N2)

(vii) IMMEDIATE SOURCE:
(B) CLONE: PA (ix) FEATURE:
(A) NAME/KEY: conflict
(B) LOCATION: replace(20, “c”)
(D) OTHER INFORMATION: /note= “c in ca ”master“ strain and in wt2(3)”
/citation= ([1][2])

(ix) FEATURE:
(A) NAME/KEY: conflict
(B) LOCATION: replace(75, “g”)
(D) OTHER INFORMATION: /note= “g in ca ”master“ strain and in wt2(3); u in 1988 reported ca vaccine strain”
/citation= ([1][2])

(ix) FEATURE:
(A) NAME/KEY: conflict
(B) LOCATION: replace(1861, “g”)
(D) OTHER INFORMATION: /note= “g in ca ”master“ strain and in wt2(3)”
/citation= ([1][2])

(ix) FEATURE:
(A) NAME/KEY: conflict
(B) LOCATION: replace(2167..2168, “cc”)
(D) OTHER INFORMATION: /note= “cc in ca ”master“ strain and in wt2(3)”
/citation= ([1][2])

(ix) FEATURE:
(A) NAME/KEY: CDS
(B) LOCATION: 25..2172

```
          (D) OTHER INFORMATION: /product= "polymerase acidic
               protein"
               /gene= "PA"
               /note= "polymerase acidic protein"
               /citation= ([1][2])

     (x) PUBLICATION INFORMATION:
          (A) AUTHORS: Herlocher, M L
               Maassab, H F
               Webster, R G
          (B) TITLE: Molecular and biological changes in the cold
               adapted master strain A/AA/6/60 (H2N2) influenza
               virus
          (C) JOURNAL: Proceedings of the National Academy of Sciences
               of the USA
          (G) DATE: 1993
          (K) RELEVANT RESIDUES IN SEQ ID NO:11: FROM 1 TO 2233

     (x) PUBLICATION INFORMATION:
          (A) AUTHORS: Cox, N J
               Kitame, F
               Kendal, A P
               Maassab, H F
               Naeve, C
          (B) TITLE: Identification of sequence changes in the
               cold-adapted live attenuated influenza strain,
               A/Ann Arbor/6/60(H2N2)
          (C) JOURNAL: Virology
          (D) VOLUME: 167
          (F) PAGES: 554-567
          (G) DATE: 1988
          (K) RELEVANT RESIDUES IN SEQ ID NO:11: FROM 1 TO 2233

    (xi) SEQUENCE DESCRIPTION: SEQ ID NO: 11:

AGCGAAAGCA GGUACUGAUC CGAA AUG GAA GAU UUU GUG CGA CAA UGC UUC        51
                           Met Glu Asp Phe Val Arg Gln Cys Phe
                             1               5

AAU CCG AUG AUU GUC GAG CUU GCG GAA AAA GCA AUG AAA GAG UAU GGA       99
Asn Pro Met Ile Val Glu Leu Ala Glu Lys Ala Met Lys Glu Tyr Gly
 10                  15                  20                  25

GAG GAU CUG AAA AUC GAA ACA AAC AAA UUU GCA GCA AUA UGC ACU CAC      147
Glu Asp Leu Lys Ile Glu Thr Asn Lys Phe Ala Ala Ile Cys Thr His
                 30                  35                  40

UUG GAA GUA UGC UUC AUG UAU UCA GAU UUU CAU UUC AUC AAU GAG CAA      195
Leu Glu Val Cys Phe Met Tyr Ser Asp Phe His Phe Ile Asn Glu Gln
             45                  50                  55

GGC GAG UCA AUA AUA GUA GAG CUU GAU GAU CCA AAU GCA CUU UUG AAG      243
Gly Glu Ser Ile Ile Val Glu Leu Asp Asp Pro Asn Ala Leu Leu Lys
         60                  65                  70

CAC AGA UUU GAA AUA AUA GAG GGA AGA GAU CGC ACA AUG GCC UGG ACA      291
His Arg Phe Glu Ile Ile Glu Gly Arg Asp Arg Thr Met Ala Trp Thr
     75                  80                  85

GUA GUA AAC AGU AUU UGC AAC ACU ACA GGA GCU GAG AAA CCG AAG UUU      339
Val Val Asn Ser Ile Cys Asn Thr Thr Gly Ala Glu Lys Pro Lys Phe
 90                  95                 100                 105

CUG CCA GAU UUG UAU GAU UAC AAG GAG AAU AGA UUC AUC GAG AUU GGA      387
Leu Pro Asp Leu Tyr Asp Tyr Lys Glu Asn Arg Phe Ile Glu Ile Gly
                110                 115                 120

GUG ACA AGG AGG GAA GUC CAC AUA UAC UAU CUU GAA AAG GCC AAU AAA      435
Val Thr Arg Arg Glu Val His Ile Tyr Tyr Leu Glu Lys Ala Asn Lys
            125                 130                 135

AUU AAA UCU GAG AAG ACA CAC AUC CAC AUU UUC UCA UUC ACU GGG GAA      483
Ile Lys Ser Glu Lys Thr His Ile His Ile Phe Ser Phe Thr Gly Glu
        140                 145                 150

GAA AUG GCC ACA AAG GCC GAC UAC ACU CUC GAU GAG GAA AGC AGG GCU      531
Glu Met Ala Thr Lys Ala Asp Tyr Thr Leu Asp Glu Glu Ser Arg Ala
    155                 160                 165
```

-continued

```
AGG AUC AAA ACC AGA CUA UUC ACC AUA AGA CAA GAA AUG GCU AGC AGA      579
Arg Ile Lys Thr Arg Leu Phe Thr Ile Arg Gln Glu Met Ala Ser Arg
170                 175                 180                 185

GGC CUC UGG GAU UCC UUU CAU CAG UCC GAA AGA GGC GAA GAA ACA AUU      627
Gly Leu Trp Asp Ser Phe His Gln Ser Glu Arg Gly Glu Glu Thr Ile
                190                 195                 200

GAA GAA AGA UUU GAA AUC ACA GGG ACA AUG CGC AGG CUC GCC GAC CAA      675
Glu Glu Arg Phe Glu Ile Thr Gly Thr Met Arg Arg Leu Ala Asp Gln
            205                 210                 215

AGU CUC CCG CCG AAC UUC UCC UGC CUU GAG AAU UUU AGA GCC UAU GUG      723
Ser Leu Pro Pro Asn Phe Ser Cys Leu Glu Asn Phe Arg Ala Tyr Val
        220                 225                 230

GAU GGA UUC GAA CCG AAC GGC UAC AUU GAG GGC AAG CUU UCU CAA AUG      771
Asp Gly Phe Glu Pro Asn Gly Tyr Ile Glu Gly Lys Leu Ser Gln Met
    235                 240                 245

UCC AAA GAA GUA AAU GCU AAA AUU GAA CCU UUU CUG AAA ACA ACA CCA      819
Ser Lys Glu Val Asn Ala Lys Ile Glu Pro Phe Leu Lys Thr Thr Pro
250                 255                 260                 265

AGA CCA AUU AGA CUU CCG GAU GGG CCU CCU UGU UCU CAG CGG UCC AAA      867
Arg Pro Ile Arg Leu Pro Asp Gly Pro Pro Cys Ser Gln Arg Ser Lys
                270                 275                 280

UUC CUG CUG AUG GAU GCU UUA AAA UUA AGC AUU GAG GAC CCA AGU CAC      915
Phe Leu Leu Met Asp Ala Leu Lys Leu Ser Ile Glu Asp Pro Ser His
            285                 290                 295

GAA GGA GAG GGA AUA CCA CUA UAU GAU GCG AUC AAG UGU AUG AGA ACA      963
Glu Gly Glu Gly Ile Pro Leu Tyr Asp Ala Ile Lys Cys Met Arg Thr
        300                 305                 310

UUC UUU GGA UGG AAA GAA CCC UAU GUU GUU AAA CCA CAC GAA AAG GGA     1011
Phe Phe Gly Trp Lys Glu Pro Tyr Val Val Lys Pro His Glu Lys Gly
    315                 320                 325

AUA AAU CCA AAU UAU CUG CUG UCA UGG AAG CAA GUA CUG GCA GAA CUG     1059
Ile Asn Pro Asn Tyr Leu Leu Ser Trp Lys Gln Val Leu Ala Glu Leu
330                 335                 340                 345

CAG GAC AUU GAG AAU GAG GAG AAG AUU CCA AGA ACC AAA AAC AUG AAG     1107
Gln Asp Ile Glu Asn Glu Glu Lys Ile Pro Arg Thr Lys Asn Met Lys
                350                 355                 360

AAA ACG AGU CAG CUA AAG UGG GCA CUU GGU GAG AAC AUG GCA CCA GAG     1155
Lys Thr Ser Gln Leu Lys Trp Ala Leu Gly Glu Asn Met Ala Pro Glu
            365                 370                 375

AAG GUA GAC UUU GAC GAC UGU AGA GAU GUA AGC GAU UUG AAG CAA UAU     1203
Lys Val Asp Phe Asp Asp Cys Arg Asp Val Ser Asp Leu Lys Gln Tyr
        380                 385                 390

GAU AGU GAU GAA CCU GAA UUA AGG UCA CUU UCA AGC UGG AUC CAG AAU     1251
Asp Ser Asp Glu Pro Glu Leu Arg Ser Leu Ser Ser Trp Ile Gln Asn
    395                 400                 405

GAG UUC AAC AAG GCA UGC GAG CUG ACC GAU UCA AUC UGG AUA GAG CUC     1299
Glu Phe Asn Lys Ala Cys Glu Leu Thr Asp Ser Ile Trp Ile Glu Leu
410                 415                 420                 425

GAU GAG AUU GGA GAA GAU GUG GCU CCA AUU GAA CAC AUU GCA AGC AUG     1347
Asp Glu Ile Gly Glu Asp Val Ala Pro Ile Glu His Ile Ala Ser Met
                430                 435                 440

AGA AGG AAU UAC UUC ACA GCA GAG GUG UCU CAU UGC AGA GCC ACA GAA     1395
Arg Arg Asn Tyr Phe Thr Ala Glu Val Ser His Cys Arg Ala Thr Glu
            445                 450                 455

UAU AUA AUG AAG GGG GUA UAC AUU AAU ACU GCC UUG CUU AAU GCA UCC     1443
Tyr Ile Met Lys Gly Val Tyr Ile Asn Thr Ala Leu Leu Asn Ala Ser
        460                 465                 470

UGU GCA GCA AUG GAC GAU UUC CAA CUA AUU CCC AUG AUA AGC AAA UGU     1491
Cys Ala Ala Met Asp Asp Phe Gln Leu Ile Pro Met Ile Ser Lys Cys
    475                 480                 485
```

-continued

```
AGA ACU AAA GAG GGA AGG CGA AAG ACC AAU UUA UAU GGU UUC AUC AUA      1539
Arg Thr Lys Glu Gly Arg Arg Lys Thr Asn Leu Tyr Gly Phe Ile Ile
490                 495                 500                 505

AAA GGA AGA UCU CAC UUA AGG AAU GAC ACC GAC GUG GUA AAC UUU GUG      1587
Lys Gly Arg Ser His Leu Arg Asn Asp Thr Asp Val Val Asn Phe Val
                510                 515                 520

AGC AUG GAG UUU UCU CUC ACU GAC CCA AGA CUU GAG CCA CAC AAA UGG      1635
Ser Met Glu Phe Ser Leu Thr Asp Pro Arg Leu Glu Pro His Lys Trp
            525                 530                 535

GAG AAG UAC UGU GUU CUU GAG AUA GGA GAU AUG CUA CUA AGA AGU GCC      1683
Glu Lys Tyr Cys Val Leu Glu Ile Gly Asp Met Leu Leu Arg Ser Ala
        540                 545                 550

AUA GGC CAG GUG UCA AGG CCC AUG UUC UUG UAU GUG AGG ACA AAU GGA      1731
Ile Gly Gln Val Ser Arg Pro Met Phe Leu Tyr Val Arg Thr Asn Gly
    555                 560                 565

ACA UCA AAG AUU AAA AUG AAA UGG GGA AUG GAG AUG AGG CGU UGC CUC      1779
Thr Ser Lys Ile Lys Met Lys Trp Gly Met Glu Met Arg Arg Cys Leu
570                 575                 580                 585

CUU CAG UCA CUC CAA CAA AUC GAG AGU AUG AUU GAA GCC GAG UCC UCU      1827
Leu Gln Ser Leu Gln Gln Ile Glu Ser Met Ile Glu Ala Glu Ser Ser
                590                 595                 600

GUC AAG GAG AAA GAC AUG ACC AAA GAG UUU UUC GAG AAU AAA UCA GAA      1875
Val Lys Glu Lys Asp Met Thr Lys Glu Phe Phe Glu Asn Lys Ser Glu
            605                 610                 615

ACA UGG CCC AUU GGA GAG UCC CCC AAA GGA GUG GAA GAA GGU UCC AUU      1923
Thr Trp Pro Ile Gly Glu Ser Pro Lys Gly Val Glu Glu Gly Ser Ile
        620                 625                 630

GGG AAG GUC UGC AGG ACU UUA UUA GCC AAG UCG GUA UUC AAU AGC CUG      1971
Gly Lys Val Cys Arg Thr Leu Leu Ala Lys Ser Val Phe Asn Ser Leu
    635                 640                 645

UAU GCA UCU CCA CAA UUA GAA GGA UUU UCA GCU GAA UCA AGA AAA CUG      2019
Tyr Ala Ser Pro Gln Leu Glu Gly Phe Ser Ala Glu Ser Arg Lys Leu
650                 655                 660                 665

CUU CUU GUC GUU CAG GCU CUU AGG GAC AAU CUU GAA CCU GGG ACC UUU      2067
Leu Leu Val Val Gln Ala Leu Arg Asp Asn Leu Glu Pro Gly Thr Phe
                670                 675                 680

GAU CUU GGG GGG CUA UAU GAA GCA AUU GAG GAG UGC CUG AUU AAU GAU      2115
Asp Leu Gly Gly Leu Tyr Glu Ala Ile Glu Glu Cys Leu Ile Asn Asp
            685                 690                 695

CCC UGG GUU UUG CUU AAU GCG UCU UGG UUC AAC UCC UUC CUA ACA CAU      2163
Pro Trp Val Leu Leu Asn Ala Ser Trp Phe Asn Ser Phe Leu Thr His
        700                 705                 710

GCA CCA AGA UAGUUGUGGC AAUGCUACUA UUUGCUAUCC AUACUGUCCA              2212
Ala Pro Arg
    715

AAAAAGUACC UUGUUUCUAC U                                              2233
```

(2) INFORMATION FOR SEQ ID NO: 12:

(i) SEQUENCE CHARACTERISTICS:
(A) LENGTH: 716 amino acids
(B) TYPE: amino acid
(D) TOPOLOGY: linear (ii) MOLECULE TYPE: protein (xi) SEQUENCE DESCRIPTION: SEQ ID NO: 12:

```
Met Glu Asp Phe Val Arg Gln Cys Phe Asn Pro Met Ile Val Glu Leu
  1               5                  10                  15

Ala Glu Lys Ala Met Lys Glu Tyr Gly Glu Asp Leu Lys Ile Glu Thr
             20                  25                  30
```

```
Asn Lys Phe Ala Ala Ile Cys Thr His Leu Glu Val Cys Phe Met Tyr
            35                  40                  45

Ser Asp Phe His Phe Ile Asn Glu Gln Gly Glu Ser Ile Ile Val Glu
    50                  55                  60

Leu Asp Asp Pro Asn Ala Leu Leu Lys His Arg Phe Glu Ile Ile Glu
65                  70                  75                  80

Gly Arg Asp Arg Thr Met Ala Trp Thr Val Val Asn Ser Ile Cys Asn
                85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe His
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asp Gln Ser Leu Pro Pro Asn Phe Ser
    210                 215                 220

Cys Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Lys
                245                 250                 255

Ile Glu Pro Phe Leu Lys Thr Thr Pro Arg Pro Ile Arg Leu Pro Asp
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Tyr Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Arg Thr Lys Asn Met Lys Lys Thr Ser Gln Leu Lys Trp
        355                 360                 365

Ala Leu Gly Glu Asn Met Ala Pro Glu Lys Val Asp Phe Asp Asp Cys
    370                 375                 380

Arg Asp Val Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu
                405                 410                 415

Leu Thr Asp Ser Ile Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460
```

```
Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Val Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Pro Arg
705                 710                 715
```

(2) INFORMATION FOR SEQ ID NO: 13:

(i) SEQUENCE CHARACTERISTICS:
(A) LENGTH: 2341 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: cold adapted "Master Strain" A/AA/6/60 7PI (H2N2)

(vii) IMMEDIATE SOURCE:
(B) CLONE: PB1

(ix) FEATURE:
(A) NAME/KEY: conflict
(B) LOCATION: replace(123, "g")
(D) OTHER INFORMATION: /note= "g in ca "master" strain and in wt2(3)"
/citation= ([1][2])

(ix) FEATURE:
(A) NAME/KEY: conflict
(B) LOCATION: replace(486, "u")
(D) OTHER INFORMATION: /note= "u in ca "master" strain and in wt2(3)"
/citation= ([1][2])

-continued

```
(ix) FEATURE:
      (A) NAME/KEY: conflict
      (B) LOCATION: replace(1195, "g")
      (D) OTHER INFORMATION: /note= "g in ca "master" strain and in
           wt2(3)"
           /citation= ([1][2])

(ix) FEATURE:
      (A) NAME/KEY: mutation
      (B) LOCATION: replace(1276, "g")
      (D) OTHER INFORMATION: /note= "g in ca "master" strain; a in
           wt2(3); g in 1988 reported ca vaccine strain"
           /citation= ([1][2])

(ix) FEATURE:
      (A) NAME/KEY: conflict
      (B) LOCATION: replace(1395, "u")
      (D) OTHER INFORMATION: /note= "u in ca "master" strain and in
           wt2(3)"
           /citation= ([1][2])

(ix) FEATURE:
      (A) NAME/KEY: conflict
      (B) LOCATION: replace(1766, "g")
      (D) OTHER INFORMATION: /note= "g in ca "master" strain and in
           wt2(3)"
           /citation= ([1][2])

(ix) FEATURE:
      (A) NAME/KEY: conflict
      (B) LOCATION: replace(2005, "a")
      (D) OTHER INFORMATION: /note= "a in ca "master" strain and in
           wt2(3)"
           /citation= ([1][2])

(ix) FEATURE:
      (A) NAME/KEY: conflict
      (B) LOCATION: replace(2019, "u")
      (D) OTHER INFORMATION: /note= "u in ca "master" strain and in
           wt2(3)"
           /citation= ([1][2])

(ix) FEATURE:
      (A) NAME/KEY: CDS
      (B) LOCATION: 25..2295
      (D) OTHER INFORMATION: /product= "polymerase basic 1"
           /gene= "PB1"
           /note= "polymerase basic 1"
           /citation= ([1][2])

 (x) PUBLICATION INFORMATION:
      (A) AUTHORS: Herlocher, M L
           Maassab, H F
           Webster, R G
      (B) TITLE: Molecular and biological changes in the cold
           adapted master strain A/AA/6/60 (H2N2) influenza
           virus
      (C) JOURNAL: Proceedings of the National Academy of Sciences
           of the USA
      (G) DATE: 1993
      (K) RELEVANT RESIDUES IN SEQ ID NO:13: FROM 1 TO 2341

 (x) PUBLICATION INFORMATION:
      (A) AUTHORS: Cox, N J
           Kitame, F
           Kendal, A P
           Maassab, H F
           Naeve, C
      (B) TITLE: Identification of sequence changes in the
           cold-adapted live attenuated influenza vaccine
           strain
      (C) JOURNAL: Virology
      (D) VOLUME: 167
      (F) PAGES: 554-567
      (G) DATE: 1988
      (K) RELEVANT RESIDUES IN SEQ ID NO:13: FROM 1 TO 2341
```

```
    (xi) SEQUENCE DESCRIPTION: SEQ ID NO: 13:

AGCGAAAGCA GGCAAACCAU UUGA AUG GAU GUC AAU CCG ACC UUA CUU UUC         51
                           Met Asp Val Asn Pro Thr Leu Leu Phe
                             1               5

UUG AAA GUU CCA GCG CAA AAU GCC AUA AGU ACU ACA UUC CCU UAU ACU        99
Leu Lys Val Pro Ala Gln Asn Ala Ile Ser Thr Thr Phe Pro Tyr Thr
 10                  15                  20                  25

GGA GAU CCU CCA UAC AGC CAU GGG ACA GGA ACA GGA UAC ACC AUG GAC       147
Gly Asp Pro Pro Tyr Ser His Gly Thr Gly Thr Gly Tyr Thr Met Asp
                 30                  35                  40

ACA GUC AAC AGA ACA CAU CAA UAU UCA GAA AAG GGG AAG UGG ACA ACA       195
Thr Val Asn Arg Thr His Gln Tyr Ser Glu Lys Gly Lys Trp Thr Thr
             45                  50                  55

AAC ACG GAA ACU GGA GCG CAC CAA CUU AAC CCA AUU GAU GGA CCA CUA       243
Asn Thr Glu Thr Gly Ala His Gln Leu Asn Pro Ile Asp Gly Pro Leu
         60                  65                  70

CCU GAG GAC AAU GAA CCA AGU GGA UAU GCA CAA ACA GAC UGC GUC CUG       291
Pro Glu Asp Asn Glu Pro Ser Gly Tyr Ala Gln Thr Asp Cys Val Leu
     75                  80                  85

GAA GCA AUG GCU UUC CUU GAA GAA UCC CAC CCA GGA AUC UUU GAA AAC       339
Glu Ala Met Ala Phe Leu Glu Glu Ser His Pro Gly Ile Phe Glu Asn
 90                  95                 100                 105

UCG UGU CUU GAA ACG AUG GAA GUU AUU CAA CAA ACA AGA GUG GAC AAA       387
Ser Cys Leu Glu Thr Met Glu Val Ile Gln Gln Thr Arg Val Asp Lys
                110                 115                 120

CUG ACC CAA GGU CGU CAG ACC UAU GAU UGG ACA UUG AAC AGA AAU CAG       435
Leu Thr Gln Gly Arg Gln Thr Tyr Asp Trp Thr Leu Asn Arg Asn Gln
            125                 130                 135

CCG GCU GCA ACU GCG CUA GCC AAC ACU AUA GAG GUC UUC AGA UCG AAU       483
Pro Ala Ala Thr Ala Leu Ala Asn Thr Ile Glu Val Phe Arg Ser Asn
        140                 145                 150

GGU CUG ACA GCU AAU GAA UCG GGA AGG CUA AUA GAU UUC CUC AAG GAU       531
Gly Leu Thr Ala Asn Glu Ser Gly Arg Leu Ile Asp Phe Leu Lys Asp
    155                 160                 165

GUG AUA GAA UCA AUG GAU AAA GAG GAG AUG GAA AUC ACA ACA CAC UUC       579
Val Ile Glu Ser Met Asp Lys Glu Glu Met Glu Ile Thr Thr His Phe
170                 175                 180                 185

CAA AGA AAA AGA AGA GUA AGA GAC AAC AUG ACC AAG AAA AUG GUC ACA       627
Gln Arg Lys Arg Arg Val Arg Asp Asn Met Thr Lys Lys Met Val Thr
                190                 195                 200

CAA CGA ACA AUA GGA AAG AAG AAG CAA AGA UUG AAC AAG AGA AGC UAU       675
Gln Arg Thr Ile Gly Lys Lys Lys Gln Arg Leu Asn Lys Arg Ser Tyr
            205                 210                 215

CUA AUA AGA GCA CUG ACA UUG AAC ACA AUG ACU AAA GAU GCA GAG AGA       723
Leu Ile Arg Ala Leu Thr Leu Asn Thr Met Thr Lys Asp Ala Glu Arg
        220                 225                 230

GGU AAA UUA AAG AGA AGA GCA AUU GCA ACA CCC GGU AUG CAG AUC AGA       771
Gly Lys Leu Lys Arg Arg Ala Ile Ala Thr Pro Gly Met Gln Ile Arg
    235                 240                 245

GGG UUC GUG UAC UUU GUC GAA ACA CUA GCG AGA AGU AUU UGU GAG AAG       819
Gly Phe Val Tyr Phe Val Glu Thr Leu Ala Arg Ser Ile Cys Glu Lys
250                 255                 260                 265

CUU GAA CAG UCU GGG CUU CCG GUU GGA GGU AAU GAA AAG AAG GCU AAA       867
Leu Glu Gln Ser Gly Leu Pro Val Gly Gly Asn Glu Lys Lys Ala Lys
                270                 275                 280

CUG GCA AAU GUU GUG CGA AAA AUG AUG ACU AAU UCA CAA GAC ACA GAG       915
Leu Ala Asn Val Val Arg Lys Met Met Thr Asn Ser Gln Asp Thr Glu
            285                 290                 295
```

```
CUC UCU UUC ACA AUU ACU GGA GAC AAU ACC AAA UGG AAU GAG AAU CAA       963
Leu Ser Phe Thr Ile Thr Gly Asp Asn Thr Lys Trp Asn Glu Asn Gln
        300                 305                 310

AAU CCU CGG AUG UUC CUG GCG AUG AUA ACA UAC AUC ACA AGA AAU CAA      1011
Asn Pro Arg Met Phe Leu Ala Met Ile Thr Tyr Ile Thr Arg Asn Gln
    315                 320                 325

CCU GAA UGG UUU AGA AAC GUC CUG AGC AUC GCA CCU AUA AUG UUC UCA      1059
Pro Glu Trp Phe Arg Asn Val Leu Ser Ile Ala Pro Ile Met Phe Ser
330                 335                 340                 345

AAU AAA AUG GCA AGA CUA GGG AAA GGA UAC AUG UUC AAA AGC AAG AGC      1107
Asn Lys Met Ala Arg Leu Gly Lys Gly Tyr Met Phe Lys Ser Lys Ser
            350                 355                 360

AUG AAG CUC CGA ACA CAA AUA CCA GCA GAA AUG CUA GCA AGU AUU GAC      1155
Met Lys Leu Arg Thr Gln Ile Pro Ala Glu Met Leu Ala Ser Ile Asp
            365                 370                 375

CUG AAA UAC UUU AAU GAA UCA ACA AGA AAG AAA AUC GAG GAA AUA AGG      1203
Leu Lys Tyr Phe Asn Glu Ser Thr Arg Lys Lys Ile Glu Glu Ile Arg
        380                 385                 390

CCU CUC CUA AUA GAU GGC ACA GUC UCA UUG AGU CCU GGA AUG AUG AUG      1251
Pro Leu Leu Ile Asp Gly Thr Val Ser Leu Ser Pro Gly Met Met Met
    395                 400                 405

GGC AUG UUC AAC AUG CUA AGU ACA GUC UUA GGA GUC UCA AUC CUG AAU      1299
Gly Met Phe Asn Met Leu Ser Thr Val Leu Gly Val Ser Ile Leu Asn
410                 415                 420                 425

CUU GGA CAA AAG AAG UAC ACC AAA ACA ACA UAC UGG UGG GAC GGA CUC      1347
Leu Gly Gln Lys Lys Tyr Thr Lys Thr Thr Tyr Trp Trp Asp Gly Leu
            430                 435                 440

CAA UCC UCU GAU GAC UUC GCC CUC AUA GUG AAU GCA CCA AAU CAU GAU      1395
Gln Ser Ser Asp Asp Phe Ala Leu Ile Val Asn Ala Pro Asn His Asp
            445                 450                 455

GGA AUA CAA GCA GGG GUG GAU AGA UUC UAC AGA ACC UGC AAG CUA GUC      1443
Gly Ile Gln Ala Gly Val Asp Arg Phe Tyr Arg Thr Cys Lys Leu Val
        460                 465                 470

GGA AUC AAU AUG AGC AAA AAG AAG UCC UAC AUA AAU AGG ACA GGG ACA      1491
Gly Ile Asn Met Ser Lys Lys Lys Ser Tyr Ile Asn Arg Thr Gly Thr
    475                 480                 485

UUU GAA UUC ACA AGC UUU UUC UAU CGC UAU GGA UUU GUA GCC AAU UUU      1539
Phe Glu Phe Thr Ser Phe Phe Tyr Arg Tyr Gly Phe Val Ala Asn Phe
490                 495                 500                 505

AGC AUG GAG CUG CCC AGC UUU GGA GUG UCU GGA AUU AAU GAA UCG GCU      1587
Ser Met Glu Leu Pro Ser Phe Gly Val Ser Gly Ile Asn Glu Ser Ala
                510                 515                 520

GAU AUG AGC AUU GGG GUA ACA GUG AUA AAG AAC AAC AUG AUA AAC AAU      1635
Asp Met Ser Ile Gly Val Thr Val Ile Lys Asn Asn Met Ile Asn Asn
            525                 530                 535

GAC CUU GGG CCA GCA ACA GCC CAA CUG GCU CUU CAA CUA UUC AUC AAA      1683
Asp Leu Gly Pro Ala Thr Ala Gln Leu Ala Leu Gln Leu Phe Ile Lys
        540                 545                 550

GAC UAC AGA UAU ACG UAC CGG UGC CAC AGA GGA GAC ACA CAA AUU CAG      1731
Asp Tyr Arg Tyr Thr Tyr Arg Cys His Arg Gly Asp Thr Gln Ile Gln
    555                 560                 565

ACA AGG AGA UCA UUC GAG CUA AAG AAG CUG UGG GGG CAA ACC CGC UCA      1779
Thr Arg Arg Ser Phe Glu Leu Lys Lys Leu Trp Gly Gln Thr Arg Ser
570                 575                 580                 585

AAG GCA GGA CUU UUG GUU UCG GAU GGA GGA CCA AAC UUA UAC AAU AUC      1827
Lys Ala Gly Leu Leu Val Ser Asp Gly Gly Pro Asn Leu Tyr Asn Ile
            590                 595                 600

CGG AAU CUC CAC AUU CCA GAA GUC UGC UUG AAG UGG GAG CUA AUG GAU      1875
Arg Asn Leu His Ile Pro Glu Val Cys Leu Lys Trp Glu Leu Met Asp
            605                 610                 615
```

-continued

```
GAA GAC UAU CAG GGG AGG CUU UGU AAU CCC CUG AAU CCA UUU GUC AGU      1923
Glu Asp Tyr Gln Gly Arg Leu Cys Asn Pro Leu Asn Pro Phe Val Ser
        620                 625                 630

CAU AAG GAG AUU GAG UCU GUA AAC AAU GCU GUG GUA AUG CCA GCU CAC      1971
His Lys Glu Ile Glu Ser Val Asn Asn Ala Val Val Met Pro Ala His
    635                 640                 645

GGU CCA GCC AAG AGC AUG GAA UAU GAU GCU GUU ACU ACU ACA CAC UCU      2019
Gly Pro Ala Lys Ser Met Glu Tyr Asp Ala Val Thr Thr Thr His Ser
650                 655                 660                 665

UGG AUC CCU AAG AGG AAC CGC UCC AUU CUC AAC ACA AGC CAA AGG GGA      2067
Trp Ile Pro Lys Arg Asn Arg Ser Ile Leu Asn Thr Ser Gln Arg Gly
                670                 675                 680

AUU CUU GAA GAU GAA CAG AUG UAU CAG AAG UGU UGC AAU CUA UUC GAG      2115
Ile Leu Glu Asp Glu Gln Met Tyr Gln Lys Cys Cys Asn Leu Phe Glu
            685                 690                 695

AAA UUC UUC CCU AGC AGU UCG UAC AGG AGA CCA GUU GGA AUU UCC AGC      2163
Lys Phe Phe Pro Ser Ser Ser Tyr Arg Arg Pro Val Gly Ile Ser Ser
        700                 705                 710

AUG GUG GAG GCC AUG GUG UCU AGG GCC CGG AUU GAU GCA CGG AUU GAC      2211
Met Val Glu Ala Met Val Ser Arg Ala Arg Ile Asp Ala Arg Ile Asp
    715                 720                 725

UUC GAG UCU GGA CGG AUU AAG AAA GAG GAG UUC GCU GAG AUC AUG AAG      2259
Phe Glu Ser Gly Arg Ile Lys Lys Glu Glu Phe Ala Glu Ile Met Lys
730                 735                 740                 745

AUC UGU UCC ACC AUU GAA GAG CUC AGA CGG CAA AAA UAGUGAAUUU           2305
Ile Cys Ser Thr Ile Glu Glu Leu Arg Arg Gln Lys
                750                 755

AGCUUGUCCU UCAUGAAAAA AUGCCUUGUU UCUACU                              2341
```

(2) INFORMATION FOR SEQ ID NO: 14:

(i) SEQUENCE CHARACTERISTICS:
(A) LENGTH: 757 amino acids
(B) TYPE: amino acid
(D) TOPOLOGY: linear (ii) MOLECULE TYPE: protein (xi) SEQUENCE DESCRIPTION: SEQ ID NO: 14:

```
Met Asp Val Asn Pro Thr Leu Leu Phe Leu Lys Val Pro Ala Gln Asn
  1               5                  10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala His
    50                  55                  60

Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160
```

-continued

```
Gly Arg Leu Ile Asp Phe Leu Lys Asp Val Ile Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Lys Ser Lys Ser Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Glu Ile Arg Pro Leu Leu Ile Asp Gly Thr
385                 390                 395                 400

Val Ser Leu Ser Pro Gly Met Met Met Gly Met Phe Asn Met Leu Ser
                405                 410                 415

Thr Val Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Asp Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525

Val Ile Lys Asn Asn Met Ile Asn Asn Asp Leu Gly Pro Ala Thr Ala
    530                 535                 540

Gln Leu Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Gly Gln Thr Arg Ser Lys Ala Gly Leu Leu Val Ser
            580                 585                 590
```

```
Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Thr Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
            740                 745                 750

Leu Arg Arg Gln Lys
        755
```

(2) INFORMATION FOR SEQ ID NO: 15:

(i) SEQUENCE CHARACTERISTICS:
(A) LENGTH: 2341 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: cold-adapted "Master Strain" A/Ann Arbor/6/60 7PI (H2N2)

(vii) IMMEDIATE SOURCE:
(B) CLONE: PB2

(ix) FEATURE:
(A) NAME/KEY: mutation
(B) LOCATION: replace(141, "g")
(D) OTHER INFORMATION: /note= "g in ca "master" strain; a in wt2(3); g in 1988 reported ca vaccine strain"
/citation= ([1][2])

(ix) FEATURE:
(A) NAME/KEY: conflict
(B) LOCATION: replace(426, "c")
(D) OTHER INFORMATION: /note= "c in ca "master" strain and in wt2(3)"
/citation= ([1][2])

(ix) FEATURE:
(A) NAME/KEY: conflict
(B) LOCATION: replace(714, "u")
(D) OTHER INFORMATION: /note= "u in ca "master" strain and in wt2(3); c in 1988 reported ca vaccine strain"
/citation= ([1][2])

(ix) FEATURE:
(A) NAME/KEY: conflict
(B) LOCATION: replace(821, "g")
(D) OTHER INFORMATION: /note= "g in ca "master" strain and in wt2(3)"
/citation= ([1][2])

```
(ix) FEATURE:
      (A) NAME/KEY: conflict
      (B) LOCATION: replace(963, "g")
      (D) OTHER INFORMATION: /note= "g in ca "master" strain and in
           wt2(3); a in 1988 reported ca vaccine strain"
           /citation= ([1][2])

(ix) FEATURE:
      (A) NAME/KEY: conflict
      (B) LOCATION: replace(1182, "u")
      (D) OTHER INFORMATION: /note= "u in ca "master" strain and in
           wt2(3)"
           /citation= ([1][2])

(ix) FEATURE:
      (A) NAME/KEY: conflict
      (B) LOCATION: replace(1212, "u")
      (D) OTHER INFORMATION: /note= "u in ca "master" strain and in
           wt2(3)"
           /citation= ([1][2])

(ix) FEATURE:
      (A) NAME/KEY: conflict
      (B) LOCATION: replace(1353, "g")
      (D) OTHER INFORMATION: /note= "g in ca "master" strain and in
           wt2(3)"
           /citation= ([1][2])

(ix) FEATURE:
      (A) NAME/KEY: conflict
      (B) LOCATION: replace(1923, "g")
      (D) OTHER INFORMATION: /note= "g in ca "master" strain and in
           wt2(3)"
           /citation= ([1][2])

(ix) FEATURE:
      (A) NAME/KEY: mutation
      (B) LOCATION: replace(1933, "c")
      (D) OTHER INFORMATION: /note= "c in ca "master" strain; u in
           wt2(3); u in 1988 reported ca vaccine strain"
           /citation= ([1][2])

(ix) FEATURE:
      (A) NAME/KEY: CDS
      (B) LOCATION: 28..2304
      (D) OTHER INFORMATION: /product= "polymerase basic 2"
           /gene= "PB2"
           /note= "polymerase basic 2"
           /citation= ([1][2])

 (x) PUBLICATION INFORMATION:
      (A) AUTHORS: Herlocher, M L
           Maassab, H F
           Webster, R G
      (B) TITLE: Molecular and biological changes in the cold
           adapted master strain A/AA/6/60 (H2N2) influenza
           virus
      (C) JOURNAL: Proceedings of the National Academy of Sciences
           of the USA
      (G) DATE: 1993
      (K) RELEVANT RESIDUES IN SEQ ID NO:15: FROM 1 TO 2341

 (x) PUBLICATION INFORMATION:
      (A) AUTHORS: Cox, N J
           Kitame, F
           Kendal, A P
           Maassab, H F
           Naeve, C
      (B) TITLE: Identification of sequence changes in the
           cold-adapted live attenuated influenza vaccine
           strain, A/Ann Arbor/6/60(H2N2)
      (C) JOURNAL: Virology
      (D) VOLUME: 167
      (F) PAGES: 554-567
      (G) DATE: 1988
      (K) RELEVANT RESIDUES IN SEQ ID NO:15: FROM 1 TO 2341
```

```
    (xi) SEQUENCE DESCRIPTION: SEQ ID NO: 15:

AGCGAAAGCA GGUCAAUUAU AUUCAAU AUG GAA AGA AUA AAA GAA CUA CGG         51
                              Met Glu Arg Ile Lys Glu Leu Arg
                                1               5

AAU CUG AUG UCG CAG UCU CGC ACU CGC GAG AUA CUA ACA AAA ACC ACA       99
Asn Leu Met Ser Gln Ser Arg Thr Arg Glu Ile Leu Thr Lys Thr Thr
     10                  15                  20

GUG GAC CAU AUG GCC AUA AUU AAG AAG UAC ACA UCA GGG AGG CAG GAA      147
Val Asp His Met Ala Ile Ile Lys Lys Tyr Thr Ser Gly Arg Gln Glu
 25                  30                  35                  40

AAG AAC CCG UCA CUU AGG AUG AAA UGG AUG AUG GCA AUG AAA UAU CCG      195
Lys Asn Pro Ser Leu Arg Met Lys Trp Met Met Ala Met Lys Tyr Pro
                 45                  50                  55

AUU ACA GCC GAC AAG AGG AUA ACA GAA AUG AUU CCU GAG AGA AAU GAG      243
Ile Thr Ala Asp Lys Arg Ile Thr Glu Met Ile Pro Glu Arg Asn Glu
             60                  65                  70

CAA GGG CAA ACU CUA UGG AGU AAA AUG AGU GAU GCC GGA UCG GAU CGU      291
Gln Gly Gln Thr Leu Trp Ser Lys Met Ser Asp Ala Gly Ser Asp Arg
         75                  80                  85

GUG AUG GUA UCA CCU CUG GCU GUG ACA UGG UGG AAU AGA AAU GGA CCA      339
Val Met Val Ser Pro Leu Ala Val Thr Trp Trp Asn Arg Asn Gly Pro
     90                  95                 100

AUG ACA AGU ACG GUU CAU UAU CCA AAA AUC UAC AAA ACU UAU UUU GAG      387
Met Thr Ser Thr Val His Tyr Pro Lys Ile Tyr Lys Thr Tyr Phe Glu
105                 110                 115                 120

AAA GUC GAA AGG UUA AAA CAU GGA ACC UUU GGC CCU GUC CAU UUU AGA      435
Lys Val Glu Arg Leu Lys His Gly Thr Phe Gly Pro Val His Phe Arg
                125                 130                 135

AAC CAA GUC AAA AUA CGC CGA AGA GUU GAC AUA AAU CCU GGU CAU GCA      483
Asn Gln Val Lys Ile Arg Arg Arg Val Asp Ile Asn Pro Gly His Ala
            140                 145                 150

GAC CUC AGU GCC AAG GAG GCA CAG GAU GUA AUC AUG GAA GUU GUU UUC      531
Asp Leu Ser Ala Lys Glu Ala Gln Asp Val Ile Met Glu Val Val Phe
        155                 160                 165

CCU AAC GAA GUG GGG GCC AGG AUA CUA ACG UCG GAA UCG CAA UUA ACA      579
Pro Asn Glu Val Gly Ala Arg Ile Leu Thr Ser Glu Ser Gln Leu Thr
    170                 175                 180

AUA ACC AAA GAG AAA AAA GAA GAA CUC CAG GAU UGC AAA AUU UCA CCU      627
Ile Thr Lys Glu Lys Lys Glu Glu Leu Gln Asp Cys Lys Ile Ser Pro
185                 190                 195                 200

UUG AUG GUU GCG UAC AUG UUA GAG AGA GAA CUU GUC CGA AAA ACG AGA      675
Leu Met Val Ala Tyr Met Leu Glu Arg Glu Leu Val Arg Lys Thr Arg
                205                 210                 215

UUU CUC CCA GUU GCU GGU GGA ACA AGC AGU GUG UAC AUU GAA GUG UUG      723
Phe Leu Pro Val Ala Gly Gly Thr Ser Ser Val Tyr Ile Glu Val Leu
            220                 225                 230

CAC UUG ACU CAA GGA ACA UGC UGG GAA CAG AUG UAC ACU CCA GGU GGA      771
His Leu Thr Gln Gly Thr Cys Trp Glu Gln Met Tyr Thr Pro Gly Gly
        235                 240                 245

GAA GUG AGG AAU GAU GAU GUU GAU CAA AGU CUA AUU AUU GCA GCC AGG      819
Glu Val Arg Asn Asp Asp Val Asp Gln Ser Leu Ile Ile Ala Ala Arg
    250                 255                 260

AGC AUA GUG AGA AGA GCA GCA GUA UCA GCA GAU CCA CUA GCA UCU UUA      867
Ser Ile Val Arg Arg Ala Ala Val Ser Ala Asp Pro Leu Ala Ser Leu
265                 270                 275                 280

UUG GAG AUG UGC CAC AGC ACA CAG AUU GGC GGG ACA AGG AUG GUG GAC      915
Leu Glu Met Cys His Ser Thr Gln Ile Gly Gly Thr Arg Met Val Asp
                285                 290                 295
```

-continued

```
AUU CUU AGG CAG AAC CCA ACA GAA GAG CAA GCU GUG GAA AUA UGC AAG      963
Ile Leu Arg Gln Asn Pro Thr Glu Glu Gln Ala Val Glu Ile Cys Lys
            300                 305                 310

GCU GCA AUG GGA CUG AGG AUC AGC UCA UCC UUC AGU UUU GGC GGG UUC     1011
Ala Ala Met Gly Leu Arg Ile Ser Ser Ser Phe Ser Phe Gly Gly Phe
        315                 320                 325

ACA UUU AAG AGA ACA AGC GGA UCA UCA GUC AAG AGA GAG GAA GAA GUG     1059
Thr Phe Lys Arg Thr Ser Gly Ser Ser Val Lys Arg Glu Glu Glu Val
    330                 335                 340

CUU ACG GGC AAU CUU CAA ACA UUG AAA AUA AGG GUG CAU GAG GGA UAC     1107
Leu Thr Gly Asn Leu Gln Thr Leu Lys Ile Arg Val His Glu Gly Tyr
345                 350                 355                 360

GAG GAG UUC ACA AUG GUU GGG AAA AGG GCA ACA GCU AUA CUC AGA AAA     1155
Glu Glu Phe Thr Met Val Gly Lys Arg Ala Thr Ala Ile Leu Arg Lys
                365                 370                 375

GCA ACC AGG AGA UUG AUU CAG CUG AUU GUG AGU GGA AGA GAC GAA CAG     1203
Ala Thr Arg Arg Leu Ile Gln Leu Ile Val Ser Gly Arg Asp Glu Gln
            380                 385                 390

UCG AUA GCU GAA GCA AUA AUU GUG GCC AUG GUA UUU UCA CAA GAA GAU     1251
Ser Ile Ala Glu Ala Ile Ile Val Ala Met Val Phe Ser Gln Glu Asp
        395                 400                 405

UGU AUG AUA AAA GCA GUU AGA GGU GAU CUG AAU UUC GUU AAU AGG GCA     1299
Cys Met Ile Lys Ala Val Arg Gly Asp Leu Asn Phe Val Asn Arg Ala
    410                 415                 420

AAU CAG CGA UUG AAU CCC AUG CAU CAA CUU UUA AGA CAU UUU CAG AAG     1347
Asn Gln Arg Leu Asn Pro Met His Gln Leu Leu Arg His Phe Gln Lys
425                 430                 435                 440

GAU GCG AAA GUG CUU UUU CAA AAU UGG GGA AUU GAA CAU AUC GAC AAU     1395
Asp Ala Lys Val Leu Phe Gln Asn Trp Gly Ile Glu His Ile Asp Asn
                445                 450                 455

GUG AUG GGA AUG AUU GGG GUA UUA CCA GAC AUG ACU CCA AGC ACA GAG     1443
Val Met Gly Met Ile Gly Val Leu Pro Asp Met Thr Pro Ser Thr Glu
            460                 465                 470

AUG UCA AUG AGA GGG GUA AGA GUC AGC AAA AUG GGC GUA GAU GAA UAC     1491
Met Ser Met Arg Gly Val Arg Val Ser Lys Met Gly Val Asp Glu Tyr
        475                 480                 485

UCC AGC GCG GAG AGA GUA GUG GUG AGC AUU GAC CGG UUU UUG AGA GUU     1539
Ser Ser Ala Glu Arg Val Val Val Ser Ile Asp Arg Phe Leu Arg Val
    490                 495                 500

CGA GAC CAA CGA GGA AAU GUA CUA CUA UCU CCU GAG GAG GUC AGU GAA     1587
Arg Asp Gln Arg Gly Asn Val Leu Leu Ser Pro Glu Glu Val Ser Glu
505                 510                 515                 520

ACA CAG GGA ACA GAG AAA CUG ACA AUA ACU UAC UCA UCG UCA AUG AUG     1635
Thr Gln Gly Thr Glu Lys Leu Thr Ile Thr Tyr Ser Ser Ser Met Met
                525                 530                 535

UGG GAG AUU AAU GGC CCU GAG UCA GUG UUG GUC AAU ACC UAU CAG UGG     1683
Trp Glu Ile Asn Gly Pro Glu Ser Val Leu Val Asn Thr Tyr Gln Trp
            540                 545                 550

AUC AUC AGA AAC UGG GAA ACU GUU AAA AUU CAG UGG UCU CAG AAU CCU     1731
Ile Ile Arg Asn Trp Glu Thr Val Lys Ile Gln Trp Ser Gln Asn Pro
        555                 560                 565

ACA AUG CUA UAC AAU AAA AUG GAA UUU GAG CCA UUU CAG UCU UUA GUU     1779
Thr Met Leu Tyr Asn Lys Met Glu Phe Glu Pro Phe Gln Ser Leu Val
    570                 575                 580

CCU AAG GCC AUU AGA GGC CAA UAC AGU GGG UUU GUU AGG ACU CUA UUC     1827
Pro Lys Ala Ile Arg Gly Gln Tyr Ser Gly Phe Val Arg Thr Leu Phe
585                 590                 595                 600

CAA CAA AUG AGG GAU GUA CUU GGG ACA UUU GAU ACC ACC CAG AUA AUA     1875
Gln Gln Met Arg Asp Val Leu Gly Thr Phe Asp Thr Thr Gln Ile Ile
                605                 610                 615
```

```
AAA CUU CUU CCC UUU GCA GCC GCC CCA CCA AAG CAA AGU AGA AUG CAG      1923
Lys Leu Leu Pro Phe Ala Ala Ala Pro Pro Lys Gln Ser Arg Met Gln
            620                 625                 630

UUC UCU UCA CUG ACU GUG AAU GUG AGG GGA UCA GGA AUG AGA AUA CUU      1971
Phe Ser Ser Leu Thr Val Asn Val Arg Gly Ser Gly Met Arg Ile Leu
        635                 640                 645

GUA AGG GGC AAU UCU CCU AUA UUC AAC UAC AAC AAG ACC ACU AAG AGA      2019
Val Arg Gly Asn Ser Pro Ile Phe Asn Tyr Asn Lys Thr Thr Lys Arg
    650                 655                 660

CUA ACA AUU CUC GGA AAG GAU GCU GGC ACU UUA ACU GAA GAC CCA GAU      2067
Leu Thr Ile Leu Gly Lys Asp Ala Gly Thr Leu Thr Glu Asp Pro Asp
665                 670                 675                 680

GAA GGC ACA UCU GGA GUG GAG UCC GCU GUU CUG AGA GGA UUC CUC AUU      2115
Glu Gly Thr Ser Gly Val Glu Ser Ala Val Leu Arg Gly Phe Leu Ile
                685                 690                 695

CUG GGC AAA GAA GAU AGG AGA UAU GGA CCA GCA UUA AGC AUC AAU GAA      2163
Leu Gly Lys Glu Asp Arg Arg Tyr Gly Pro Ala Leu Ser Ile Asn Glu
            700                 705                 710

CUG AGU AAC CUU GCG AAA GGA GAA AAG GCU AAU GUA CUA AUU GGG CAA      2211
Leu Ser Asn Leu Ala Lys Gly Glu Lys Ala Asn Val Leu Ile Gly Gln
        715                 720                 725

GGA GAC GUG GUG UUG GUA AUG AAA CGA AAA CGG AAC UCU AGC AUA CUU      2259
Gly Asp Val Val Leu Val Met Lys Arg Lys Arg Asn Ser Ser Ile Leu
    730                 735                 740

ACU GAC AGC CAG ACA GCG ACC AAA AGG AUU CGG AUG GCC AUC AAU          2304
Thr Asp Ser Gln Thr Ala Thr Lys Arg Ile Arg Met Ala Ile Asn
745                 750                 755

UAAUGUUGAA UAGUUUAAAA ACGACCUUGU UUCUACU                             2341
```

(2) INFORMATION FOR SEQ ID NO: 16:

(i) SEQUENCE CHARACTERISTICS:
(A) LENGTH: 759 amino acids
(B) TYPE: amino acid
(D) TOPOLOGY: linear (ii) MOLECULE TYPE: protein (xi) SEQUENCE DESCRIPTION: SEQ ID NO: 16:

```
Met Glu Arg Ile Lys Glu Leu Arg Asn Leu Met Ser Gln Ser Arg Thr
  1               5                  10                  15

Arg Glu Ile Leu Thr Lys Thr Thr Val Asp His Met Ala Ile Ile Lys
             20                  25                  30

Lys Tyr Thr Ser Gly Arg Gln Glu Lys Asn Pro Ser Leu Arg Met Lys
         35                  40                  45

Trp Met Met Ala Met Lys Tyr Pro Ile Thr Ala Asp Lys Arg Ile Thr
     50                  55                  60

Glu Met Ile Pro Glu Arg Asn Glu Gln Gly Gln Thr Leu Trp Ser Lys
 65                  70                  75                  80

Met Ser Asp Ala Gly Ser Asp Arg Val Met Val Ser Pro Leu Ala Val
                 85                  90                  95

Thr Trp Trp Asn Arg Asn Gly Pro Met Thr Ser Thr Val His Tyr Pro
            100                 105                 110

Lys Ile Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160
```

```
Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Ser Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Glu Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Lys
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu His Ile Asp Asn Val Met Gly Met Ile Gly Val Leu
    450                 455                 460

Pro Asp Met Thr Pro Ser Thr Glu Met Ser Met Arg Gly Val Arg Val
465                 470                 475                 480

Ser Lys Met Gly Val Asp Glu Tyr Ser Ser Ala Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590
```

-continued

```
Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
    610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Ile Phe
                645                 650                 655

Asn Tyr Asn Lys Thr Thr Lys Arg Leu Thr Ile Leu Gly Lys Asp Ala
            660                 665                 670

Gly Thr Leu Thr Glu Asp Pro Asp Glu Gly Thr Ser Gly Val Glu Ser
        675                 680                 685

Ala Val Leu Arg Gly Phe Leu Ile Leu Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asn Ser Ser Ile Leu Thr Asp Ser Gln Thr Ala Thr Lys
            740                 745                 750

Arg Ile Arg Met Ala Ile Asn
        755
```

(2) INFORMATION FOR SEQ ID NO: 17:

(i) SEQUENCE CHARACTERISTICS:
(A) LENGTH: 1773 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: cold-adapted "Master Strain" A/Ann Arbor/6/60 7PI (H2N2)

(vii) IMMEDIATE SOURCE:
(B) CLONE: HA (ix) FEATURE:
(A) NAME/KEY: mutation
(B) LOCATION: replace(144, "u")
(D) OTHER INFORMATION: /gene= "HA"
/note= "u in ca "master" strain; a in w2(3)"
/citation= ([1])

(ix) FEATURE:
(A) NAME/KEY: mutation
(B) LOCATION: replace(455, "a")
(D) OTHER INFORMATION: /gene= "HA"
/note= "a in ca "master" strain; g in wt2(3)"
/citation= ([1])

(ix) FEATURE:
(A) NAME/KEY: mutation
(B) LOCATION: replace(729, "c")
(D) OTHER INFORMATION: /gene= "HA"
/note= "c in ca "master" strain; a in wt2(3)"
/citation= ([1])

(ix) FEATURE:
(A) NAME/KEY: CDS
(B) LOCATION: 44..1729
(D) OTHER INFORMATION: /product= "hemagglutinin"
/gene= "HA"
/note= "hemagglutinin protein"
/citation= ([1])

```
     (x) PUBLICATION INFORMATION:
          (A) AUTHORS: Herlocher, M L
               Maassab, H F
               Webster, R G
          (B) TITLE: Molecular and biological changes in the cold
               adapted master strain A/AA/6/60 (H2N2) influenza
               virus
          (C) JOURNAL: Proceedings of the National Academy of Sciences
               of the USA
          (G) DATE: 1993
          (K) RELEVANT RESIDUES IN SEQ ID NO:17: FROM 1 TO 1773

    (xi) SEQUENCE DESCRIPTION: SEQ ID NO: 17:

AGCAAAAGCA GGGGUUAUAC CAUAGACAAC CAAAAGCAAA ACA AUG GCC AUC AUU       55
                                                Met Ala Ile Ile
                                                  1

UAU CUC AUU CUC CUG UUC ACA GCA GUG AGA GGG GAC AAG AUA UGC AUU      103
Tyr Leu Ile Leu Leu Phe Thr Ala Val Arg Gly Asp Lys Ile Cys Ile
  5                  10                  15                  20

GGA UAC CAU GCC AAU AAU UCC ACA GAG ACG GUC GAC ACA AUU CUA GAG      151
Gly Tyr His Ala Asn Asn Ser Thr Glu Thr Val Asp Thr Ile Leu Glu
                 25                  30                  35

CGG AAC GUC ACU GUG ACU CAU GCC AAG GAC AUU CUU GAG AAG ACC CAU      199
Arg Asn Val Thr Val Thr His Ala Lys Asp Ile Leu Glu Lys Thr His
             40                  45                  50

AAC GGA AAG UUA UGC AAA CUA AAC GGA AUC CCU CCA CUU GAA CUA GGG      247
Asn Gly Lys Leu Cys Lys Leu Asn Gly Ile Pro Pro Leu Glu Leu Gly
         55                  60                  65

GAC UGU AGC AUU GCC GGA UGG CUC CUU GGA AAU CCA GAA UGU GAU AGG      295
Asp Cys Ser Ile Ala Gly Trp Leu Leu Gly Asn Pro Glu Cys Asp Arg
     70                  75                  80

CUU CUA AGU GUG CCA GAA UGG UCC UAU AUA AUG GAG AAA GAA AAC CCG      343
Leu Leu Ser Val Pro Glu Trp Ser Tyr Ile Met Glu Lys Glu Asn Pro
 85                  90                  95                 100

AGA AAC GGU UUG UGU UAU CCA GGC AAC UUC AAU GAU UAU GAA GAA UUG      391
Arg Asn Gly Leu Cys Tyr Pro Gly Asn Phe Asn Asp Tyr Glu Glu Leu
                105                 110                 115

AAA CAU CUC CUC AGC AGC GUG AAA CAU UUC GAG AAA GUA AAG AUU CUG      439
Lys His Leu Leu Ser Ser Val Lys His Phe Glu Lys Val Lys Ile Leu
            120                 125                 130

CCC AAA GAU AGA UGG ACA CAG CAU ACA ACA ACU GGA GGU UCA CAG GCC      487
Pro Lys Asp Arg Trp Thr Gln His Thr Thr Thr Gly Gly Ser Gln Ala
        135                 140                 145

UGC GCG GUG UCU GGU AAU CCA UCA UUC UUC AGG AAC AUG GUC UGG CUG      535
Cys Ala Val Ser Gly Asn Pro Ser Phe Phe Arg Asn Met Val Trp Leu
    150                 155                 160

ACA GAG GAA GGA UCA AAU UAU CCG GUU GCC AAA GGA UCG UAC AAC AAU      583
Thr Glu Glu Gly Ser Asn Tyr Pro Val Ala Lys Gly Ser Tyr Asn Asn
165                 170                 175                 180

ACA AGC GGA GAA CAA AUG CUA AUA AUU UGG GGG GUG CAC CAU CCC AUU      631
Thr Ser Gly Glu Gln Met Leu Ile Ile Trp Gly Val His His Pro Ile
                185                 190                 195

GAU GAG ACA GAA CAA AGA ACA UUG UAC CAG AAU GUG GGA ACC UAU GUU      679
Asp Glu Thr Glu Gln Arg Thr Leu Tyr Gln Asn Val Gly Thr Tyr Val
            200                 205                 210

UCC GUA GGC ACA UCA ACA UUG AAC AAA AGG UCA ACC CCA GAA AUA GCA      727
Ser Val Gly Thr Ser Thr Leu Asn Lys Arg Ser Thr Pro Glu Ile Ala
        215                 220                 225

ACA AGG CCU AAA GUG AAU GGA CUA GGA AGU AGA AUG GAA UUC UCU UGG      775
Thr Arg Pro Lys Val Asn Gly Leu Gly Ser Arg Met Glu Phe Ser Trp
    230                 235                 240
```

-continued

```
ACC CUC UUG GAU AUG UGG GAC ACC AUA AAU UUU GAG AGU ACU GGU AAU      823
Thr Leu Leu Asp Met Trp Asp Thr Ile Asn Phe Glu Ser Thr Gly Asn
245                 250                 255                 260

CUA AUU GCA CCA GAG UAU GGA UUC AAA AUA UCG AAA AGA GGU AGU UCU      871
Leu Ile Ala Pro Glu Tyr Gly Phe Lys Ile Ser Lys Arg Gly Ser Ser
                265                 270                 275

GGG AUC AUG AAA ACA GAA GGA ACA CUU GAG AAC UGU GAG ACC AAA UGC      919
Gly Ile Met Lys Thr Glu Gly Thr Leu Glu Asn Cys Glu Thr Lys Cys
            280                 285                 290

CAA ACU CCU UUG GGA GCA AUA AAU ACA ACA UUG CCU UUU CAC AAU GUC      967
Gln Thr Pro Leu Gly Ala Ile Asn Thr Thr Leu Pro Phe His Asn Val
        295                 300                 305

CAC CCA CUG ACA AUA GGU GAG UGC CCC AAA UAU GUA AAA UCG GAG AAG     1015
His Pro Leu Thr Ile Gly Glu Cys Pro Lys Tyr Val Lys Ser Glu Lys
    310                 315                 320

UUG GUC UUA GCA ACA GGA CUA AGG AAU GUU CCC CAG AUU GAA UCA AGA     1063
Leu Val Leu Ala Thr Gly Leu Arg Asn Val Pro Gln Ile Glu Ser Arg
325                 330                 335                 340

GGA UUG UUU GGG GCA AUA GCU GGU UUU AUA GAA GGA GGA UGG CAA GGA     1111
Gly Leu Phe Gly Ala Ile Ala Gly Phe Ile Glu Gly Gly Trp Gln Gly
                345                 350                 355

AUG GUU GAU GGU UGG UAU GGA UAC CAU CAC AGC AAU GAC CAG GGA UCA     1159
Met Val Asp Gly Trp Tyr Gly Tyr His His Ser Asn Asp Gln Gly Ser
            360                 365                 370

GGG UAU GCA GCA GAC AAA GAA UCC ACU CAA AAG GCA UUU GAU GGA AUC     1207
Gly Tyr Ala Ala Asp Lys Glu Ser Thr Gln Lys Ala Phe Asp Gly Ile
        375                 380                 385

ACC AAC AAG GUA AAU UCU GUG AUU GAA AAG AUA AAC ACC CAA UUU GAA     1255
Thr Asn Lys Val Asn Ser Val Ile Glu Lys Ile Asn Thr Gln Phe Glu
    390                 395                 400

GCU GUU GGG AAA GAA UUC AGU AAC UUA GAG AGA AGA CUG GAG AAC UUG     1303
Ala Val Gly Lys Glu Phe Ser Asn Leu Glu Arg Arg Leu Glu Asn Leu
405                 410                 415                 420

AAC AAA AAG AUG GAA GAC GGG UUU CUA GAU GUG UGG ACA UAC AAU GCU     1351
Asn Lys Lys Met Glu Asp Gly Phe Leu Asp Val Trp Thr Tyr Asn Ala
                425                 430                 435

GAG CUU CUA GUU CUG AUG GAA AAU GAG AGG ACA CUU GAC UUU CAU GAU     1399
Glu Leu Leu Val Leu Met Glu Asn Glu Arg Thr Leu Asp Phe His Asp
            440                 445                 450

UCU AAU GUC AAG AAU CUG UAU GAU AAA GUC AGA AUG CAG CUG AGG GAC     1447
Ser Asn Val Lys Asn Leu Tyr Asp Lys Val Arg Met Gln Leu Arg Asp
        455                 460                 465

AAC GUC AAA GAA CUA GGA AAU GGA UGU UUU GAA UUU UAU CAC AAA UGU     1495
Asn Val Lys Glu Leu Gly Asn Gly Cys Phe Glu Phe Tyr His Lys Cys
    470                 475                 480

GAU GAU GAA UGC AUG AAU AGU GUG AAA AAC GGG ACA UAU GAU UAU CCC     1543
Asp Asp Glu Cys Met Asn Ser Val Lys Asn Gly Thr Tyr Asp Tyr Pro
485                 490                 495                 500

AAG UAU GAA GAA GAG UCU AAA CUA AAU AGA AAU GAA AUU AAA GGG GUA     1591
Lys Tyr Glu Glu Glu Ser Lys Leu Asn Arg Asn Glu Ile Lys Gly Val
                505                 510                 515

AAA UUG AGC AGC AUG GGG GUU UGU CGG AUC CUU GCC AUU UAU GCU ACA     1639
Lys Leu Ser Ser Met Gly Val Cys Arg Ile Leu Ala Ile Tyr Ala Thr
            520                 525                 530

GUA GCA GGU UCU CUG UCA CUG GCA AUC AUG AUG GCU GGG AUC UCU UUC     1687
Val Ala Gly Ser Leu Ser Leu Ala Ile Met Met Ala Gly Ile Ser Phe
        535                 540                 545
```

```
UGG AUG UGC UCC AAC GGG UCU CUG CAG UGC AGG AUC UGC AUA           1729
Trp Met Cys Ser Asn Gly Ser Leu Gln Cys Arg Ile Cys Ile
    550                 555                 560

UGAUUAUAAG UCAUUUUAUA AUUAAAAACA CCCUUGUUUC UACU                  1773


(2) INFORMATION FOR SEQ ID NO: 18:

     (i) SEQUENCE CHARACTERISTICS:
          (A) LENGTH: 562 amino acids
          (B) TYPE: amino acid
          (D) TOPOLOGY: linear

    (ii) MOLECULE TYPE: protein

    (xi) SEQUENCE DESCRIPTION: SEQ ID NO: 18:

Met Ala Ile Ile Tyr Leu Ile Leu Leu Phe Thr Ala Val Arg Gly Asp
  1               5                  10                  15

Lys Ile Cys Ile Gly Tyr His Ala Asn Asn Ser Thr Glu Thr Val Asp
            20                  25                  30

Thr Ile Leu Glu Arg Asn Val Thr Val Thr His Ala Lys Asp Ile Leu
        35                  40                  45

Glu Lys Thr His Asn Gly Lys Leu Cys Lys Leu Asn Gly Ile Pro Pro
     50                  55                  60

Leu Glu Leu Gly Asp Cys Ser Ile Ala Gly Trp Leu Leu Gly Asn Pro
 65                  70                  75                  80

Glu Cys Asp Arg Leu Leu Ser Val Pro Glu Trp Ser Tyr Ile Met Glu
                85                  90                  95

Lys Glu Asn Pro Arg Asn Gly Leu Cys Tyr Pro Gly Asn Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Thr Gln His Thr Thr Thr Gly
    130                 135                 140

Gly Ser Gln Ala Cys Ala Val Ser Gly Asn Pro Ser Phe Phe Arg Asn
145                 150                 155                 160

Met Val Trp Leu Thr Glu Glu Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Ile Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Thr Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335
```

```
Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Ile Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Cys Arg Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile
```

(2) INFORMATION FOR SEQ ID NO: 19:

(i) SEQUENCE CHARACTERISTICS:
(A) LENGTH: 1467 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: cold-adapted "Master Strain" A/Ann Arbor/6/60 7PI (H2N2)

(vii) IMMEDIATE SOURCE:
(B) CLONE: NA (ix) FEATURE:
(A) NAME/KEY: mutation
(B) LOCATION: replace(394, "u")
(D) OTHER INFORMATION: /product= "Neuraminidase"
/gene= "NA"
/note= "u in ca "master" strain; c in wt2(3)"
/citation= ([1])

(ix) FEATURE:
(A) NAME/KEY: mutation
(B) LOCATION: replace(604, "u")
(D) OTHER INFORMATION: /product= "Neuraminidase"
/gene= "NA"
/note= "u in ca "master" strain; a in wt2(3)"
/citation= ([1])

```
    (ix) FEATURE:
         (A) NAME/KEY: CDS
         (B) LOCATION: 20..1426
         (D) OTHER INFORMATION: /product= "neuraminidase"
              /gene= "NA"
              /note= "neuraminidase protein"
              /citation= ([1])

     (x) PUBLICATION INFORMATION:
         (A) AUTHORS: Herlocher, M L
              Maassab, H F
              Webster, R G
         (B) TITLE: Molecular and biological changes in the cold
              adapted master strain A/AA/6/60 (H2N2) Influenza
              Virus
         (C) JOURNAL: Proceedings of the National Academy of Sciences
              of the USA
         (G) DATE: 1993
         (K) RELEVANT RESIDUES IN SEQ ID NO:19: FROM 1 TO 1467

    (xi) SEQUENCE DESCRIPTION: SEQ ID NO: 19:

AGCAAAAGCA GGAGUGAAA AUG AAU CCA AAU CAA AAG ACA AUA ACA AUU GGC      52
                     Met Asn Pro Asn Gln Lys Thr Ile Thr Ile Gly
                       1               5                  10

UCU GUC UCU CUC ACC AUC GCA ACA GUA UGC UUC CUC AUG CAG AUU GCC      100
Ser Val Ser Leu Thr Ile Ala Thr Val Cys Phe Leu Met Gln Ile Ala
             15                  20                  25

AUC CUG GCA ACU ACU GUG ACA UUG CAC CUU AAG CAA CAU GAG UGC GAC      148
Ile Leu Ala Thr Thr Val Thr Leu His Leu Lys Gln His Glu Cys Asp
         30                  35                  40

UCC CCC GCG AGC AAC CAA GUA AUG CCA UGU GAA CCA AUA AUA AUA GAA      196
Ser Pro Ala Ser Asn Gln Val Met Pro Cys Glu Pro Ile Ile Ile Glu
     45                  50                  55

AGG AAC AUA ACA GAG AUA GUG UAU UUG AAU AAC ACC ACC AUA GAG AAA      244
Arg Asn Ile Thr Glu Ile Val Tyr Leu Asn Asn Thr Thr Ile Glu Lys
 60                  65                  70                  75

GAG AUU UGC CCC GAA GUA GUG GGA UAC AGA AAU UGG UCA AAG CCG CAA      292
Glu Ile Cys Pro Glu Val Val Gly Tyr Arg Asn Trp Ser Lys Pro Gln
                 80                  85                  90

UGU CAA AUU ACA GGA UUU GCA CCU UUU UCU AAG GAC AAU UCA AUC CGG      340
Cys Gln Ile Thr Gly Phe Ala Pro Phe Ser Lys Asp Asn Ser Ile Arg
             95                 100                 105

CUU UCU GCU GGU GGG GAC AUU UGG GUG ACG AGA GAA CCU UAU GUG UCA      388
Leu Ser Ala Gly Gly Asp Ile Trp Val Thr Arg Glu Pro Tyr Val Ser
        110                 115                 120

UGC GAU CCU GGC AAG UGU UAU CAA UUU GCA CUC GGG CAG GGG ACC ACA      436
Cys Asp Pro Gly Lys Cys Tyr Gln Phe Ala Leu Gly Gln Gly Thr Thr
    125                 130                 135

CUA GAC AAC AAA CAU UCA AAU GGC ACA AUA CAU GAU AGA AUC CCU CAU      484
Leu Asp Asn Lys His Ser Asn Gly Thr Ile His Asp Arg Ile Pro His
140                 145                 150                 155

CGA ACC CUA UUA AUG AAU GAG UUG GGU GUU CCA UUU CAU UUA GGA ACC      532
Arg Thr Leu Leu Met Asn Glu Leu Gly Val Pro Phe His Leu Gly Thr
                160                 165                 170

AAA CAA GUG UGU GCA GCA UGG UCC AGC UCA AGU UGU CAC GAU GGA AAA      580
Lys Gln Val Cys Ala Ala Trp Ser Ser Ser Ser Cys His Asp Gly Lys
            175                 180                 185

GCA UGG UUG CAU GUU UGU GUC ACU GGG GAU GAU AGA AAU GCA ACU GCU      628
Ala Trp Leu His Val Cys Val Thr Gly Asp Asp Arg Asn Ala Thr Ala
        190                 195                 200

AGC UUC AUU UAU GAC GGG AAG CUU GUG GAC AGU AUU GGU UCA UGG UCU      676
Ser Phe Ile Tyr Asp Gly Lys Leu Val Asp Ser Ile Gly Ser Trp Ser
    205                 210                 215
```

-continued

```
CAA AAU GUC CUC AGG ACC CAG GAG UCG GAA UGC GUC UGU AUC AAU GGG      724
Gln Asn Val Leu Arg Thr Gln Glu Ser Glu Cys Val Cys Ile Asn Gly
220                 225                 230                 235

ACU UGC ACA GUA GUA AUG ACU GAU GGA AGU GCA UCA GGA AGA GCU GAU      772
Thr Cys Thr Val Val Met Thr Asp Gly Ser Ala Ser Gly Arg Ala Asp
                240                 245                 250

ACU AGA AUA CUA UUC AUU AAA GAG GGG AAA AUU GUC CAU AUU GGC CCA      820
Thr Arg Ile Leu Phe Ile Lys Glu Gly Lys Ile Val His Ile Gly Pro
            255                 260                 265

UUG UCA GGA AGU GCU CAG CAU GUA GAG GAG UGU UCU UGU UAC CCU CGA      868
Leu Ser Gly Ser Ala Gln His Val Glu Glu Cys Ser Cys Tyr Pro Arg
        270                 275                 280

UAU CCU GAC GUC AGA UGU AUC UGC AGA GAC AAC UGG AAA GGC UCU AAU      916
Tyr Pro Asp Val Arg Cys Ile Cys Arg Asp Asn Trp Lys Gly Ser Asn
    285                 290                 295

AGG CCC GUU AUA GAC AUA AAU AUG GAA GAU UAU AGC AUU GAU UCC AGU      964
Arg Pro Val Ile Asp Ile Asn Met Glu Asp Tyr Ser Ile Asp Ser Ser
300                 305                 310                 315

UAU GUG UGC UCA GGG CUU GUU GGC GAC ACA CCC AGG AAC GAC GAC AGC     1012
Tyr Val Cys Ser Gly Leu Val Gly Asp Thr Pro Arg Asn Asp Asp Ser
                320                 325                 330

UCU AGC AAU AGC AAU UGC AGG GAU CCU AAC AAU GAG AGA GGG AAU CCA     1060
Ser Ser Asn Ser Asn Cys Arg Asp Pro Asn Asn Glu Arg Gly Asn Pro
            335                 340                 345

GGA GUG AAA GGC UGG GCC UUU GAC AAU GGA GAU GAU GUA UGG AUG GGA     1108
Gly Val Lys Gly Trp Ala Phe Asp Asn Gly Asp Asp Val Trp Met Gly
        350                 355                 360

AGA ACA AUC AGC AAA GAU UUA CGC UCA GGU UAU GAA ACU UUC AAA GUC     1156
Arg Thr Ile Ser Lys Asp Leu Arg Ser Gly Tyr Glu Thr Phe Lys Val
    365                 370                 375

AUU GGU GGU UGG UCC ACA CCU AAU UCC AAA UCG CAG GUC AAU AGA CAG     1204
Ile Gly Gly Trp Ser Thr Pro Asn Ser Lys Ser Gln Val Asn Arg Gln
380                 385                 390                 395

GUC AUA GUU GAC AAC AAU AAU UGG UCU GGU UAC UCU GGU AUU UUC UCU     1252
Val Ile Val Asp Asn Asn Asn Trp Ser Gly Tyr Ser Gly Ile Phe Ser
                400                 405                 410

GUU GAG GGC AAA AGC UGC AUC AAU AGG UGC UUU UAU GUG GAG UUG AUA     1300
Val Glu Gly Lys Ser Cys Ile Asn Arg Cys Phe Tyr Val Glu Leu Ile
            415                 420                 425

AGG GGA AGG CCA CAG GAG ACU AGA GUA UGG UGG ACC UCA AAC AGU AUU     1348
Arg Gly Arg Pro Gln Glu Thr Arg Val Trp Trp Thr Ser Asn Ser Ile
        430                 435                 440

GUU GUA UUU UGU GGC ACU UCA GGU ACU UAU GGA ACA GGC UCA UGG CCU     1396
Val Val Phe Cys Gly Thr Ser Gly Thr Tyr Gly Thr Gly Ser Trp Pro
    445                 450                 455

GAU GGG GCG AAC AUC AAU UUC AUG CCU AUA UAACGUUUCG CAAUUUUAGA       1446
Asp Gly Ala Asn Ile Asn Phe Met Pro Ile
460                 465

AAAAAACUCC UUGUUUCUAC U                                             1467
```

(2) INFORMATION FOR SEQ ID NO: 20:

(i) SEQUENCE CHARACTERISTICS:
(A) LENGTH: 469 amino acids
(B) TYPE: amino acid
(D) TOPOLOGY: linear (ii) MOLECULE TYPE: protein -continued (xi) SEQUENCE DESCRIPTION: SEQ ID NO: 20:

```
Met Asn Pro Asn Gln Lys Thr Ile Thr Ile Gly Ser Val Ser Leu Thr
  1               5                  10                  15

Ile Ala Thr Val Cys Phe Leu Met Gln Ile Ala Ile Leu Ala Thr Thr
             20                  25                  30

Val Thr Leu His Leu Lys Gln His Glu Cys Asp Ser Pro Ala Ser Asn
         35                  40                  45

Gln Val Met Pro Cys Glu Pro Ile Ile Ile Glu Arg Asn Ile Thr Glu
     50                  55                  60

Ile Val Tyr Leu Asn Asn Thr Thr Ile Glu Lys Glu Ile Cys Pro Glu
 65                  70                  75                  80

Val Val Gly Tyr Arg Asn Trp Ser Lys Pro Gln Cys Gln Ile Thr Gly
                 85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Gly Lys
        115                 120                 125

Cys Tyr Gln Phe Ala Leu Gly Gln Gly Thr Thr Leu Asp Asn Lys His
    130                 135                 140

Ser Asn Gly Thr Ile His Asp Arg Ile Pro His Arg Thr Leu Leu Met
145                 150                 155                 160

Asn Glu Leu Gly Val Pro Phe His Leu Gly Thr Lys Gln Val Cys Ala
                165                 170                 175

Ala Trp Ser Ser Ser Ser Cys His Asp Gly Lys Ala Trp Leu His Val
            180                 185                 190

Cys Val Thr Gly Asp Asp Arg Asn Ala Thr Ala Ser Phe Ile Tyr Asp
        195                 200                 205

Gly Lys Leu Val Asp Ser Ile Gly Ser Trp Ser Gln Asn Val Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Lys Glu Gly Lys Ile Val His Ile Gly Pro Leu Ser Gly Ser Ala
            260                 265                 270

Gln His Val Glu Glu Cys Ser Cys Tyr Pro Arg Tyr Pro Asp Val Arg
        275                 280                 285

Cys Ile Cys Arg Asp Asn Trp Lys Gly Ser Asn Arg Pro Val Ile Asp
    290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Ser Ser Ser Asn Ser Asn
                325                 330                 335

Cys Arg Asp Pro Asn Asn Glu Arg Gly Asn Pro Gly Val Lys Gly Trp
            340                 345                 350

Ala Phe Asp Asn Gly Asp Asp Val Trp Met Gly Arg Thr Ile Ser Lys
        355                 360                 365

Asp Leu Arg Ser Gly Tyr Glu Thr Phe Lys Val Ile Gly Gly Trp Ser
    370                 375                 380

Thr Pro Asn Ser Lys Ser Gln Val Asn Arg Gln Val Ile Val Asp Asn
385                 390                 395                 400

Asn Asn Trp Ser Gly Tyr Ser Gly Ile Phe Ser Val Glu Gly Lys Ser
                405                 410                 415
```

```
Cys Ile Asn Arg Cys Phe Tyr Val Glu Leu Ile Arg Gly Arg Pro Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
    450                 455                 460

Asn Phe Met Pro Ile
465
```

(2) INFORMATION FOR SEQ ID NO: 21:

(i) SEQUENCE CHARACTERISTICS:
(A) LENGTH: 890 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: wild type A/Ann Arbor/6/60 (H2N2) Egg Passage 2(3)

(vii) IMMEDIATE SOURCE:
(B) CLONE: NS (ix) FEATURE:
(A) NAME/KEY: exon
(B) LOCATION: 27..56
(D) OTHER INFORMATION: /product= "nonstructural protein NS2"
/gene= "NS"
/note= "nonstructural protein NS2"
/citation= ([1][2])

(ix) FEATURE:
(A) NAME/KEY: conflict
(B) LOCATION: replace(483, "a")
(D) OTHER INFORMATION: /note= "a in ca "master" strain and in wt2(3); g in 1988 reported wild type E28-32 strain"
/citation= ([1][2])

(ix) FEATURE:
(A) NAME/KEY: exon
(B) LOCATION: 529..861
(D) OTHER INFORMATION: /product= "nonstructural protein NS2"
/gene= "NS"
/note= "nonstructural protein NS2"
/citation= ([1][2])

(ix) FEATURE:
(A) NAME/KEY: conflict
(B) LOCATION: replace(813, "g")
(D) OTHER INFORMATION: /note= "g in ca "master" strain and in wt2(3); a in 1988 reported wild type E28-32 strain"
/citation= ([1][2])

(ix) FEATURE:
(A) NAME/KEY: CDS
(B) LOCATION: join(27..56, 529..861)
(D) OTHER INFORMATION: /product= "nonstructural protein NS2"
/gene= "NS"
/note= "nonstructural protein NS2"
/citation= ([1][2])

(ix) FEATURE:
(A) NAME/KEY: CDS
(B) LOCATION: 27..677
(D) OTHER INFORMATION: /product= "nonstructural protein NS1"
/gene= "NS"
/note= "nonstructural protein NS1"
/citation= ([1][2])

(x) PUBLICATION INFORMATION:
(A) AUTHORS: Herlocher, M L
Maassab, H F
Webster, R G
(B) TITLE: Molecular and biological changes in the cold adapted master strain A/AA/6/60 (H2N2) influenza virus
(C) JOURNAL: Proceedings of the National Academy of Sciences of the USA
(G) DATE: 1993
(K) RELEVANT RESIDUES IN SEQ ID NO:21: FROM 1 TO 890

(x) PUBLICATION INFORMATION:
(A) AUTHORS: Cox, N J
Kitame, F
Kendal, A P
Maassab, H F
Naeve, C
(B) TITLE: Identification of sequence changes in the cold-adapted live attenuated influenza vaccine strain, A/Ann Arbor/6/60(H2N2)
(C) JOURNAL: Virology
(D) VOLUME: 167
(F) PAGES: 554-567
(G) DATE: 1988
(K) RELEVANT RESIDUES IN SEQ ID NO:21: FROM 1 TO 890

(xi) SEQUENCE DESCRIPTION: SEQ ID NO: 21:

```
AGCAAAAGCA GGGUGACAAA GACAUA AUG GAU CCU AAC ACU GUG UCA AGC UUU      53
                             Met Asp Pro Asn Thr Val Ser Ser Phe
                              1               5

CAG GUA GAU UGC UUC CUU UGG CAU GUC CGC AAA CAA GUU GCA GAC CAA      101
Gln Val Asp Cys Phe Leu Trp His Val Arg Lys Gln Val Ala Asp Gln
 10                  15                  20                  25

GAA CUA GGU GAU GCC CCA UUC CUU GAU CGG CUU CGC CGA GAU CAG AAG      149
Glu Leu Gly Asp Ala Pro Phe Leu Asp Arg Leu Arg Arg Asp Gln Lys
                30                  35                  40

UCC CUA AGG GGA AGA GGC AGU ACU CUC GGU CUG AAC AUC GAA ACA GCC      197
Ser Leu Arg Gly Arg Gly Ser Thr Leu Gly Leu Asn Ile Glu Thr Ala
            45                  50                  55

ACC CGU GUU GGA AAG CAG AUA GUG GAG AGG AUU CUG AAG GAA GAA UCC      245
Thr Arg Val Gly Lys Gln Ile Val Glu Arg Ile Leu Lys Glu Glu Ser
        60                  65                  70

GAU GAG GCA CUU AAA AUG ACC AUG GCC UCC GCA CCU GCU UCG CGA UAC      293
Asp Glu Ala Leu Lys Met Thr Met Ala Ser Ala Pro Ala Ser Arg Tyr
    75                  80                  85

CUA ACU GAC AUG ACU AUU GAG GAA AUG UCA AGG GAC UGG UUC AUG CUA      341
Leu Thr Asp Met Thr Ile Glu Glu Met Ser Arg Asp Trp Phe Met Leu
 90                  95                 100                 105

AUG CCC AAG CAG AAA GUG GCA GGC CCU CUU UGU AUC AGA AUG GAC CAG      389
Met Pro Lys Gln Lys Val Ala Gly Pro Leu Cys Ile Arg Met Asp Gln
               110                 115                 120

GCA AUC AUG GAU AAG AAC AUC AUA UUG AAA GCG AAU UUC AGU GUG AUU      437
Ala Ile Met Asp Lys Asn Ile Ile Leu Lys Ala Asn Phe Ser Val Ile
           125                 130                 135

UUU GAC CGG CUA GAG ACC CUA AUA UUA CUA AGG GCU UUC ACC GAA ACG      485
Phe Asp Arg Leu Glu Thr Leu Ile Leu Leu Arg Ala Phe Thr Glu Thr
       140                 145                 150

GGA GCA AUU GUU GGC GAA AUU UCA CCA UUG CCU UCU CUU CCA GGA CAU      533
Gly Ala Ile Val Gly Glu Ile Ser Pro Leu Pro Ser Leu Pro Gly His
   155                 160                 165

ACU AAU GAG GAU GUC AAA AAU GCA AUU GGG GUC CUC AUC GGA GGA CUU      581
Thr Asn Glu Asp Val Lys Asn Ala Ile Gly Val Leu Ile Gly Gly Leu
170                 175                 180                 185

GAA UGG AAU GAU AAC ACA GUU CGA GUC UCU AAA ACU CUA CAG AGA UUC      629
Glu Trp Asn Asp Asn Thr Val Arg Val Ser Lys Thr Leu Gln Arg Phe
               190                 195                 200
```

-continued

```
GCU UGG AGA AGC AGU GAU GAG AAU GGG AGA CCU CCA CUC ACU CCA AAA      677
Ala Trp Arg Ser Ser Asp Glu Asn Gly Arg Pro Pro Leu Thr Pro Lys
            205                 210                 215

UAGAAACGGA AAAUGGCGAG AACAAUUAGG UCAAAAGUUC GAAGAAAUAA GAUGGCUGAU    737

UGAAGAAGUG AGACACAAAU UGAAGAUAAC AGAGAAUAGU UUUGAGCAAA UAACAUUUAU    797

GCAAGCCUUA CAGCUGCUAU UUGAAGUGGA ACAAGAGAUA AGAACUUUCU CGUUUCAGCU    857

UAUUUAAUGA UAAAAAACAC CCUUGUUUCU ACU                                 890
```

(2) INFORMATION FOR SEQ ID NO: 22:

(i) SEQUENCE CHARACTERISTICS:
(A) LENGTH: 217 amino acids
(B) TYPE: amino acid
(D) TOPOLOGY: linear (ii) MOLECULE TYPE: protein (xi) SEQUENCE DESCRIPTION: SEQ ID NO: 22:

```
Met Asp Pro Asn Thr Val Ser Ser Phe Gln Val Asp Cys Phe Leu Trp
  1               5                  10                  15

His Val Arg Lys Gln Val Ala Asp Gln Glu Leu Gly Asp Ala Pro Phe
             20                  25                  30

Leu Asp Arg Leu Arg Arg Asp Gln Lys Ser Leu Arg Gly Arg Gly Ser
         35                  40                  45

Thr Leu Gly Leu Asn Ile Glu Thr Ala Thr Arg Val Gly Lys Gln Ile
     50                  55                  60

Val Glu Arg Ile Leu Lys Glu Glu Ser Asp Glu Ala Leu Lys Met Thr
 65                  70                  75                  80

Met Ala Ser Ala Pro Ala Ser Arg Tyr Leu Thr Asp Met Thr Ile Glu
                 85                  90                  95

Glu Met Ser Arg Asp Trp Phe Met Leu Met Pro Lys Gln Lys Val Ala
            100                 105                 110

Gly Pro Leu Cys Ile Arg Met Asp Gln Ala Ile Met Asp Lys Asn Ile
        115                 120                 125

Ile Leu Lys Ala Asn Phe Ser Val Ile Phe Asp Arg Leu Glu Thr Leu
    130                 135                 140

Ile Leu Leu Arg Ala Phe Thr Glu Thr Gly Ala Ile Val Gly Glu Ile
145                 150                 155                 160

Ser Pro Leu Pro Ser Leu Pro Gly His Thr Asn Glu Asp Val Lys Asn
                165                 170                 175

Ala Ile Gly Val Leu Ile Gly Gly Leu Glu Trp Asn Asp Asn Thr Val
            180                 185                 190

Arg Val Ser Lys Thr Leu Gln Arg Phe Ala Trp Arg Ser Ser Asp Glu
        195                 200                 205

Asn Gly Arg Pro Pro Leu Thr Pro Lys
    210                 215
```

(2) INFORMATION FOR SEQ ID NO: 23:

(i) SEQUENCE CHARACTERISTICS:
(A) LENGTH: 418 base pairs
(B) TYPE: nucleic acid
(C) STRANDEDNESS: single
(D) TOPOLOGY: linear (ii) MOLECULE TYPE: RNA (genomic)

(ix) FEATURE:
(A) NAME/KEY: CDS
(B) LOCATION: 27..389
(D) OTHER INFORMATION: /product= "Nonstructural protein 2"
/gene= "NS2"

(xi) SEQUENCE DESCRIPTION: SEQ ID NO: 23:

```
AGCAAAAGCA GGGUGACAAA GACAUA AUG GAU CCU AAC ACU GUG UCA AGC UUU      53
                             Met Asp Pro Asn Thr Val Ser Ser Phe
                               1               5

CAG GAC AUA CUA AUG AGG AUG UCA AAA AUG CAA UUG GGG UCC UCA UCG      101
Gln Asp Ile Leu Met Arg Met Ser Lys Met Gln Leu Gly Ser Ser Ser
 10                  15                  20                  25

GAG GAC UUG AAU GGA AUG AUA ACA CAG UUC GAG UCU CUA AAA CUC UAC      149
Glu Asp Leu Asn Gly Met Ile Thr Gln Phe Glu Ser Leu Lys Leu Tyr
                 30                  35                  40

AGA GAU UCG CUU GGA GAA GCA GUG AUG AGA AUG GGA GAC CUC CAC UCA      197
Arg Asp Ser Leu Gly Glu Ala Val Met Arg Met Gly Asp Leu His Ser
             45                  50                  55

CUC CAA AAU AGA AAC GGA AAA UGG CGA GAA CAA UUA GGU CAA AAG UUC      245
Leu Gln Asn Arg Asn Gly Lys Trp Arg Glu Gln Leu Gly Gln Lys Phe
         60                  65                  70

GAA GAA AUA AGA UGG CUG AUU GAA GAA GUG AGA CAC AAA UUG AAG AUA      293
Glu Glu Ile Arg Trp Leu Ile Glu Glu Val Arg His Lys Leu Lys Ile
     75                  80                  85

ACA GAG AAU AGU UUU GAG CAA AUA ACA UUU AUG CAA GCC UUA CAG CUG      341
Thr Glu Asn Ser Phe Glu Gln Ile Thr Phe Met Gln Ala Leu Gln Leu
 90                  95                 100                 105

CUA UUU GAA GUG GAA CAA GAG AUA AGA ACU UUC UCG UUU CAG CUU AUU      389
Leu Phe Glu Val Glu Gln Glu Ile Arg Thr Phe Ser Phe Gln Leu Ile
                110                 115                 120

UAAUGAUAAA AAACACCCUU GUUUCUACU                                      418
```

(2) INFORMATION FOR SEQ ID NO: 24:

(i) SEQUENCE CHARACTERISTICS:
(A) LENGTH: 121 amino acids
(B) TYPE: amino acid
(D) TOPOLOGY: linear (ii) MOLECULE TYPE: protein (xi) SEQUENCE DESCRIPTION: SEQ ID NO: 24:

```
Met Asp Pro Asn Thr Val Ser Ser Phe Gln Asp Ile Leu Met Arg Met
  1               5                  10                  15

Ser Lys Met Gln Leu Gly Ser Ser Ser Glu Asp Leu Asn Gly Met Ile
             20                  25                  30

Thr Gln Phe Glu Ser Leu Lys Leu Tyr Arg Asp Ser Leu Gly Glu Ala
         35                  40                  45

Val Met Arg Met Gly Asp Leu His Ser Leu Gln Asn Arg Asn Gly Lys
     50                  55                  60

Trp Arg Glu Gln Leu Gly Gln Lys Phe Glu Glu Ile Arg Trp Leu Ile
 65                  70                  75                  80

Glu Glu Val Arg His Lys Leu Lys Ile Thr Glu Asn Ser Phe Glu Gln
                 85                  90                  95

Ile Thr Phe Met Gln Ala Leu Gln Leu Leu Phe Glu Val Glu Gln Glu
            100                 105                 110

Ile Arg Thr Phe Ser Phe Gln Leu Ile
        115                 120
```

```
(2) INFORMATION FOR SEQ ID NO: 25:

     (i) SEQUENCE CHARACTERISTICS:
          (A) LENGTH: 1027 base pairs
          (B) TYPE: nucleic acid
          (C) STRANDEDNESS: single
          (D) TOPOLOGY: linear

    (ii) MOLECULE TYPE: RNA (genomic)

    (vi) ORIGINAL SOURCE:
          (A) ORGANISM: Influenza virus
          (B) STRAIN: wild type A/Ann Arbor/6/60 (H2N2) Egg Passage 2(3)

   (vii) IMMEDIATE SOURCE:
          (B) CLONE: M

    (ix) FEATURE:
          (A) NAME/KEY: exon
          (B) LOCATION: 26..51
          (D) OTHER INFORMATION: /product= "matrix protein M2"
               /gene= "M"
               /note= "matrix protein M2"
               /citation= ([1][2])

    (ix) FEATURE:
          (A) NAME/KEY: exon
          (B) LOCATION: 740..1004
          (D) OTHER INFORMATION: /product= "matrix protein M2"
               /gene= "M"
               /note= "matrix protein M2"
               /citation= ([1][2])

    (ix) FEATURE:
          (A) NAME/KEY: conflict
          (B) LOCATION: replace(969, "u")
          (D) OTHER INFORMATION: /note= "u in ca "master" strain and in
               wt2(3); g in 1988 reported wild type E28-32 strain"
               /citation= ([1][2])

    (ix) FEATURE:
          (A) NAME/KEY: CDS
          (B) LOCATION: join(26..51, 740..1004)
          (D) OTHER INFORMATION: /product= "matrix protein M2"
               /gene= "M"
               /note= "matrix protein M2"
               /citation= ([1][2])

    (ix) FEATURE:
          (A) NAME/KEY: CDS
          (B) LOCATION: 26..781
          (D) OTHER INFORMATION: /product= "matrix protein M1"
               /gene= "M"
               /note= "matrix protein M1"
               /citation= ([1][2])

     (x) PUBLICATION INFORMATION:
          (A) AUTHORS: Herlocher, M L
               Maassab, H F
               Webster, R G
          (B) TITLE: Molecular and biological changes in the cold
               adapted master strain A/AA/6/60 (H2N2) influenza
               virus
          (C) JOURNAL: Proceedings of the National Academy of Sciences
               of the USA
          (G) DATE: 1993
          (K) RELEVANT RESIDUES IN SEQ ID NO:25: FROM 1 TO 1027

     (x) PUBLICATION INFORMATION:
          (A) AUTHORS: Cox, N J
               Kitame, F
               Kendal, A P
               Maassab, H F
               Naeve, C
          (B) TITLE: Identification of sequence changes in the
               cold-adapted live attenuated influenza vaccine
               strain, A/Ann Arbor/6/60(H2N2)
          (C) JOURNAL: Virology
          (D) VOLUME: 167
```

(F) PAGES: 554-557
(G) DATE: 1988
(K) RELEVANT RESIDUES IN SEQ ID NO:25: FROM 1 TO 1027

(xi) SEQUENCE DESCRIPTION: SEQ ID NO: 25:

```
AGCAAAAGCA GGUAGAUAUU GAAAG AUG AGU CUU CUA ACC GAG GUC GAA ACG        52
                            Met Ser Leu Leu Thr Glu Val Glu Thr
                             1               5

UAC GUU CUC UCU AUC AUC CCG UCA GGC CCC CUC AAA GCC GAG AUC GCA       100
Tyr Val Leu Ser Ile Ile Pro Ser Gly Pro Leu Lys Ala Glu Ile Ala
 10                  15                  20                  25

CAG AGA CUU GAA GAU GUC UUU GCU GGG AAA AAC ACC GAU CUU GAG GCU       148
Gln Arg Leu Glu Asp Val Phe Ala Gly Lys Asn Thr Asp Leu Glu Ala
                 30                  35                  40

CUC AUG GAA UGG CUA AAG ACA AGA CCA AUC CUG UCA CCU CUG ACU AAG       196
Leu Met Glu Trp Leu Lys Thr Arg Pro Ile Leu Ser Pro Leu Thr Lys
             45                  50                  55

GGG AUU UUG GGA UUU GUA UUC ACG CUC ACC GUG CCC AGU GAG CGA GGA       244
Gly Ile Leu Gly Phe Val Phe Thr Leu Thr Val Pro Ser Glu Arg Gly
         60                  65                  70

CUG CAG CGU AGA CGC UUU GUC CAA AAU GCC CUC AAU GGG AAU GGG GAU       292
Leu Gln Arg Arg Arg Phe Val Gln Asn Ala Leu Asn Gly Asn Gly Asp
     75                  80                  85

CCA AAU AAC AUG GAC AGA GCA GUU AAA CUG UAU AGA AAG CUU AAG AGG       340
Pro Asn Asn Met Asp Arg Ala Val Lys Leu Tyr Arg Lys Leu Lys Arg
 90                  95                 100                 105

GAG AUA ACA UUC CAU GGG GCC AAA GAA AUA GCG CUC AGU UAU UCU GCU       388
Glu Ile Thr Phe His Gly Ala Lys Glu Ile Ala Leu Ser Tyr Ser Ala
                110                 115                 120

GGU GCA CUU GCC AGU UGU AUG GGC CUC AUA UAC AAC AGG AUG GGG GCU       436
Gly Ala Leu Ala Ser Cys Met Gly Leu Ile Tyr Asn Arg Met Gly Ala
            125                 130                 135

GUG ACC ACU GAA GUG GUC UUA GGC CUG GUA UGU GCA ACC UGU GAA CAG       484
Val Thr Thr Glu Val Val Leu Gly Leu Val Cys Ala Thr Cys Glu Gln
        140                 145                 150

AUU GCU GAC UCC CAG CAU AGG UCU CAU AGG CAA AUG GUG ACA ACA ACC       532
Ile Ala Asp Ser Gln His Arg Ser His Arg Gln Met Val Thr Thr Thr
    155                 160                 165

AAU CCA CUA AUA AGA CAU GAG AAC AGA AUG GUU CUG GCC AGC ACU ACA       580
Asn Pro Leu Ile Arg His Glu Asn Arg Met Val Leu Ala Ser Thr Thr
170                 175                 180                 185

GCU AAG GCU AUG GAG CAA AUG GCU GGA UCG AGU GAG CAA GCA GCA GAG       628
Ala Lys Ala Met Glu Gln Met Ala Gly Ser Ser Glu Gln Ala Ala Glu
                190                 195                 200

GCC AUG GAG GUU GCU AGU CAG GCC AGG CAA AUG GUG CAG GCA AUG AGA       676
Ala Met Glu Val Ala Ser Gln Ala Arg Gln Met Val Gln Ala Met Arg
            205                 210                 215

GUU AUU GGG ACU CAU CCU AGC UCC AGU GCU GGU CUA AAA AAU GAU CUU       724
Val Ile Gly Thr His Pro Ser Ser Ser Ala Gly Leu Lys Asn Asp Leu
        220                 225                 230

CUU GAA AAU UUG CAG GCC UAU CAG AAA CGA AUG GGG GUG CAG AUG CAA       772
Leu Glu Asn Leu Gln Ala Tyr Gln Lys Arg Met Gly Val Gln Met Gln
    235                 240                 245

CGA UUC AAG UGACCCUCUU GUUGUUGCCG CGAGUAUCAU UGGGAUCUUG               821
Arg Phe Lys
250

CACUUGAUAU UGUGGAUUCU UGAUCAUCUU UUUUUCAAAU GCAUUUAUCG CUUCUUUAAA     881

CACGGUCUGA AAAGAGGGCC UUCUACGGAA GGAGUACCAG AGUCUAUGAG GGAAGAAUAU     941
```

CGAAAGGAAC AGCAGAGUGC UGUGGAUUCU GACGAUAGUC AUUUUGUCAG CAUAGAGCUG 1001

GAGUAAAAAA CUACCUUGUU UCUACU 1027

(2) INFORMATION FOR SEQ ID NO: 26:

(i) SEQUENCE CHARACTERISTICS:
(A) LENGTH: 252 amino acids
(B) TYPE: amino acid
(D) TOPOLOGY: linear (ii) MOLECULE TYPE: protein (xi) SEQUENCE DESCRIPTION: SEQ ID NO: 26:

```
Met Ser Leu Leu Thr Glu Val Glu Thr Tyr Val Leu Ser Ile Ile Pro
  1               5                  10                  15

Ser Gly Pro Leu Lys Ala Glu Ile Ala Gln Arg Leu Glu Asp Val Phe
             20                  25                  30

Ala Gly Lys Asn Thr Asp Leu Glu Ala Leu Met Glu Trp Leu Lys Thr
         35                  40                  45

Arg Pro Ile Leu Ser Pro Leu Thr Lys Gly Ile Leu Gly Phe Val Phe
     50                  55                  60

Thr Leu Thr Val Pro Ser Glu Arg Gly Leu Gln Arg Arg Arg Phe Val
 65                  70                  75                  80

Gln Asn Ala Leu Asn Gly Asn Gly Asp Pro Asn Asn Met Asp Arg Ala
                 85                  90                  95

Val Lys Leu Tyr Arg Lys Leu Lys Arg Glu Ile Thr Phe His Gly Ala
            100                 105                 110

Lys Glu Ile Ala Leu Ser Tyr Ser Ala Gly Ala Leu Ala Ser Cys Met
        115                 120                 125

Gly Leu Ile Tyr Asn Arg Met Gly Ala Val Thr Thr Glu Val Val Leu
    130                 135                 140

Gly Leu Val Cys Ala Thr Cys Glu Gln Ile Ala Asp Ser Gln His Arg
145                 150                 155                 160

Ser His Arg Gln Met Val Thr Thr Thr Asn Pro Leu Ile Arg His Glu
                165                 170                 175

Asn Arg Met Val Leu Ala Ser Thr Thr Ala Lys Ala Met Glu Gln Met
            180                 185                 190

Ala Gly Ser Ser Glu Gln Ala Ala Glu Ala Met Glu Val Ala Ser Gln
        195                 200                 205

Ala Arg Gln Met Val Gln Ala Met Arg Val Ile Gly Thr His Pro Ser
    210                 215                 220

Ser Ser Ala Gly Leu Lys Asn Asp Leu Leu Glu Asn Leu Gln Ala Tyr
225                 230                 235                 240

Gln Lys Arg Met Gly Val Gln Met Gln Arg Phe Lys
                245                 250
```

(2) INFORMATION FOR SEQ ID NO: 27:

(i) SEQUENCE CHARACTERISTICS:
(A) LENGTH: 339 base pairs
(B) TYPE: nucleic acid
(C) STRANDEDNESS: single
(D) TOPOLOGY: linear (ii) MOLECULE TYPE: RNA (genomic)

(ix) FEATURE:
(A) NAME/KEY: CDS
(B) LOCATION: 26..316
(D) OTHER INFORMATION: /product= “Matrix M2”

(xi) SEQUENCE DESCRIPTION: SEQ ID NO: 27:

```
AGCAAAAGCA GGUAGAUAUU GAAAG AUG AGU CUU CUA ACC GAG GUC GAA ACG        52
                            Met Ser Leu Leu Thr Glu Val Glu Thr
                              1               5

CCU AUC AGA AAC GAA UGG GGG UGC AGA UGC AAC GAU UCA AGU GAC CCU       100
Pro Ile Arg Asn Glu Trp Gly Cys Arg Cys Asn Asp Ser Ser Asp Pro
 10                  15                  20                  25

CUU GUU GUU GCC GCG AGU AUC AUU GGG AUC UUG CAC UUG AUA UUG UGG       148
Leu Val Val Ala Ala Ser Ile Ile Gly Ile Leu His Leu Ile Leu Trp
                 30                  35                  40

AUU CUU GAU CAU CUU UUU UUC AAA UGC AUU UAU CGC UUC UUU AAA CAC       196
Ile Leu Asp His Leu Phe Phe Lys Cys Ile Tyr Arg Phe Phe Lys His
             45                  50                  55

GGU CUG AAA AGA GGG CCU UCU ACG GAA GGA GUA CCA GAG UCU AUG AGG       244
Gly Leu Lys Arg Gly Pro Ser Thr Glu Gly Val Pro Glu Ser Met Arg
         60                  65                  70

GAA GAA UAU CGA AAG GAA CAG CAG AGU GCU GUG GAU UCU GAC GAU AGU       292
Glu Glu Tyr Arg Lys Glu Gln Gln Ser Ala Val Asp Ser Asp Asp Ser
     75                  80                  85

CAU UUU GUC AGC AUA GAG CUG GAG UAAAAAACUA CCUUGUUUCU ACU             339
His Phe Val Ser Ile Glu Leu Glu
 90                  95
```

(2) INFORMATION FOR SEQ ID NO: 28:

(i) SEQUENCE CHARACTERISTICS:
(A) LENGTH: 97 amino acids
(B) TYPE: amino acid
(D) TOPOLOGY: linear (ii) MOLECULE TYPE: protein (xi) SEQUENCE DESCRIPTION: SEQ ID NO: 28:

```
Met Ser Leu Leu Thr Glu Val Glu Thr Pro Ile Arg Asn Glu Trp Gly
  1               5                  10                  15

Cys Arg Cys Asn Asp Ser Ser Asp Pro Leu Val Val Ala Ala Ser Ile
             20                  25                  30

Ile Gly Ile Leu His Leu Ile Leu Trp Ile Leu Asp His Leu Phe Phe
         35                  40                  45

Lys Cys Ile Tyr Arg Phe Phe Lys His Gly Leu Lys Arg Gly Pro Ser
     50                  55                  60

Thr Glu Gly Val Pro Glu Ser Met Arg Glu Glu Tyr Arg Lys Glu Gln
 65                  70                  75                  80

Gln Ser Ala Val Asp Ser Asp Asp Ser His Phe Val Ser Ile Glu Leu
                 85                  90                  95

Glu
```

(2) INFORMATION FOR SEQ ID NO: 29:

(i) SEQUENCE CHARACTERISTICS:
(A) LENGTH: 2341 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: wild type A/Ann Arbor/6/60 (H2N2) egg passage 2(3)

```
(vii) IMMEDIATE SOURCE:
      (B) CLONE: PB2

 (ix) FEATURE:
      (A) NAME/KEY: mutation
      (B) LOCATION: replace(141, "a")
      (D) OTHER INFORMATION: /note= "g in ca "master" strain; a in
           wt2(3); a in 1988 reported wild type E28-32 strain"
           /citation= ([1][2])

 (ix) FEATURE:
      (A) NAME/KEY: conflict
      (B) LOCATION: replace(426, "c")
      (D) OTHER INFORMATION: /note= "c in ca "master" strain and in
           wt2(3); u in 1988 reported wild type E28-32 strain"
           /citation= ([1][2])

 (ix) FEATURE:
      (A) NAME/KEY: conflict
      (B) LOCATION: replace(714, "u")
      (D) OTHER INFORMATION: /note= "u in ca "master" strain and in
           wt2(3); c in 1988 reported wild type E28-32 strain"
           /citation= ([1][2])

 (ix) FEATURE:
      (A) NAME/KEY: conflict
      (B) LOCATION: replace(821, "g")
      (D) OTHER INFORMATION: /note= "g in ca "master" strain and in
           wt2(3); a in 1988 reported wild type E28-32 strain"
           /citation= ([1][2])

 (ix) FEATURE:
      (A) NAME/KEY: conflict
      (B) LOCATION: replace(963, "g")
      (D) OTHER INFORMATION: /note= "g in ca "master" strain and in
           wt2(3); a in 1988 reported wild type E28-32 strain"
           /citation= ([1][2])

 (ix) FEATURE:
      (A) NAME/KEY: conflict
      (B) LOCATION: replace(1182, "u")
      (D) OTHER INFORMATION: /note= "u in ca "master" strain and in
           wt2(3); a in 1988 reported wild type E28-32 strain"
           /citation= ([1][2])

 (ix) FEATURE:
      (A) NAME/KEY: conflict
      (B) LOCATION: replace(1212, "u")
      (D) OTHER INFORMATION: /note= "u in ca "master" strain and in
           wt2(3); c in 1988 reported wild type E28-32 strain"
           /citation= ([1][2])

 (ix) FEATURE:
      (A) NAME/KEY: conflict
      (B) LOCATION: replace(1353, "g")
      (D) OTHER INFORMATION: /note= "g in ca "master" strain and in
           wt2(3); u in 1988 reported wild type E28-32 strain"
           /citation= ([1][2])

 (ix) FEATURE:
      (A) NAME/KEY: conflict
      (B) LOCATION: replace(1923, "g")
      (D) OTHER INFORMATION: /note= "g in ca "master" strain and in
           wt2(3); a in 1988 reported wild type E28-32 strain"
           /citation= ([1][2])

 (ix) FEATURE:
      (A) NAME/KEY: mutation
      (B) LOCATION: replace(1933, "u")
      (D) OTHER INFORMATION: /note= "c in ca "master" strain; u in
           wt2(3); u in 1988 reported wild type E28-32 strain"
           /citation= ([1][2])

 (ix) FEATURE:
      (A) NAME/KEY: CDS
      (B) LOCATION: 28..2304
      (D) OTHER INFORMATION: /product= "polymerase basic 2"
           /gene= "PB2"
           /note= "polymerase basic 2"
           /citation= ([1][2])
```

(x) PUBLICATION INFORMATION:
(A) AUTHORS: Herlocher, M L
Maassab, H F
Webster, R G
(B) TITLE: Molecular and biological changes in the cold adapted master strain A/AA/6/60 (H2N2) influenza virus
(C) JOURNAL: Proceedings of the National Academy of Sciences of the USA
(G) DATE: 1993
(K) RELEVANT RESIDUES IN SEQ ID NO:29: FROM 1 TO 2341

(x) PUBLICATION INFORMATION:
(A) AUTHORS: Cox, N J
Kitame, F
Kendal, A P
Maassab, H F
Naeve, C
(B) TITLE: Identification of sequence changes in the cold-adapted live attenuated influenza vaccine strain, A/Ann Arbor/6/60(H2N2)
(C) JOURNAL: Virology
(D) VOLUME: 167
(F) PAGES: 554-567
(G) DATE: 1988
(K) RELEVANT RESIDUES IN SEQ ID NO:29: FROM 1 TO 2341

(xi) SEQUENCE DESCRIPTION: SEQ ID NO: 29:

```
AGCGAAAGCA GGUCAAUUAU AUUCAAU AUG GAA AGA AUA AAA GAA CUA CGG         51
                              Met Glu Arg Ile Lys Glu Leu Arg
                                1               5

AAU CUG AUG UCG CAG UCU CGC ACU CGC GAG AUA CUA ACA AAA ACC ACA       99
Asn Leu Met Ser Gln Ser Arg Thr Arg Glu Ile Leu Thr Lys Thr Thr
     10                  15                  20

GUG GAC CAU AUG GCC AUA AUU AAG AAG UAC ACA UCA GGG AGA CAG GAA      147
Val Asp His Met Ala Ile Ile Lys Lys Tyr Thr Ser Gly Arg Gln Glu
 25                  30                  35                  40

AAG AAC CCG UCA CUU AGG AUG AAA UGG AUG AUG GCA AUG AAA UAU CCG      195
Lys Asn Pro Ser Leu Arg Met Lys Trp Met Met Ala Met Lys Tyr Pro
                 45                  50                  55

AUU ACA GCC GAC AAG AGG AUA ACA GAA AUG AUU CCU GAG AGA AAU GAG      243
Ile Thr Ala Asp Lys Arg Ile Thr Glu Met Ile Pro Glu Arg Asn Glu
             60                  65                  70

CAA GGG CAA ACU CUA UGG AGU AAA AUG AGU GAU GCC GGA UCG GAU CGU      291
Gln Gly Gln Thr Leu Trp Ser Lys Met Ser Asp Ala Gly Ser Asp Arg
         75                  80                  85

GUG AUG GUA UCA CCU CUG GCU GUG ACA UGG UGG AAU AGA AAU GGA CCA      339
Val Met Val Ser Pro Leu Ala Val Thr Trp Trp Asn Arg Asn Gly Pro
     90                  95                 100

AUG ACA AGU ACG GUU CAU UAU CCA AAA AUC UAC AAA ACU UAU UUU GAG      387
Met Thr Ser Thr Val His Tyr Pro Lys Ile Tyr Lys Thr Tyr Phe Glu
105                 110                 115                 120

AAA GUC GAA AGG UUA AAA CAU GGA ACC UUU GGC CCU GUC CAU UUU AGA      435
Lys Val Glu Arg Leu Lys His Gly Thr Phe Gly Pro Val His Phe Arg
                125                 130                 135

AAC CAA GUC AAA AUA CGC CGA AGA GUU GAC AUA AAU CCU GGU CAU GCA      483
Asn Gln Val Lys Ile Arg Arg Arg Val Asp Ile Asn Pro Gly His Ala
            140                 145                 150

GAC CUC AGU GCC AAG GAG GCA CAG GAU GUA AUC AUG GAA GUU GUU UUC      531
Asp Leu Ser Ala Lys Glu Ala Gln Asp Val Ile Met Glu Val Val Phe
        155                 160                 165

CCU AAC GAA GUG GGG GCC AGG AUA CUA ACG UCG GAA UCG CAA UUA ACA      579
Pro Asn Glu Val Gly Ala Arg Ile Leu Thr Ser Glu Ser Gln Leu Thr
    170                 175                 180

AUA ACC AAA GAG AAA AAA GAA GAA CUC CAG GAU UGC AAA AUU UCA CCU      627
Ile Thr Lys Glu Lys Lys Glu Glu Leu Gln Asp Cys Lys Ile Ser Pro
185                 190                 195                 200
```

-continued

```
UUG AUG GUU GCG UAC AUG UUA GAG AGA GAA CUU GUC CGA AAA ACG AGA      675
Leu Met Val Ala Tyr Met Leu Glu Arg Glu Leu Val Arg Lys Thr Arg
                205                 210                 215

UUU CUC CCA GUU GCU GGU GGA ACA AGC AGU GUG UAC AUU GAA GUG UUG      723
Phe Leu Pro Val Ala Gly Gly Thr Ser Ser Val Tyr Ile Glu Val Leu
            220                 225                 230

CAC UUG ACU CAA GGA ACA UGC UGG GAA CAG AUG UAC ACU CCA GGU GGA      771
His Leu Thr Gln Gly Thr Cys Trp Glu Gln Met Tyr Thr Pro Gly Gly
        235                 240                 245

GAA GUG AGG AAU GAU GAU GUU GAU CAA AGU CUA AUU AUU GCA GCC AGG      819
Glu Val Arg Asn Asp Asp Val Asp Gln Ser Leu Ile Ile Ala Ala Arg
    250                 255                 260

AGC AUA GUG AGA AGA GCA GCA GUA UCA GCA GAU CCA CUA GCA UCU UUA      867
Ser Ile Val Arg Arg Ala Ala Val Ser Ala Asp Pro Leu Ala Ser Leu
265                 270                 275                 280

UUG GAG AUG UGC CAC AGC ACA CAG AUU GGC GGG ACA AGG AUG GUG GAC      915
Leu Glu Met Cys His Ser Thr Gln Ile Gly Gly Thr Arg Met Val Asp
                285                 290                 295

AUU CUU AGG CAG AAC CCA ACA GAA GAG CAA GCU GUG GAA AUA UGC AAG      963
Ile Leu Arg Gln Asn Pro Thr Glu Glu Gln Ala Val Glu Ile Cys Lys
            300                 305                 310

GCU GCA AUG GGA CUG AGG AUC AGC UCA UCC UUC AGU UUU GGC GGG UUC     1011
Ala Ala Met Gly Leu Arg Ile Ser Ser Ser Phe Ser Phe Gly Gly Phe
        315                 320                 325

ACA UUU AAG AGA ACA AGC GGA UCA UCA GUC AAG AGA GAG GAA GAA GUG     1059
Thr Phe Lys Arg Thr Ser Gly Ser Ser Val Lys Arg Glu Glu Glu Val
    330                 335                 340

CUU ACG GGC AAU CUU CAA ACA UUG AAA AUA AGG GUG CAU GAG GGA UAC     1107
Leu Thr Gly Asn Leu Gln Thr Leu Lys Ile Arg Val His Glu Gly Tyr
345                 350                 355                 360

GAG GAG UUC ACA AUG GUU GGG AAA AGG GCA ACA GCU AUA CUC AGA AAA     1155
Glu Glu Phe Thr Met Val Gly Lys Arg Ala Thr Ala Ile Leu Arg Lys
                365                 370                 375

GCA ACC AGG AGA UUG AUU CAG CUG AUU GUG AGU GGA AGA GAC GAA CAG     1203
Ala Thr Arg Arg Leu Ile Gln Leu Ile Val Ser Gly Arg Asp Glu Gln
            380                 385                 390

UCG AUA GCU GAA GCA AUA AUU GUG GCC AUG GUA UUU UCA CAA GAA GAU     1251
Ser Ile Ala Glu Ala Ile Ile Val Ala Met Val Phe Ser Gln Glu Asp
        395                 400                 405

UGU AUG AUA AAA GCA GUU AGA GGU GAU CUG AAU UUC GUU AAU AGG GCA     1299
Cys Met Ile Lys Ala Val Arg Gly Asp Leu Asn Phe Val Asn Arg Ala
    410                 415                 420

AAU CAG CGA UUG AAU CCC AUG CAU CAA CUU UUA AGA CAU UUU CAG AAG     1347
Asn Gln Arg Leu Asn Pro Met His Gln Leu Leu Arg His Phe Gln Lys
425                 430                 435                 440

GAU GCG AAA GUG CUU UUU CAA AAU UGG GGA AUU GAA CAU AUC GAC AAU     1395
Asp Ala Lys Val Leu Phe Gln Asn Trp Gly Ile Glu His Ile Asp Asn
                445                 450                 455

GUG AUG GGA AUG AUU GGG GUA UUA CCA GAC AUG ACU CCA AGC ACA GAG     1443
Val Met Gly Met Ile Gly Val Leu Pro Asp Met Thr Pro Ser Thr Glu
            460                 465                 470

AUG UCA AUG AGA GGG GUA AGA GUC AGC AAA AUG GGC GUA GAU GAA UAC     1491
Met Ser Met Arg Gly Val Arg Val Ser Lys Met Gly Val Asp Glu Tyr
        475                 480                 485

UCC AGC GCG GAG AGA GUA GUG GUG AGC AUU GAC CGG UUU UUG AGA GUU     1539
Ser Ser Ala Glu Arg Val Val Val Ser Ile Asp Arg Phe Leu Arg Val
    490                 495                 500

CGA GAC CAA CGA GGA AAU GUA CUA CUA UCU CCU GAG GAG GUC AGU GAA     1587
Arg Asp Gln Arg Gly Asn Val Leu Leu Ser Pro Glu Glu Val Ser Glu
505                 510                 515                 520
```

```
ACA CAG GGA ACA GAG AAA CUG ACA AUA ACU UAC UCA UCG UCA AUG AUG      1635
Thr Gln Gly Thr Glu Lys Leu Thr Ile Thr Tyr Ser Ser Ser Met Met
                525                 530                 535

UGG GAG AUU AAU GGC CCU GAG UCA GUG UUG GUC AAU ACC UAU CAG UGG      1683
Trp Glu Ile Asn Gly Pro Glu Ser Val Leu Val Asn Thr Tyr Gln Trp
            540                 545                 550

AUC AUC AGA AAC UGG GAA ACU GUU AAA AUU CAG UGG UCU CAG AAU CCU      1731
Ile Ile Arg Asn Trp Glu Thr Val Lys Ile Gln Trp Ser Gln Asn Pro
        555                 560                 565

ACA AUG CUA UAC AAU AAA AUG GAA UUU GAG CCA UUU CAG UCU UUA GUU      1779
Thr Met Leu Tyr Asn Lys Met Glu Phe Glu Pro Phe Gln Ser Leu Val
    570                 575                 580

CCU AAG GCC AUU AGA GGC CAA UAC AGU GGG UUU GUU AGG ACU CUA UUC      1827
Pro Lys Ala Ile Arg Gly Gln Tyr Ser Gly Phe Val Arg Thr Leu Phe
585                 590                 595                 600

CAA CAA AUG AGG GAU GUA CUU GGG ACA UUU GAU ACC ACC CAG AUA AUA      1875
Gln Gln Met Arg Asp Val Leu Gly Thr Phe Asp Thr Thr Gln Ile Ile
                605                 610                 615

AAA CUU CUU CCC UUU GCA GCC GCC CCA CCA AAG CAA AGU AGA AUG CAG      1923
Lys Leu Leu Pro Phe Ala Ala Ala Pro Pro Lys Gln Ser Arg Met Gln
            620                 625                 630

UUC UCU UCA UUG ACU GUG AAU GUG AGG GGA UCA GGA AUG AGA AUA CUU      1971
Phe Ser Ser Leu Thr Val Asn Val Arg Gly Ser Gly Met Arg Ile Leu
        635                 640                 645

GUA AGG GGC AAU UCU CCU AUA UUC AAC UAC AAC AAG ACC ACU AAG AGA      2019
Val Arg Gly Asn Ser Pro Ile Phe Asn Tyr Asn Lys Thr Thr Lys Arg
    650                 655                 660

CUA ACA AUU CUC GGA AAG GAU GCU GGC ACU UUA ACU GAA GAC CCA GAU      2067
Leu Thr Ile Leu Gly Lys Asp Ala Gly Thr Leu Thr Glu Asp Pro Asp
665                 670                 675                 680

GAA GGC ACA UCU GGA GUG GAG UCC GCU GUU CUG AGA GGA UUC CUC AUU      2115
Glu Gly Thr Ser Gly Val Glu Ser Ala Val Leu Arg Gly Phe Leu Ile
                685                 690                 695

CUG GGC AAA GAA GAU AGG AGA UAU GGA CCA GCA UUA AGC AUC AAU GAA      2163
Leu Gly Lys Glu Asp Arg Arg Tyr Gly Pro Ala Leu Ser Ile Asn Glu
            700                 705                 710

CUG AGU AAC CUU GCG AAA GGA GAA AAG GCU AAU GUA CUA AUU GGG CAA      2211
Leu Ser Asn Leu Ala Lys Gly Glu Lys Ala Asn Val Leu Ile Gly Gln
        715                 720                 725

GGA GAC GUG GUG UUG GUA AUG AAA CGA AAA CGG AAC UCU AGC AUA CUU      2259
Gly Asp Val Val Leu Val Met Lys Arg Lys Arg Asn Ser Ser Ile Leu
    730                 735                 740

ACU GAC AGC CAG ACA GCG ACC AAA AGG AUU CGG AUG GCC AUC AAU          2304
Thr Asp Ser Gln Thr Ala Thr Lys Arg Ile Arg Met Ala Ile Asn
745                 750                 755

UAAUGUUGAA UAGUUUAAAA ACGACCUUGU UUCUACU                             2341
```

(2) INFORMATION FOR SEQ ID NO: 30:

(i) SEQUENCE CHARACTERISTICS:
(A) LENGTH: 759 amino acids
(B) TYPE: amino acid
(D) TOPOLOGY: linear (ii) MOLECULE TYPE: protein (xi) SEQUENCE DESCRIPTION: SEQ ID NO: 30:

```
Met Glu Arg Ile Lys Glu Leu Arg Asn Leu Met Ser Gln Ser Arg Thr
  1               5                  10                  15

Arg Glu Ile Leu Thr Lys Thr Thr Val Asp His Met Ala Ile Ile Lys
             20                  25                  30
```

```
Lys Tyr Thr Ser Gly Arg Gln Glu Lys Asn Pro Ser Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Ser Asp Ala Gly Ser Asp Arg Val Met Val Ser Pro Leu Ala Val
                85                  90                  95

Thr Trp Trp Asn Arg Asn Gly Pro Met Thr Ser Thr Val His Tyr Pro
            100                 105                 110

Lys Ile Tyr Lys Thr Tyr Phe Glu Lys Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175

Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Arg Asn Asp Asp Val Asp
                245                 250                 255

Gln Ser Leu Ile Ile Ala Ala Arg Ser Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Thr Arg Met Val Asp Ile Leu Arg Gln Asn Pro Thr Glu
    290                 295                 300

Glu Gln Ala Val Glu Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Lys
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Ile Glu His Ile Asp Asn Val Met Gly Met Ile Gly Val Leu
    450                 455                 460
```

-continued

```
Pro Asp Met Thr Pro Ser Thr Glu Met Ser Met Arg Gly Val Arg Val
465                 470                 475                 480

Ser Lys Met Gly Val Asp Glu Tyr Ser Ser Ala Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605

Thr Phe Asp Thr Thr Gln Ile Ile Lys Leu Leu Pro Phe Ala Ala Ala
    610                 615                 620

Pro Pro Lys Gln Ser Arg Met Gln Phe Ser Ser Leu Thr Val Asn Val
625                 630                 635                 640

Arg Gly Ser Gly Met Arg Ile Leu Val Arg Gly Asn Ser Pro Ile Phe
                645                 650                 655

Asn Tyr Asn Lys Thr Thr Lys Arg Leu Thr Ile Leu Gly Lys Asp Ala
            660                 665                 670

Gly Thr Leu Thr Glu Asp Pro Asp Glu Gly Thr Ser Gly Val Glu Ser
        675                 680                 685

Ala Val Leu Arg Gly Phe Leu Ile Leu Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asn Ser Ser Ile Leu Thr Asp Ser Gln Thr Ala Thr Lys
            740                 745                 750

Arg Ile Arg Met Ala Ile Asn
        755
```

(2) INFORMATION FOR SEQ ID NO: 31:

(i) SEQUENCE CHARACTERISTICS:
(A) LENGTH: 2341 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: wild type A/Ann Arbor/6/60 (H2N2) Egg Passage 2(3)

(vii) IMMEDIATE SOURCE:
(B) CLONE: PB1

-continued (ix) FEATURE:
(A) NAME/KEY: conflict
(B) LOCATION: replace(123, "g")
(D) OTHER INFORMATION: /note= "g in ca "master" strain and in wt2(3); a in 1988 reported wild type E28-32 strain"
/citation= ([1][2])

(ix) FEATURE:
(A) NAME/KEY: conflict
(B) LOCATION: replace(486, "u")
(D) OTHER INFORMATION: /note= "u in ca "master" strain and in wt2(3); c in 1988 reported wild type E28-32 strain"
/citation= ([1][2])

(ix) FEATURE:
(A) NAME/KEY: conflict
(B) LOCATION: replace(1195, "g")
(D) OTHER INFORMATION: /note= "g in ca "master" strain and in wt2(3); a in 1988 reported wild type E28-32 strain"
/citation= ([1][2])

(ix) FEATURE:
(A) NAME/KEY: mutation
(B) LOCATION: replace(1276, "a")
(D) OTHER INFORMATION: /note= "g in ca "master" strain; a in wt2(3); g in 1988 reported wild type E28-32 strain"
/citation= ([1][2])

(ix) FEATURE:
(A) NAME/KEY: conflict
(B) LOCATION: replace(1395, "u")
(D) OTHER INFORMATION: /note= "u in ca "master" strain and in wt2(3); g in 1988 reported wild type E28-32 strain"
/citation= ([1][2])

(ix) FEATURE:
(A) NAME/KEY: conflict
(B) LOCATION: replace(1766, "g")
(D) OTHER INFORMATION: /note= "g in ca "master" strain and in wt2(3); a in 1988 reported wild type E28-32 strain"
/citation= ([1][2])

(ix) FEATURE:
(A) NAME/KEY: conflict
(B) LOCATION: replace(2005, "a")
(D) OTHER INFORMATION: /note= "a in ca "master" strain and in wt2(3); g in 1988 reported wild type E28-32 strain"
/citation= ([1][2])

(ix) FEATURE:
(A) NAME/KEY: conflict
(B) LOCATION: replace(2019, "u")
(D) OTHER INFORMATION: /note= "u in ca "master" strain and in wt2(3); c in 1988 reported wild type E28-32 strain"
/citation= ([1][2])

(ix) FEATURE:
(A) NAME/KEY: CDS
(B) LOCATION: 25..2295
(D) OTHER INFORMATION: /product= "polymerase basic 1"
/gene= "PB1"
/note= "polymerase basic 1"
/citation= ([1][2])

(x) PUBLICATION INFORMATION:
(A) AUTHORS: Herlocher, M L
Maassab, H F
Webster, R G
(B) TITLE: Molecular and biological changes in the cold adapted master strain A/AA/6/60 (H2N2) influenza virus
(C) JOURNAL: Proceedings of the National Academy of Sciences of the USA
(G) DATE: 1993
(K) RELEVANT RESIDUES IN SEQ ID NO:31: FROM 1 TO 2341

(x) PUBLICATION INFORMATION:
(A) AUTHORS: Cox, N J
Kitame, F
Kendal, A P
Maassab, H F
Naeve, C
(B) TITLE: Identification of sequence changes in the cold-adapted live attenuated influenza vaccine strain
(C) JOURNAL: Virology
(D) VOLUME: 167
(F) PAGES: 554-567
(G) DATE: 1988
(K) RELEVANT RESIDUES IN SEQ ID NO:31: FROM 1 TO 2341

(xi) SEQUENCE DESCRIPTION: SEQ ID NO: 31:

```
AGCGAAAGCA GGCAAACCAU UUGA AUG GAU GUC AAU CCG ACC UUA CUU UUC        51
                           Met Asp Val Asn Pro Thr Leu Leu Phe
                            1               5

UUG AAA GUU CCA GCG CAA AAU GCC AUA AGU ACU ACA UUC CCU UAU ACU       99
Leu Lys Val Pro Ala Gln Asn Ala Ile Ser Thr Thr Phe Pro Tyr Thr
 10                 15                  20                  25

GGA GAU CCU CCA UAC AGC CAU GGG ACA GGA ACA GGA UAC ACC AUG GAC      147
Gly Asp Pro Pro Tyr Ser His Gly Thr Gly Thr Gly Tyr Thr Met Asp
                30                  35                  40

ACA GUC AAC AGA ACA CAU CAA UAU UCA GAA AAG GGG AAG UGG ACA ACA      195
Thr Val Asn Arg Thr His Gln Tyr Ser Glu Lys Gly Lys Trp Thr Thr
            45                  50                  55

AAC ACG GAA ACU GGA GCG CAC CAA CUU AAC CCA AUU GAU GGA CCA CUA      243
Asn Thr Glu Thr Gly Ala His Gln Leu Asn Pro Ile Asp Gly Pro Leu
        60                  65                  70

CCU GAG GAC AAU GAA CCA AGU GGA UAU GCA CAA ACA GAC UGC GUC CUG      291
Pro Glu Asp Asn Glu Pro Ser Gly Tyr Ala Gln Thr Asp Cys Val Leu
    75                  80                  85

GAA GCA AUG GCU UUC CUU GAA GAA UCC CAC CCA GGA AUC UUU GAA AAC      339
Glu Ala Met Ala Phe Leu Glu Glu Ser His Pro Gly Ile Phe Glu Asn
 90                 95                 100                 105

UCG UGU CUU GAA ACG AUG GAA GUU AUU CAA CAA ACA AGA GUG GAC AAA      387
Ser Cys Leu Glu Thr Met Glu Val Ile Gln Gln Thr Arg Val Asp Lys
                110                 115                 120

CUG ACC CAA GGU CGU CAG ACC UAU GAU UGG ACA UUG AAC AGA AAU CAG      435
Leu Thr Gln Gly Arg Gln Thr Tyr Asp Trp Thr Leu Asn Arg Asn Gln
            125                 130                 135

CCG GCU GCA ACU GCG CUA GCC AAC ACU AUA GAG GUC UUC AGA UCG AAU      483
Pro Ala Ala Thr Ala Leu Ala Asn Thr Ile Glu Val Phe Arg Ser Asn
        140                 145                 150

GGU CUG ACA GCU AAU GAA UCG GGA AGG CUA AUA GAU UUC CUC AAG GAU      531
Gly Leu Thr Ala Asn Glu Ser Gly Arg Leu Ile Asp Phe Leu Lys Asp
    155                 160                 165

GUG AUA GAA UCA AUG GAU AAA GAG GAG AUG GAA AUC ACA ACA CAC UUC      579
Val Ile Glu Ser Met Asp Lys Glu Glu Met Glu Ile Thr Thr His Phe
170                 175                 180                 185

CAA AGA AAA AGA AGA GUA AGA GAC AAC AUG ACC AAG AAA AUG GUC ACA      627
Gln Arg Lys Arg Arg Val Arg Asp Asn Met Thr Lys Lys Met Val Thr
                190                 195                 200

CAA CGA ACA AUA GGA AAG AAG AAG CAA AGA UUG AAC AAG AGA AGC UAU      675
Gln Arg Thr Ile Gly Lys Lys Lys Gln Arg Leu Asn Lys Arg Ser Tyr
            205                 210                 215

CUA AUA AGA GCA CUG ACA UUG AAC ACA AUG ACU AAA GAU GCA GAG AGA      723
Leu Ile Arg Ala Leu Thr Leu Asn Thr Met Thr Lys Asp Ala Glu Arg
        220                 225                 230

GGU AAA UUA AAG AGA AGA GCA AUU GCA ACA CCC GGU AUG CAG AUC AGA      771
Gly Lys Leu Lys Arg Arg Ala Ile Ala Thr Pro Gly Met Gln Ile Arg
    235                 240                 245
```

-continued

```
GGG UUC GUG UAC UUU GUC GAA ACA CUA GCG AGA AGU AUU UGU GAG AAG      819
Gly Phe Val Tyr Phe Val Glu Thr Leu Ala Arg Ser Ile Cys Glu Lys
250                 255                 260                 265

CUU GAA CAG UCU GGG CUU CCG GUU GGA GGU AAU GAA AAG AAG GCU AAA      867
Leu Glu Gln Ser Gly Leu Pro Val Gly Gly Asn Glu Lys Lys Ala Lys
                270                 275                 280

CUG GCA AAU GUU GUG CGA AAA AUG AUG ACU AAU UCA CAA GAC ACA GAG      915
Leu Ala Asn Val Val Arg Lys Met Met Thr Asn Ser Gln Asp Thr Glu
            285                 290                 295

CUC UCU UUC ACA AUU ACU GGA GAC AAU ACC AAA UGG AAU GAG AAU CAA      963
Leu Ser Phe Thr Ile Thr Gly Asp Asn Thr Lys Trp Asn Glu Asn Gln
        300                 305                 310

AAU CCU CGG AUG UUC CUG GCG AUG AUA ACA UAC AUC ACA AGA AAU CAA     1011
Asn Pro Arg Met Phe Leu Ala Met Ile Thr Tyr Ile Thr Arg Asn Gln
    315                 320                 325

CCU GAA UGG UUU AGA AAC GUC CUG AGC AUC GCA CCU AUA AUG UUC UCA     1059
Pro Glu Trp Phe Arg Asn Val Leu Ser Ile Ala Pro Ile Met Phe Ser
330                 335                 340                 345

AAU AAA AUG GCA AGA CUA GGG AAA GGA UAC AUG UUC AAA AGC AAG AGC     1107
Asn Lys Met Ala Arg Leu Gly Lys Gly Tyr Met Phe Lys Ser Lys Ser
                350                 355                 360

AUG AAG CUC CGA ACA CAA AUA CCA GCA GAA AUG CUA GCA AGU AUU GAC     1155
Met Lys Leu Arg Thr Gln Ile Pro Ala Glu Met Leu Ala Ser Ile Asp
            365                 370                 375

CUG AAA UAC UUU AAU GAA UCA ACA AGA AAG AAA AUC GAG GAA AUA AGG     1203
Leu Lys Tyr Phe Asn Glu Ser Thr Arg Lys Lys Ile Glu Glu Ile Arg
        380                 385                 390

CCU CUC CUA AUA GAU GGC ACA GUC UCA UUG AGU CCU GGA AUG AUG AUG     1251
Pro Leu Leu Ile Asp Gly Thr Val Ser Leu Ser Pro Gly Met Met Met
    395                 400                 405

GGC AUG UUC AAC AUG CUA AGU ACA AUC UUA GGA GUC UCA AUC CUG AAU     1299
Gly Met Phe Asn Met Leu Ser Thr Ile Leu Gly Val Ser Ile Leu Asn
410                 415                 420                 425

CUU GGA CAA AAG AAG UAC ACC AAA ACA ACA UAC UGG UGG GAC GGA CUC     1347
Leu Gly Gln Lys Lys Tyr Thr Lys Thr Thr Tyr Trp Trp Asp Gly Leu
                430                 435                 440

CAA UCC UCU GAU GAC UUC GCC CUC AUA GUG AAU GCA CCA AAU CAU GAU     1395
Gln Ser Ser Asp Asp Phe Ala Leu Ile Val Asn Ala Pro Asn His Asp
            445                 450                 455

GGA AUA CAA GCA GGG GUG GAU AGA UUC UAC AGA ACC UGC AAG CUA GUC     1443
Gly Ile Gln Ala Gly Val Asp Arg Phe Tyr Arg Thr Cys Lys Leu Val
        460                 465                 470

GGA AUC AAU AUG AGC AAA AAG AAG UCC UAC AUA AAU AGG ACA GGG ACA     1491
Gly Ile Asn Met Ser Lys Lys Lys Ser Tyr Ile Asn Arg Thr Gly Thr
    475                 480                 485

UUU GAA UUC ACA AGC UUU UUC UAU CGC UAU GGA UUU GUA GCC AAU UUU     1539
Phe Glu Phe Thr Ser Phe Phe Tyr Arg Tyr Gly Phe Val Ala Asn Phe
490                 495                 500                 505

AGC AUG GAG CUG CCC AGC UUU GGA GUG UCU GGA AUU AAU GAA UCG GCU     1587
Ser Met Glu Leu Pro Ser Phe Gly Val Ser Gly Ile Asn Glu Ser Ala
                510                 515                 520

GAU AUG AGC AUU GGG GUA ACA GUG AUA AAG AAC AAC AUG AUA AAC AAU     1635
Asp Met Ser Ile Gly Val Thr Val Ile Lys Asn Asn Met Ile Asn Asn
            525                 530                 535

GAC CUU GGG CCA GCA ACA GCC CAA CUG GCU CUU CAA CUA UUC AUC AAA     1683
Asp Leu Gly Pro Ala Thr Ala Gln Leu Ala Leu Gln Leu Phe Ile Lys
        540                 545                 550

GAC UAC AGA UAU ACG UAC CGG UGC CAC AGA GGA GAC ACA CAA AUU CAG     1731
Asp Tyr Arg Tyr Thr Tyr Arg Cys His Arg Gly Asp Thr Gln Ile Gln
    555                 560                 565
```

```
ACA AGG AGA UCA UUC GAG CUA AAG AAG CUG UGG GGG CAA ACC CGC UCA      1779
Thr Arg Arg Ser Phe Glu Leu Lys Lys Leu Trp Gly Gln Thr Arg Ser
570                 575                 580                 585

AAG GCA GGA CUU UUG GUU UCG GAU GGA GGA CCA AAC UUA UAC AAU AUC      1827
Lys Ala Gly Leu Leu Val Ser Asp Gly Gly Pro Asn Leu Tyr Asn Ile
                590                 595                 600

CGG AAU CUC CAC AUU CCA GAA GUC UGC UUG AAG UGG GAG CUA AUG GAU      1875
Arg Asn Leu His Ile Pro Glu Val Cys Leu Lys Trp Glu Leu Met Asp
            605                 610                 615

GAA GAC UAU CAG GGG AGG CUU UGU AAU CCC CUG AAU CCA UUU GUC AGU      1923
Glu Asp Tyr Gln Gly Arg Leu Cys Asn Pro Leu Asn Pro Phe Val Ser
        620                 625                 630

CAU AAG GAG AUU GAG UCU GUA AAC AAU GCU GUG GUA AUG CCA GCU CAC      1971
His Lys Glu Ile Glu Ser Val Asn Asn Ala Val Val Met Pro Ala His
    635                 640                 645

GGU CCA GCC AAG AGC AUG GAA UAU GAU GCU GUU ACU ACU ACA CAC UCU      2019
Gly Pro Ala Lys Ser Met Glu Tyr Asp Ala Val Thr Thr Thr His Ser
650                 655                 660                 665

UGG AUC CCU AAG AGG AAC CGC UCC AUU CUC AAC ACA AGC CAA AGG GGA      2067
Trp Ile Pro Lys Arg Asn Arg Ser Ile Leu Asn Thr Ser Gln Arg Gly
                670                 675                 680

AUU CUU GAA GAU GAA CAG AUG UAU CAG AAG UGU UGC AAU CUA UUC GAG      2115
Ile Leu Glu Asp Glu Gln Met Tyr Gln Lys Cys Cys Asn Leu Phe Glu
            685                 690                 695

AAA UUC UUC CCU AGC AGU UCG UAC AGG AGA CCA GUU GGA AUU UCC AGC      2163
Lys Phe Phe Pro Ser Ser Ser Tyr Arg Arg Pro Val Gly Ile Ser Ser
        700                 705                 710

AUG GUG GAG GCC AUG GUG UCU AGG GCC CGG AUU GAU GCA CGG AUU GAC      2211
Met Val Glu Ala Met Val Ser Arg Ala Arg Ile Asp Ala Arg Ile Asp
    715                 720                 725

UUC GAG UCU GGA CGG AUU AAG AAA GAG GAG UUC GCU GAG AUC AUG AAG      2259
Phe Glu Ser Gly Arg Ile Lys Lys Glu Glu Phe Ala Glu Ile Met Lys
730                 735                 740                 745

AUC UGU UCC ACC AUU GAA GAG CUC AGA CGG CAA AAA UAGUGAAUUU           2305
Ile Cys Ser Thr Ile Glu Glu Leu Arg Arg Gln Lys
                750                 755

AGCUUGUCCU UCAUGAAAAA AUGCCUUGUU UCUACU                              2341
```

(2) INFORMATION FOR SEQ ID NO: 32:

(i) SEQUENCE CHARACTERISTICS:
(A) LENGTH: 757 amino acids
(B) TYPE: amino acid
(D) TOPOLOGY: linear (ii) MOLECULE TYPE: protein (xi) SEQUENCE DESCRIPTION: SEQ ID NO: 32:

```
Met Asp Val Asn Pro Thr Leu Leu Phe Leu Lys Val Pro Ala Gln Asn
  1               5                  10                  15

Ala Ile Ser Thr Thr Phe Pro Tyr Thr Gly Asp Pro Pro Tyr Ser His
            20                  25                  30

Gly Thr Gly Thr Gly Tyr Thr Met Asp Thr Val Asn Arg Thr His Gln
        35                  40                  45

Tyr Ser Glu Lys Gly Lys Trp Thr Thr Asn Thr Glu Thr Gly Ala His
     50                  55                  60

Gln Leu Asn Pro Ile Asp Gly Pro Leu Pro Glu Asp Asn Glu Pro Ser
 65                  70                  75                  80

Gly Tyr Ala Gln Thr Asp Cys Val Leu Glu Ala Met Ala Phe Leu Glu
                 85                  90                  95
```

-continued

```
Glu Ser His Pro Gly Ile Phe Glu Asn Ser Cys Leu Glu Thr Met Glu
            100                 105                 110

Val Ile Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
    130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Ile Glu Ser Met Asp Lys
                165                 170                 175

Glu Glu Met Glu Ile Thr Thr His Phe Gln Arg Lys Arg Arg Val Arg
            180                 185                 190

Asp Asn Met Thr Lys Lys Met Val Thr Gln Arg Thr Ile Gly Lys Lys
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Phe Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Ile Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Lys Ser Lys Ser Met Lys Leu Arg Thr Gln Ile
        355                 360                 365

Pro Ala Glu Met Leu Ala Ser Ile Asp Leu Lys Tyr Phe Asn Glu Ser
    370                 375                 380

Thr Arg Lys Lys Ile Glu Glu Ile Arg Pro Leu Leu Ile Asp Gly Thr
385                 390                 395                 400

Val Ser Leu Ser Pro Gly Met Met Met Gly Met Phe Asn Met Leu Ser
                405                 410                 415

Thr Ile Leu Gly Val Ser Ile Leu Asn Leu Gly Gln Lys Lys Tyr Thr
            420                 425                 430

Lys Thr Thr Tyr Trp Trp Asp Gly Leu Gln Ser Ser Asp Asp Phe Ala
        435                 440                 445

Leu Ile Val Asn Ala Pro Asn His Asp Gly Ile Gln Ala Gly Val Asp
    450                 455                 460

Arg Phe Tyr Arg Thr Cys Lys Leu Val Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
            500                 505                 510

Gly Val Ser Gly Ile Asn Glu Ser Ala Asp Met Ser Ile Gly Val Thr
        515                 520                 525
```

-continued

```
Val Ile Lys Asn Asn Met Ile Asn Asn Asp Leu Gly Pro Ala Thr Ala
    530                 535                 540

Gln Leu Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Leu
                565                 570                 575

Lys Lys Leu Trp Gly Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
        595                 600                 605

Val Cys Leu Lys Trp Glu Leu Met Asp Glu Asp Tyr Gln Gly Arg Leu
    610                 615                 620

Cys Asn Pro Leu Asn Pro Phe Val Ser His Lys Glu Ile Glu Ser Val
625                 630                 635                 640

Asn Asn Ala Val Val Met Pro Ala His Gly Pro Ala Lys Ser Met Glu
                645                 650                 655

Tyr Asp Ala Val Thr Thr Thr His Ser Trp Ile Pro Lys Arg Asn Arg
            660                 665                 670

Ser Ile Leu Asn Thr Ser Gln Arg Gly Ile Leu Glu Asp Glu Gln Met
        675                 680                 685

Tyr Gln Lys Cys Cys Asn Leu Phe Glu Lys Phe Phe Pro Ser Ser Ser
    690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Ala Glu Ile Met Lys Ile Cys Ser Thr Ile Glu Glu
            740                 745                 750

Leu Arg Arg Gln Lys
        755
```

(2) INFORMATION FOR SEQ ID NO: 33:

(i) SEQUENCE CHARACTERISTICS:
(A) LENGTH: 2233 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: wild type A/Ann Arbor/6/60 (H2N2) Egg Passage 2(3)

(vii) IMMEDIATE SOURCE:
(B) CLONE: PA (ix) FEATURE:
(A) NAME/KEY: conflict
(B) LOCATION: replace(20, "c")
(D) OTHER INFORMATION: /note= "c in ca "master" strain and in wt2(3); u in 1988 reported wild type E28-32 strain" /citation= ([1][2])

(ix) FEATURE:
(A) NAME/KEY: conflict
(B) LOCATION: replace(75, "g")
(D) OTHER INFORMATION: /note= "g in ca "master" strain and in wt2(3); u in 1988 reported wild type E28-32 strain" /citation= ([1][2])

```
    (ix) FEATURE:
          (A) NAME/KEY: conflict
          (B) LOCATION: replace(1861, "g")
          (D) OTHER INFORMATION: /note= "g in ca "master" strain and in
               wt2(3); a in 1988 reported wild type E28-32 strain"
               /citation= ([1][2])

    (ix) FEATURE:
          (A) NAME/KEY: conflict
          (B) LOCATION: replace(2167..2168, "cc")
          (D) OTHER INFORMATION: /note= "cc in ca "master" strain and in
               wt2(3); uu in 1988 reported wild type E28-32 strain"
               /citation= ([1][2])

    (ix) FEATURE:
          (A) NAME/KEY: CDS
          (B) LOCATION: 25..2172
          (D) OTHER INFORMATION: /product= "polymerase acidic
               protein"
               /gene= "PA"
               /note= "polymerase acidic protein"
               /citation= ([1][2])

     (x) PUBLICATION INFORMATION:
          (A) AUTHORS: Herlocher, M L
               Maassab, H F
               Webster, R G
          (B) TITLE: Molecular and biological changes in the cold
               adapted master strain A/AA/6/60 (H2N2) influenza
               virus
          (C) JOURNAL: Proceedings of the National Academy of Sciences
               of the USA
          (G) DATE: 1993
          (K) RELEVANT RESIDUES IN SEQ ID NO:33: FROM 1 TO 2233

     (x) PUBLICATION INFORMATION:
          (A) AUTHORS: Cox, N J
               Kitame, F
               Kendal, A P
               Maassab, H F
               Naeve, C
          (B) TITLE: Identification of sequence changes in the
               cold-adapted live attenuated influenza strain,
               A/Ann Arbor/6/60(H2N2)
          (C) JOURNAL: Virology
          (D) VOLUME: 167
          (F) PAGES: 554-567
          (G) DATE: 1988
          (K) RELEVANT RESIDUES IN SEQ ID NO:33: FROM 1 TO 2233

    (xi) SEQUENCE DESCRIPTION: SEQ ID NO: 33:

AGCGAAAGCA GGUACUGAUC CGAA AUG GAA GAU UUU GUG CGA CAA UGC UUC        51
                           Met Glu Asp Phe Val Arg Gln Cys Phe
                             1               5

AAU CCG AUG AUU GUC GAG CUU GCG GAA AAA GCA AUG AAA GAG UAU GGA       99
Asn Pro Met Ile Val Glu Leu Ala Glu Lys Ala Met Lys Glu Tyr Gly
 10                  15                  20                  25

GAG GAU CUG AAA AUC GAA ACA AAC AAA UUU GCA GCA AUA UGC ACU CAC      147
Glu Asp Leu Lys Ile Glu Thr Asn Lys Phe Ala Ala Ile Cys Thr His
                 30                  35                  40

UUG GAA GUA UGC UUC AUG UAU UCA GAU UUU CAU UUC AUC AAU GAG CAA      195
Leu Glu Val Cys Phe Met Tyr Ser Asp Phe His Phe Ile Asn Glu Gln
             45                  50                  55

GGC GAG UCA AUA AUA GUA GAG CUU GAU GAU CCA AAU GCA CUU UUG AAG      243
Gly Glu Ser Ile Ile Val Glu Leu Asp Asp Pro Asn Ala Leu Leu Lys
         60                  65                  70

CAC AGA UUU GAA AUA AUA GAG GGA AGA GAU CGC ACA AUG GCC UGG ACA      291
His Arg Phe Glu Ile Ile Glu Gly Arg Asp Arg Thr Met Ala Trp Thr
     75                  80                  85

GUA GUA AAC AGU AUU UGC AAC ACU ACA GGA GCU GAG AAA CCG AAG UUU      339
Val Val Asn Ser Ile Cys Asn Thr Thr Gly Ala Glu Lys Pro Lys Phe
 90                  95                 100                 105
```

-continued

```
CUG CCA GAU UUG UAU GAU UAC AAG GAG AAU AGA UUC AUC GAG AUU GGA      387
Leu Pro Asp Leu Tyr Asp Tyr Lys Glu Asn Arg Phe Ile Glu Ile Gly
                110                 115                 120

GUG ACA AGG AGG GAA GUC CAC AUA UAC UAU CUU GAA AAG GCC AAU AAA      435
Val Thr Arg Arg Glu Val His Ile Tyr Tyr Leu Glu Lys Ala Asn Lys
            125                 130                 135

AUU AAA UCU GAG AAG ACA CAC AUC CAC AUU UUC UCA UUC ACU GGG GAA      483
Ile Lys Ser Glu Lys Thr His Ile His Ile Phe Ser Phe Thr Gly Glu
        140                 145                 150

GAA AUG GCC ACA AAG GCC GAC UAC ACU CUC GAU GAG GAA AGC AGG GCU      531
Glu Met Ala Thr Lys Ala Asp Tyr Thr Leu Asp Glu Glu Ser Arg Ala
    155                 160                 165

AGG AUC AAA ACC AGA CUA UUC ACC AUA AGA CAA GAA AUG GCU AGC AGA      579
Arg Ile Lys Thr Arg Leu Phe Thr Ile Arg Gln Glu Met Ala Ser Arg
170                 175                 180                 185

GGC CUC UGG GAU UCC UUU CAU CAG UCC GAA AGA GGC GAA GAA ACA AUU      627
Gly Leu Trp Asp Ser Phe His Gln Ser Glu Arg Gly Glu Glu Thr Ile
                190                 195                 200

GAA GAA AGA UUU GAA AUC ACA GGG ACA AUG CGC AGG CUC GCC GAC CAA      675
Glu Glu Arg Phe Glu Ile Thr Gly Thr Met Arg Arg Leu Ala Asp Gln
            205                 210                 215

AGU CUC CCG CCG AAC UUC UCC UGC CUU GAG AAU UUU AGA GCC UAU GUG      723
Ser Leu Pro Pro Asn Phe Ser Cys Leu Glu Asn Phe Arg Ala Tyr Val
        220                 225                 230

GAU GGA UUC GAA CCG AAC GGC UAC AUU GAG GGC AAG CUU UCU CAA AUG      771
Asp Gly Phe Glu Pro Asn Gly Tyr Ile Glu Gly Lys Leu Ser Gln Met
    235                 240                 245

UCC AAA GAA GUA AAU GCU AAA AUU GAA CCU UUU CUG AAA ACA ACA CCA      819
Ser Lys Glu Val Asn Ala Lys Ile Glu Pro Phe Leu Lys Thr Thr Pro
250                 255                 260                 265

AGA CCA AUU AGA CUU CCG GAU GGG CCU CCU UGU UCU CAG CGG UCC AAA      867
Arg Pro Ile Arg Leu Pro Asp Gly Pro Pro Cys Ser Gln Arg Ser Lys
                270                 275                 280

UUC CUG CUG AUG GAU GCU UUA AAA UUA AGC AUU GAG GAC CCA AGU CAC      915
Phe Leu Leu Met Asp Ala Leu Lys Leu Ser Ile Glu Asp Pro Ser His
            285                 290                 295

GAA GGA GAG GGA AUA CCA CUA UAU GAU GCG AUC AAG UGU AUG AGA ACA      963
Glu Gly Glu Gly Ile Pro Leu Tyr Asp Ala Ile Lys Cys Met Arg Thr
        300                 305                 310

UUC UUU GGA UGG AAA GAA CCC UAU GUU GUU AAA CCA CAC GAA AAG GGA     1011
Phe Phe Gly Trp Lys Glu Pro Tyr Val Val Lys Pro His Glu Lys Gly
    315                 320                 325

AUA AAU CCA AAU UAU CUG CUG UCA UGG AAG CAA GUA CUG GCA GAA CUG     1059
Ile Asn Pro Asn Tyr Leu Leu Ser Trp Lys Gln Val Leu Ala Glu Leu
330                 335                 340                 345

CAG GAC AUU GAG AAU GAG GAG AAG AUU CCA AGA ACC AAA AAC AUG AAG     1107
Gln Asp Ile Glu Asn Glu Glu Lys Ile Pro Arg Thr Lys Asn Met Lys
                350                 355                 360

AAA ACG AGU CAG CUA AAG UGG GCA CUU GGU GAG AAC AUG GCA CCA GAG     1155
Lys Thr Ser Gln Leu Lys Trp Ala Leu Gly Glu Asn Met Ala Pro Glu
            365                 370                 375

AAG GUA GAC UUU GAC GAC UGU AGA GAU GUA AGC GAU UUG AAG CAA UAU     1203
Lys Val Asp Phe Asp Asp Cys Arg Asp Val Ser Asp Leu Lys Gln Tyr
        380                 385                 390

GAU AGU GAU GAA CCU GAA UUA AGG UCA CUU UCA AGC UGG AUC CAG AAU     1251
Asp Ser Asp Glu Pro Glu Leu Arg Ser Leu Ser Ser Trp Ile Gln Asn
    395                 400                 405

GAG UUC AAC AAG GCA UGC GAG CUG ACC GAU UCA AUC UGG AUA GAG CUC     1299
Glu Phe Asn Lys Ala Cys Glu Leu Thr Asp Ser Ile Trp Ile Glu Leu
410                 415                 420                 425
```

-continued

```
GAU GAG AUU GGA GAA GAU GUG GCU CCA AUU GAA CAC AUU GCA AGC AUG      1347
Asp Glu Ile Gly Glu Asp Val Ala Pro Ile Glu His Ile Ala Ser Met
                430                 435                 440

AGA AGG AAU UAC UUC ACA GCA GAG GUG UCU CAU UGC AGA GCC ACA GAA      1395
Arg Arg Asn Tyr Phe Thr Ala Glu Val Ser His Cys Arg Ala Thr Glu
            445                 450                 455

UAU AUA AUG AAG GGG GUA UAC AUU AAU ACU GCC UUG CUU AAU GCA UCC      1443
Tyr Ile Met Lys Gly Val Tyr Ile Asn Thr Ala Leu Leu Asn Ala Ser
        460                 465                 470

UGU GCA GCA AUG GAC GAU UUC CAA CUA AUU CCC AUG AUA AGC AAA UGU      1491
Cys Ala Ala Met Asp Asp Phe Gln Leu Ile Pro Met Ile Ser Lys Cys
    475                 480                 485

AGA ACU AAA GAG GGA AGG CGA AAG ACC AAU UUA UAU GGU UUC AUC AUA      1539
Arg Thr Lys Glu Gly Arg Arg Lys Thr Asn Leu Tyr Gly Phe Ile Ile
490                 495                 500                 505

AAA GGA AGA UCU CAC UUA AGG AAU GAC ACC GAC GUG GUA AAC UUU GUG      1587
Lys Gly Arg Ser His Leu Arg Asn Asp Thr Asp Val Val Asn Phe Val
                510                 515                 520

AGC AUG GAG UUU UCU CUC ACU GAC CCA AGA CUU GAG CCA CAC AAA UGG      1635
Ser Met Glu Phe Ser Leu Thr Asp Pro Arg Leu Glu Pro His Lys Trp
            525                 530                 535

GAG AAG UAC UGU GUU CUU GAG AUA GGA GAU AUG CUA CUA AGA AGU GCC      1683
Glu Lys Tyr Cys Val Leu Glu Ile Gly Asp Met Leu Leu Arg Ser Ala
        540                 545                 550

AUA GGC CAG GUG UCA AGG CCC AUG UUC UUG UAU GUG AGG ACA AAU GGA      1731
Ile Gly Gln Val Ser Arg Pro Met Phe Leu Tyr Val Arg Thr Asn Gly
    555                 560                 565

ACA UCA AAG AUU AAA AUG AAA UGG GGA AUG GAG AUG AGG CGU UGC CUC      1779
Thr Ser Lys Ile Lys Met Lys Trp Gly Met Glu Met Arg Arg Cys Leu
570                 575                 580                 585

CUU CAG UCA CUC CAA CAA AUC GAG AGU AUG AUU GAA GCC GAG UCC UCU      1827
Leu Gln Ser Leu Gln Gln Ile Glu Ser Met Ile Glu Ala Glu Ser Ser
                590                 595                 600

GUC AAG GAG AAA GAC AUG ACC AAA GAG UUU UUC GAG AAU AAA UCA GAA      1875
Val Lys Glu Lys Asp Met Thr Lys Glu Phe Phe Glu Asn Lys Ser Glu
            605                 610                 615

ACA UGG CCC AUU GGA GAG UCC CCC AAA GGA GUG GAA GAA GGU UCC AUU      1923
Thr Trp Pro Ile Gly Glu Ser Pro Lys Gly Val Glu Glu Gly Ser Ile
        620                 625                 630

GGG AAG GUC UGC AGG ACU UUA UUA GCC AAG UCG GUA UUC AAU AGC CUG      1971
Gly Lys Val Cys Arg Thr Leu Leu Ala Lys Ser Val Phe Asn Ser Leu
    635                 640                 645

UAU GCA UCU CCA CAA UUA GAA GGA UUU UCA GCU GAA UCA AGA AAA CUG      2019
Tyr Ala Ser Pro Gln Leu Glu Gly Phe Ser Ala Glu Ser Arg Lys Leu
650                 655                 660                 665

CUU CUU GUC GUU CAG GCU CUU AGG GAC AAU CUU GAA CCU GGG ACC UUU      2067
Leu Leu Val Val Gln Ala Leu Arg Asp Asn Leu Glu Pro Gly Thr Phe
                670                 675                 680

GAU CUU GGG GGG CUA UAU GAA GCA AUU GAG GAG UGC CUG AUU AAU GAU      2115
Asp Leu Gly Gly Leu Tyr Glu Ala Ile Glu Glu Cys Leu Ile Asn Asp
            685                 690                 695

CCC UGG GUU UUG CUU AAU GCG UCU UGG UUC AAC UCC UUC CUA ACA CAU      2163
Pro Trp Val Leu Leu Asn Ala Ser Trp Phe Asn Ser Phe Leu Thr His
        700                 705                 710

GCA CCA AGA UAGUUGUGGC AAUGCUACUA UUUGCUAUCC AUACUGUCCA              2212
Ala Pro Arg
    715

AAAAAGUACC UUGUUUCUAC U                                              2233
```

(2) INFORMATION FOR SEQ ID NO: 34:

(i) SEQUENCE CHARACTERISTICS:
(A) LENGTH: 716 amino acids
(B) TYPE: amino acid
(D) TOPOLOGY: linear (ii) MOLECULE TYPE: protein (xi) SEQUENCE DESCRIPTION: SEQ ID NO: 34:

```
Met Glu Asp Phe Val Arg Gln Cys Phe Asn Pro Met Ile Val Glu Leu
  1               5                  10                  15

Ala Glu Lys Ala Met Lys Glu Tyr Gly Glu Asp Leu Lys Ile Glu Thr
             20                  25                  30

Asn Lys Phe Ala Ala Ile Cys Thr His Leu Glu Val Cys Phe Met Tyr
         35                  40                  45

Ser Asp Phe His Phe Ile Asn Glu Gln Gly Glu Ser Ile Ile Val Glu
     50                  55                  60

Leu Asp Asp Pro Asn Ala Leu Leu Lys His Arg Phe Glu Ile Ile Glu
 65                  70                  75                  80

Gly Arg Asp Arg Thr Met Ala Trp Thr Val Val Asn Ser Ile Cys Asn
                 85                  90                  95

Thr Thr Gly Ala Glu Lys Pro Lys Phe Leu Pro Asp Leu Tyr Asp Tyr
            100                 105                 110

Lys Glu Asn Arg Phe Ile Glu Ile Gly Val Thr Arg Arg Glu Val His
        115                 120                 125

Ile Tyr Tyr Leu Glu Lys Ala Asn Lys Ile Lys Ser Glu Lys Thr His
    130                 135                 140

Ile His Ile Phe Ser Phe Thr Gly Glu Glu Met Ala Thr Lys Ala Asp
145                 150                 155                 160

Tyr Thr Leu Asp Glu Glu Ser Arg Ala Arg Ile Lys Thr Arg Leu Phe
                165                 170                 175

Thr Ile Arg Gln Glu Met Ala Ser Arg Gly Leu Trp Asp Ser Phe His
            180                 185                 190

Gln Ser Glu Arg Gly Glu Glu Thr Ile Glu Glu Arg Phe Glu Ile Thr
        195                 200                 205

Gly Thr Met Arg Arg Leu Ala Asp Gln Ser Leu Pro Pro Asn Phe Ser
    210                 215                 220

Cys Leu Glu Asn Phe Arg Ala Tyr Val Asp Gly Phe Glu Pro Asn Gly
225                 230                 235                 240

Tyr Ile Glu Gly Lys Leu Ser Gln Met Ser Lys Glu Val Asn Ala Lys
                245                 250                 255

Ile Glu Pro Phe Leu Lys Thr Thr Pro Arg Pro Ile Arg Leu Pro Asp
            260                 265                 270

Gly Pro Pro Cys Ser Gln Arg Ser Lys Phe Leu Leu Met Asp Ala Leu
        275                 280                 285

Lys Leu Ser Ile Glu Asp Pro Ser His Glu Gly Glu Gly Ile Pro Leu
    290                 295                 300

Tyr Asp Ala Ile Lys Cys Met Arg Thr Phe Phe Gly Trp Lys Glu Pro
305                 310                 315                 320

Tyr Val Val Lys Pro His Glu Lys Gly Ile Asn Pro Asn Tyr Leu Leu
                325                 330                 335

Ser Trp Lys Gln Val Leu Ala Glu Leu Gln Asp Ile Glu Asn Glu Glu
            340                 345                 350

Lys Ile Pro Arg Thr Lys Asn Met Lys Lys Thr Ser Gln Leu Lys Trp
        355                 360                 365
```

```
Ala Leu Gly Glu Asn Met Ala Pro Glu Lys Val Asp Phe Asp Asp Cys
    370                 375                 380

Arg Asp Val Ser Asp Leu Lys Gln Tyr Asp Ser Asp Glu Pro Glu Leu
385                 390                 395                 400

Arg Ser Leu Ser Ser Trp Ile Gln Asn Glu Phe Asn Lys Ala Cys Glu
                405                 410                 415

Leu Thr Asp Ser Ile Trp Ile Glu Leu Asp Glu Ile Gly Glu Asp Val
            420                 425                 430

Ala Pro Ile Glu His Ile Ala Ser Met Arg Arg Asn Tyr Phe Thr Ala
        435                 440                 445

Glu Val Ser His Cys Arg Ala Thr Glu Tyr Ile Met Lys Gly Val Tyr
    450                 455                 460

Ile Asn Thr Ala Leu Leu Asn Ala Ser Cys Ala Ala Met Asp Asp Phe
465                 470                 475                 480

Gln Leu Ile Pro Met Ile Ser Lys Cys Arg Thr Lys Glu Gly Arg Arg
                485                 490                 495

Lys Thr Asn Leu Tyr Gly Phe Ile Ile Lys Gly Arg Ser His Leu Arg
            500                 505                 510

Asn Asp Thr Asp Val Val Asn Phe Val Ser Met Glu Phe Ser Leu Thr
        515                 520                 525

Asp Pro Arg Leu Glu Pro His Lys Trp Glu Lys Tyr Cys Val Leu Glu
    530                 535                 540

Ile Gly Asp Met Leu Leu Arg Ser Ala Ile Gly Gln Val Ser Arg Pro
545                 550                 555                 560

Met Phe Leu Tyr Val Arg Thr Asn Gly Thr Ser Lys Ile Lys Met Lys
                565                 570                 575

Trp Gly Met Glu Met Arg Arg Cys Leu Leu Gln Ser Leu Gln Gln Ile
            580                 585                 590

Glu Ser Met Ile Glu Ala Glu Ser Ser Val Lys Glu Lys Asp Met Thr
        595                 600                 605

Lys Glu Phe Phe Glu Asn Lys Ser Glu Thr Trp Pro Ile Gly Glu Ser
    610                 615                 620

Pro Lys Gly Val Glu Glu Gly Ser Ile Gly Lys Val Cys Arg Thr Leu
625                 630                 635                 640

Leu Ala Lys Ser Val Phe Asn Ser Leu Tyr Ala Ser Pro Gln Leu Glu
                645                 650                 655

Gly Phe Ser Ala Glu Ser Arg Lys Leu Leu Leu Val Val Gln Ala Leu
            660                 665                 670

Arg Asp Asn Leu Glu Pro Gly Thr Phe Asp Leu Gly Gly Leu Tyr Glu
        675                 680                 685

Ala Ile Glu Glu Cys Leu Ile Asn Asp Pro Trp Val Leu Leu Asn Ala
    690                 695                 700

Ser Trp Phe Asn Ser Phe Leu Thr His Ala Pro Arg
705                 710                 715
```

(2) INFORMATION FOR SEQ ID NO: 35:

(i) SEQUENCE CHARACTERISTICS:
- (A) LENGTH: 1773 base pairs
- (B) TYPE: nucleic acid
- (C) STRANDEDNESS: single
- (D) TOPOLOGY: linear (ii) MOLECULE TYPE: RNA (genomic)

(vi) ORIGINAL SOURCE:
- (A) ORGANISM: Influenza virus
- (B) STRAIN: wild type A/Ann Arbor/6/60 (H2N2) Egg Passage 2(3)

```
   (vii) IMMEDIATE SOURCE:
          (B) CLONE: HA

    (ix) FEATURE:
          (A) NAME/KEY: mutation
          (B) LOCATION: replace(144, "a")
          (D) OTHER INFORMATION: /gene= "HA"
               /note= "u in ca "master" strain; a in wt2(3)"
               /citation= ([1])

    (ix) FEATURE:
          (A) NAME/KEY: mutation
          (B) LOCATION: replace(455, "g")
          (D) OTHER INFORMATION: /gene= "HA"
               /note= "a in ca "master" strain; g in wt2(3)"
               /citation= ([1])

    (ix) FEATURE:
          (A) NAME/KEY: mutation
          (B) LOCATION: replace(729, "a")
          (D) OTHER INFORMATION: /gene= "HA"
               /note= "c in ca "master" strain; a in wt2(3)"
               /citation= ([1])

    (ix) FEATURE:
          (A) NAME/KEY: CDS
          (B) LOCATION: 44..1729
          (D) OTHER INFORMATION: /product= "hemagglutinin"
               /gene= "HA"
               /note= "hemagglutinin protein"
               /citation= ([1])

     (x) PUBLICATION INFORMATION:
          (A) AUTHORS: Herlocher, M L
               Maassab, H F
               Webster, R G
          (B) TITLE: Molecular and biological changes in the cold
               adapted master strain A/AA/6/60 (H2N2) influenza
               virus
          (C) JOURNAL: Proceedings of the National Academy of Sciences
               of the USA
          (G) DATE: 1993
          (K) RELEVANT RESIDUES IN SEQ ID NO:35: FROM 1 TO 1773

    (xi) SEQUENCE DESCRIPTION: SEQ ID NO: 35:

AGCAAAAGCA GGGGUUAUAC CAUAGACAAC CAAAAGCAAA ACA AUG GCC AUC AUU       55
                                                Met Ala Ile Ile
                                                  1

UAU CUC AUU CUC CUG UUC ACA GCA GUG AGA GGG GAC AAG AUA UGC AUU      103
Tyr Leu Ile Leu Leu Phe Thr Ala Val Arg Gly Asp Lys Ile Cys Ile
  5                  10                  15                  20

GGA UAC CAU GCC AAU AAU UCC ACA GAG ACG GUC GAC ACA AAU CUA GAG      151
Gly Tyr His Ala Asn Asn Ser Thr Glu Thr Val Asp Thr Asn Leu Glu
                 25                  30                  35

CGG AAC GUC ACU GUG ACU CAU GCC AAG GAC AUU CUU GAG AAG ACC CAU      199
Arg Asn Val Thr Val Thr His Ala Lys Asp Ile Leu Glu Lys Thr His
             40                  45                  50

AAC GGA AAG UUA UGC AAA CUA AAC GGA AUC CCU CCA CUU GAA CUA GGG      247
Asn Gly Lys Leu Cys Lys Leu Asn Gly Ile Pro Pro Leu Glu Leu Gly
         55                  60                  65

GAC UGU AGC AUU GCC GGA UGG CUC CUU GGA AAU CCA GAA UGU GAU AGG      295
Asp Cys Ser Ile Ala Gly Trp Leu Leu Gly Asn Pro Glu Cys Asp Arg
     70                  75                  80

CUU CUA AGU GUG CCA GAA UGG UCC UAU AUA AUG GAG AAA GAA AAC CCG      343
Leu Leu Ser Val Pro Glu Trp Ser Tyr Ile Met Glu Lys Glu Asn Pro
 85                  90                  95                 100

AGA AAC GGU UUG UGU UAU CCA GGC AAC UUC AAU GAU UAU GAA GAA UUG      391
Arg Asn Gly Leu Cys Tyr Pro Gly Asn Phe Asn Asp Tyr Glu Glu Leu
                105                 110                 115
```

-continued

```
AAA CAU CUC CUC AGC AGC GUG AAA CAU UUC GAG AAA GUA AAG AUU CUG       439
Lys His Leu Leu Ser Ser Val Lys His Phe Glu Lys Val Lys Ile Leu
            120                 125                 130

CCC AAA GAU AGA UGG GCA CAG CAU ACA ACA ACU GGA GGU UCA CAG GCC       487
Pro Lys Asp Arg Trp Ala Gln His Thr Thr Thr Gly Gly Ser Gln Ala
        135                 140                 145

UGC GCG GUG UCU GGU AAU CCA UCA UUC UUC AGG AAC AUG GUC UGG CUG       535
Cys Ala Val Ser Gly Asn Pro Ser Phe Phe Arg Asn Met Val Trp Leu
    150                 155                 160

ACA GAG GAA GGA UCA AAU UAU CCG GUU GCC AAA GGA UCG UAC AAC AAU       583
Thr Glu Glu Gly Ser Asn Tyr Pro Val Ala Lys Gly Ser Tyr Asn Asn
165                 170                 175                 180

ACA AGC GGA GAA CAA AUG CUA AUA AUU UGG GGG GUG CAC CAU CCC AUU       631
Thr Ser Gly Glu Gln Met Leu Ile Ile Trp Gly Val His His Pro Ile
                185                 190                 195

GAU GAG ACA GAA CAA AGA ACA UUG UAC CAG AAU GUG GGA ACC UAU GUU       679
Asp Glu Thr Glu Gln Arg Thr Leu Tyr Gln Asn Val Gly Thr Tyr Val
            200                 205                 210

UCC GUA GGC ACA UCA ACA UUG AAC AAA AGG UCA ACC CCA GAA AUA GCA       727
Ser Val Gly Thr Ser Thr Leu Asn Lys Arg Ser Thr Pro Glu Ile Ala
        215                 220                 225

AAA AGG CCU AAA GUG AAU GGA CUA GGA AGU AGA AUG GAA UUC UCU UGG       775
Lys Arg Pro Lys Val Asn Gly Leu Gly Ser Arg Met Glu Phe Ser Trp
    230                 235                 240

ACC CUC UUG GAU AUG UGG GAC ACC AUA AAU UUU GAG AGU ACU GGU AAU       823
Thr Leu Leu Asp Met Trp Asp Thr Ile Asn Phe Glu Ser Thr Gly Asn
245                 250                 255                 260

CUA AUU GCA CCA GAG UAU GGA UUC AAA AUA UCG AAA AGA GGU AGU UCU       871
Leu Ile Ala Pro Glu Tyr Gly Phe Lys Ile Ser Lys Arg Gly Ser Ser
                265                 270                 275

GGG AUC AUG AAA ACA GAA GGA ACA CUU GAG AAC UGU GAG ACC AAA UGC       919
Gly Ile Met Lys Thr Glu Gly Thr Leu Glu Asn Cys Glu Thr Lys Cys
            280                 285                 290

CAA ACU CCU UUG GGA GCA AUA AAU ACA ACA UUG CCU UUU CAC AAU GUC       967
Gln Thr Pro Leu Gly Ala Ile Asn Thr Thr Leu Pro Phe His Asn Val
        295                 300                 305

CAC CCA CUG ACA AUA GGU GAG UGC CCC AAA UAU GUA AAA UCG GAG AAG      1015
His Pro Leu Thr Ile Gly Glu Cys Pro Lys Tyr Val Lys Ser Glu Lys
    310                 315                 320

UUG GUC UUA GCA ACA GGA CUA AGG AAU GUU CCC CAG AUU GAA UCA AGA      1063
Leu Val Leu Ala Thr Gly Leu Arg Asn Val Pro Gln Ile Glu Ser Arg
325                 330                 335                 340

GGA UUG UUU GGG GCA AUA GCU GGU UUU AUA GAA GGA GGA UGG CAA GGA      1111
Gly Leu Phe Gly Ala Ile Ala Gly Phe Ile Glu Gly Gly Trp Gln Gly
                345                 350                 355

AUG GUU GAU GGU UGG UAU GGA UAC CAU CAC AGC AAU GAC CAG GGA UCA      1159
Met Val Asp Gly Trp Tyr Gly Tyr His His Ser Asn Asp Gln Gly Ser
            360                 365                 370

GGG UAU GCA GCA GAC AAA GAA UCC ACU CAA AAG GCA UUU GAU GGA AUC      1207
Gly Tyr Ala Ala Asp Lys Glu Ser Thr Gln Lys Ala Phe Asp Gly Ile
        375                 380                 385

ACC AAC AAG GUA AAU UCU GUG AUU GAA AAG AUA AAC ACC CAA UUU GAA      1255
Thr Asn Lys Val Asn Ser Val Ile Glu Lys Ile Asn Thr Gln Phe Glu
    390                 395                 400

GCU GUU GGG AAA GAA UUC AGU AAC UUA GAG AGA AGA CUG GAG AAC UUG      1303
Ala Val Gly Lys Glu Phe Ser Asn Leu Glu Arg Arg Leu Glu Asn Leu
405                 410                 415                 420

AAC AAA AAG AUG GAA GAC GGG UUU CUA GAU GUG UGG ACA UAC AAU GCU      1351
Asn Lys Lys Met Glu Asp Gly Phe Leu Asp Val Trp Thr Tyr Asn Ala
                425                 430                 435
```

-continued

```
GAG CUU CUA GUU CUG AUG GAA AAU GAG AGG ACA CUU GAC UUU CAU GAU      1399
Glu Leu Leu Val Leu Met Glu Asn Glu Arg Thr Leu Asp Phe His Asp
            440                 445                 450

UCU AAU GUC AAG AAU CUG UAU GAU AAA GUC AGA AUG CAG CUG AGG GAC      1447
Ser Asn Val Lys Asn Leu Tyr Asp Lys Val Arg Met Gln Leu Arg Asp
        455                 460                 465

AAC GUC AAA GAA CUA GGA AAU GGA UGU UUU GAA UUU UAU CAC AAA UGU      1495
Asn Val Lys Glu Leu Gly Asn Gly Cys Phe Glu Phe Tyr His Lys Cys
    470                 475                 480

GAU GAU GAA UGC AUG AAU AGU GUG AAA AAC GGG ACA UAU GAU UAU CCC      1543
Asp Asp Glu Cys Met Asn Ser Val Lys Asn Gly Thr Tyr Asp Tyr Pro
485                 490                 495                 500

AAG UAU GAA GAA GAG UCU AAA CUA AAU AGA AAU GAA AUU AAA GGG GUA      1591
Lys Tyr Glu Glu Glu Ser Lys Leu Asn Arg Asn Glu Ile Lys Gly Val
                505                 510                 515

AAA UUG AGC AGC AUG GGG GUU UGU CGG AUC CUU GCC AUU UAU GCU ACA      1639
Lys Leu Ser Ser Met Gly Val Cys Arg Ile Leu Ala Ile Tyr Ala Thr
            520                 525                 530

GUA GCA GGU UCU CUG UCA CUG GCA AUC AUG AUG GCU GGG AUC UCU UUC      1687
Val Ala Gly Ser Leu Ser Leu Ala Ile Met Met Ala Gly Ile Ser Phe
        535                 540                 545

UGG AUG UGC UCC AAC GGG UCU CUG CAG UGC AGG AUC UGC AUA              1729
Trp Met Cys Ser Asn Gly Ser Leu Gln Cys Arg Ile Cys Ile
    550                 555                 560

UGAUUAUAAG UCAUUUUAUA AUUAAAAACA CCCUUGUUUC UACU                     1773
```

(2) INFORMATION FOR SEQ ID NO: 36:

(i) SEQUENCE CHARACTERISTICS:
(A) LENGTH: 562 amino acids
(B) TYPE: amino acid
(D) TOPOLOGY: linear (ii) MOLECULE TYPE: protein (xi) SEQUENCE DESCRIPTION: SEQ ID NO: 36:

```
Met Ala Ile Ile Tyr Leu Ile Leu Leu Phe Thr Ala Val Arg Gly Asp
  1               5                  10                  15

Lys Ile Cys Ile Gly Tyr His Ala Asn Asn Ser Thr Glu Thr Val Asp
             20                  25                  30

Thr Asn Leu Glu Arg Asn Val Thr Val Thr His Ala Lys Asp Ile Leu
         35                  40                  45

Glu Lys Thr His Asn Gly Lys Leu Cys Lys Leu Asn Gly Ile Pro Pro
     50                  55                  60

Leu Glu Leu Gly Asp Cys Ser Ile Ala Gly Trp Leu Leu Gly Asn Pro
 65                  70                  75                  80

Glu Cys Asp Arg Leu Leu Ser Val Pro Glu Trp Ser Tyr Ile Met Glu
                 85                  90                  95

Lys Glu Asn Pro Arg Asn Gly Leu Cys Tyr Pro Gly Asn Phe Asn Asp
            100                 105                 110

Tyr Glu Glu Leu Lys His Leu Leu Ser Ser Val Lys His Phe Glu Lys
        115                 120                 125

Val Lys Ile Leu Pro Lys Asp Arg Trp Ala Gln His Thr Thr Thr Gly
    130                 135                 140

Gly Ser Gln Ala Cys Ala Val Ser Gly Asn Pro Ser Phe Phe Arg Asn
145                 150                 155                 160
```

```
Met Val Trp Leu Thr Glu Glu Gly Ser Asn Tyr Pro Val Ala Lys Gly
                165                 170                 175

Ser Tyr Asn Asn Thr Ser Gly Glu Gln Met Leu Ile Ile Trp Gly Val
            180                 185                 190

His His Pro Ile Asp Glu Thr Glu Gln Arg Thr Leu Tyr Gln Asn Val
        195                 200                 205

Gly Thr Tyr Val Ser Val Gly Thr Ser Thr Leu Asn Lys Arg Ser Thr
    210                 215                 220

Pro Glu Ile Ala Lys Arg Pro Lys Val Asn Gly Leu Gly Ser Arg Met
225                 230                 235                 240

Glu Phe Ser Trp Thr Leu Leu Asp Met Trp Asp Thr Ile Asn Phe Glu
                245                 250                 255

Ser Thr Gly Asn Leu Ile Ala Pro Glu Tyr Gly Phe Lys Ile Ser Lys
            260                 265                 270

Arg Gly Ser Ser Gly Ile Met Lys Thr Glu Gly Thr Leu Glu Asn Cys
        275                 280                 285

Glu Thr Lys Cys Gln Thr Pro Leu Gly Ala Ile Asn Thr Thr Leu Pro
    290                 295                 300

Phe His Asn Val His Pro Leu Thr Ile Gly Glu Cys Pro Lys Tyr Val
305                 310                 315                 320

Lys Ser Glu Lys Leu Val Leu Ala Thr Gly Leu Arg Asn Val Pro Gln
                325                 330                 335

Ile Glu Ser Arg Gly Leu Phe Gly Ala Ile Ala Gly Phe Ile Glu Gly
            340                 345                 350

Gly Trp Gln Gly Met Val Asp Gly Trp Tyr Gly Tyr His His Ser Asn
        355                 360                 365

Asp Gln Gly Ser Gly Tyr Ala Ala Asp Lys Glu Ser Thr Gln Lys Ala
    370                 375                 380

Phe Asp Gly Ile Thr Asn Lys Val Asn Ser Val Ile Glu Lys Ile Asn
385                 390                 395                 400

Thr Gln Phe Glu Ala Val Gly Lys Glu Phe Ser Asn Leu Glu Arg Arg
                405                 410                 415

Leu Glu Asn Leu Asn Lys Lys Met Glu Asp Gly Phe Leu Asp Val Trp
            420                 425                 430

Thr Tyr Asn Ala Glu Leu Leu Val Leu Met Glu Asn Glu Arg Thr Leu
        435                 440                 445

Asp Phe His Asp Ser Asn Val Lys Asn Leu Tyr Asp Lys Val Arg Met
    450                 455                 460

Gln Leu Arg Asp Asn Val Lys Glu Leu Gly Asn Gly Cys Phe Glu Phe
465                 470                 475                 480

Tyr His Lys Cys Asp Asp Glu Cys Met Asn Ser Val Lys Asn Gly Thr
                485                 490                 495

Tyr Asp Tyr Pro Lys Tyr Glu Glu Glu Ser Lys Leu Asn Arg Asn Glu
            500                 505                 510

Ile Lys Gly Val Lys Leu Ser Ser Met Gly Val Cys Arg Ile Leu Ala
        515                 520                 525

Ile Tyr Ala Thr Val Ala Gly Ser Leu Ser Leu Ala Ile Met Met Ala
    530                 535                 540

Gly Ile Ser Phe Trp Met Cys Ser Asn Gly Ser Leu Gln Cys Arg Ile
545                 550                 555                 560

Cys Ile
```

(2) INFORMATION FOR SEQ ID NO: 37:

(i) SEQUENCE CHARACTERISTICS:
(A) LENGTH: 1467 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: wild type A/Ann Arbor/6/60 (H2N2) Egg Passage 2(3)

(vii) IMMEDIATE SOURCE:
(B) CLONE: NA (ix) FEATURE:
(A) NAME/KEY: mutation
(B) LOCATION: replace(394, "c")
(D) OTHER INFORMATION: /product= "Neuraminidase"
/gene= "NA"
/note= "u in ca "master" strain; c in wt2(3)"
/citation= ([1])

(ix) FEATURE:
(A) NAME/KEY: mutation
(B) LOCATION: replace(604, "a")
(D) OTHER INFORMATION: /product= "Neuraminidase"
/gene= "NA"
/note= "u in ca "master" strain; a in wt2(3)"
/citation= ([1])

(ix) FEATURE:
(A) NAME/KEY: CDS
(B) LOCATION: 20..1426
(D) OTHER INFORMATION: /product= "neuraminidase"
/gene= "NA"
/note= "neuraminidase protein"
/citation= ([1])

(x) PUBLICATION INFORMATION:
(A) AUTHORS: Herlocher, M L
Maassab, H F
Webster, R G
(B) TITLE: Molecular and biological changes in the cold adapted master strain A/AA/6/60 (H2N2) Influenza Virus
(C) JOURNAL: Proceedings of the National Academy of Sciences of the USA
(G) DATE: 1993
(K) RELEVANT RESIDUES IN SEQ ID NO:37: FROM 1 TO 1467

(xi) SEQUENCE DESCRIPTION: SEQ ID NO: 37:

```
AGCAAAAGCA GGAGUGAAA AUG AAU CCA AAU CAA AAG ACA AUA ACA AUU GGC      52
                     Met Asn Pro Asn Gln Lys Thr Ile Thr Ile Gly
                       1               5                   10

UCU GUC UCU CUC ACC AUC GCA ACA GUA UGC UUC CUC AUG CAG AUU GCC      100
Ser Val Ser Leu Thr Ile Ala Thr Val Cys Phe Leu Met Gln Ile Ala
             15                  20                  25

AUC CUG GCA ACU ACU GUG ACA UUG CAC CUU AAG CAA CAU GAG UGC GAC      148
Ile Leu Ala Thr Thr Val Thr Leu His Leu Lys Gln His Glu Cys Asp
         30                  35                  40

UCC CCC GCG AGC AAC CAA GUA AUG CCA UGU GAA CCA AUA AUA AUA GAA      196
Ser Pro Ala Ser Asn Gln Val Met Pro Cys Glu Pro Ile Ile Ile Glu
     45                  50                  55

AGG AAC AUA ACA GAG AUA GUG UAU UUG AAU AAC ACC ACC AUA GAG AAA      244
Arg Asn Ile Thr Glu Ile Val Tyr Leu Asn Asn Thr Thr Ile Glu Lys
 60                  65                  70                  75

GAG AUU UGC CCC GAA GUA GUG GGA UAC AGA AAU UGG UCA AAG CCG CAA      292
Glu Ile Cys Pro Glu Val Val Gly Tyr Arg Asn Trp Ser Lys Pro Gln
                 80                  85                  90
```

-continued

```
UGU CAA AUU ACA GGA UUU GCA CCU UUU UCU AAG GAC AAU UCA AUC CGG      340
Cys Gln Ile Thr Gly Phe Ala Pro Phe Ser Lys Asp Asn Ser Ile Arg
             95                 100                 105

CUU UCU GCU GGU GGG GAC AUU UGG GUG ACG AGA GAA CCU UAU GUG UCA      388
Leu Ser Ala Gly Gly Asp Ile Trp Val Thr Arg Glu Pro Tyr Val Ser
        110                 115                 120

UGC GAC CCU GGC AAG UGU UAU CAA UUU GCA CUC GGG CAG GGG ACC ACA      436
Cys Asp Pro Gly Lys Cys Tyr Gln Phe Ala Leu Gly Gln Gly Thr Thr
    125                 130                 135

CUA GAC AAC AAA CAU UCA AAU GGC ACA AUA CAU GAU AGA AUC CCU CAU      484
Leu Asp Asn Lys His Ser Asn Gly Thr Ile His Asp Arg Ile Pro His
140                 145                 150                 155

CGA ACC CUA UUA AUG AAU GAG UUG GGU GUU CCA UUU CAU UUA GGA ACC      532
Arg Thr Leu Leu Met Asn Glu Leu Gly Val Pro Phe His Leu Gly Thr
            160                 165                 170

AAA CAA GUG UGU GCA GCA UGG UCC AGC UCA AGU UGU CAC GAU GGA AAA      580
Lys Gln Val Cys Ala Ala Trp Ser Ser Ser Ser Cys His Asp Gly Lys
            175                 180                 185

GCA UGG UUG CAU GUU UGU GUC ACA GGG GAU GAU AGA AAU GCA ACU GCU      628
Ala Trp Leu His Val Cys Val Thr Gly Asp Asp Arg Asn Ala Thr Ala
        190                 195                 200

AGC UUC AUU UAU GAC GGG AAG CUU GUG GAC AGU AUU GGU UCA UGG UCU      676
Ser Phe Ile Tyr Asp Gly Lys Leu Val Asp Ser Ile Gly Ser Trp Ser
    205                 210                 215

CAA AAU GUC CUC AGG ACC CAG GAG UCG GAA UGC GUC UGU AUC AAU GGG      724
Gln Asn Val Leu Arg Thr Gln Glu Ser Glu Cys Val Cys Ile Asn Gly
220                 225                 230                 235

ACU UGC ACA GUA GUA AUG ACU GAU GGA AGU GCA UCA GGA AGA GCU GAU      772
Thr Cys Thr Val Val Met Thr Asp Gly Ser Ala Ser Gly Arg Ala Asp
            240                 245                 250

ACU AGA AUA CUA UUC AUU AAA GAG GGG AAA AUU GUC CAU AUU GGC CCA      820
Thr Arg Ile Leu Phe Ile Lys Glu Gly Lys Ile Val His Ile Gly Pro
        255                 260                 265

UUG UCA GGA AGU GCU CAG CAU GUA GAG GAG UGU UCU UGU UAC CCU CGA      868
Leu Ser Gly Ser Ala Gln His Val Glu Glu Cys Ser Cys Tyr Pro Arg
        270                 275                 280

UAU CCU GAC GUC AGA UGU AUC UGC AGA GAC AAC UGG AAA GGC UCU AAU      916
Tyr Pro Asp Val Arg Cys Ile Cys Arg Asp Asn Trp Lys Gly Ser Asn
    285                 290                 295

AGG CCC GUU AUA GAC AUA AAU AUG GAA GAU UAU AGC AUU GAU UCC AGU      964
Arg Pro Val Ile Asp Ile Asn Met Glu Asp Tyr Ser Ile Asp Ser Ser
300                 305                 310                 315

UAU GUG UGC UCA GGG CUU GUU GGC GAC ACA CCC AGG AAC GAC GAC AGC     1012
Tyr Val Cys Ser Gly Leu Val Gly Asp Thr Pro Arg Asn Asp Asp Ser
        320                 325                 330

UCU AGC AAU AGC AAU UGC AGG GAU CCU AAC AAU GAG AGA GGG AAU CCA     1060
Ser Ser Asn Ser Asn Cys Arg Asp Pro Asn Asn Glu Arg Gly Asn Pro
            335                 340                 345

GGA GUG AAA GGC UGG GCC UUU GAC AAU GGA GAU GAU GUA UGG AUG GGA     1108
Gly Val Lys Gly Trp Ala Phe Asp Asn Gly Asp Asp Val Trp Met Gly
        350                 355                 360

AGA ACA AUC AGC AAA GAU UUA CGC UCA GGU UAU GAA ACU UUC AAA GUC     1156
Arg Thr Ile Ser Lys Asp Leu Arg Ser Gly Tyr Glu Thr Phe Lys Val
    365                 370                 375

AUU GGU GGU UGG UCC ACA CCU AAU UCC AAA UCG CAG GUC AAU AGA CAG     1204
Ile Gly Gly Trp Ser Thr Pro Asn Ser Lys Ser Gln Val Asn Arg Gln
380                 385                 390                 395

GUC AUA GUU GAC AAC AAU AAU UGG UCU GGU UAC UCU GGU AUU UUC UCU     1252
Val Ile Val Asp Asn Asn Asn Trp Ser Gly Tyr Ser Gly Ile Phe Ser
            400                 405                 410
```

```
GUU GAG GGC AAA AGC UGC AUC AAU AGG UGC UUU UAU GUG GAG UUG AUA      1300
Val Glu Gly Lys Ser Cys Ile Asn Arg Cys Phe Tyr Val Glu Leu Ile
            415                 420                 425

AGG GGA AGG CCA CAG GAG ACU AGA GUA UGG UGG ACC UCA AAC AGU AUU      1348
Arg Gly Arg Pro Gln Glu Thr Arg Val Trp Trp Thr Ser Asn Ser Ile
        430                 435                 440

GUU GUA UUU UGU GGC ACU UCA GGU ACU UAU GGA ACA GGC UCA UGG CCU      1396
Val Val Phe Cys Gly Thr Ser Gly Thr Tyr Gly Thr Gly Ser Trp Pro
    445                 450                 455

GAU GGG GCG AAC AUC AAU UUC AUG CCU AUA UAACGUUUCG CAAUUUUAGA       1446
Asp Gly Ala Asn Ile Asn Phe Met Pro Ile
460                 465

AAAAAACUCC UUGUUUCUAC U                                              1467
```

(2) INFORMATION FOR SEQ ID NO: 38:

(i) SEQUENCE CHARACTERISTICS:
(A) LENGTH: 469 amino acids
(B) TYPE: amino acid
(D) TOPOLOGY: linear (ii) MOLECULE TYPE: protein (xi) SEQUENCE DESCRIPTION: SEQ ID NO: 38:

```
Met Asn Pro Asn Gln Lys Thr Ile Thr Ile Gly Ser Val Ser Leu Thr
  1               5                  10                  15

Ile Ala Thr Val Cys Phe Leu Met Gln Ile Ala Ile Leu Ala Thr Thr
             20                  25                  30

Val Thr Leu His Leu Lys Gln His Glu Cys Asp Ser Pro Ala Ser Asn
         35                  40                  45

Gln Val Met Pro Cys Glu Pro Ile Ile Ile Glu Arg Asn Ile Thr Glu
     50                  55                  60

Ile Val Tyr Leu Asn Asn Thr Thr Ile Glu Lys Glu Ile Cys Pro Glu
 65                  70                  75                  80

Val Val Gly Tyr Arg Asn Trp Ser Lys Pro Gln Cys Gln Ile Thr Gly
                 85                  90                  95

Phe Ala Pro Phe Ser Lys Asp Asn Ser Ile Arg Leu Ser Ala Gly Gly
            100                 105                 110

Asp Ile Trp Val Thr Arg Glu Pro Tyr Val Ser Cys Asp Pro Gly Lys
        115                 120                 125

Cys Tyr Gln Phe Ala Leu Gly Gln Gly Thr Thr Leu Asp Asn Lys His
    130                 135                 140

Ser Asn Gly Thr Ile His Asp Arg Ile Pro His Arg Thr Leu Leu Met
145                 150                 155                 160

Asn Glu Leu Gly Val Pro Phe His Leu Gly Thr Lys Gln Val Cys Ala
                165                 170                 175

Ala Trp Ser Ser Ser Ser Cys His Asp Gly Lys Ala Trp Leu His Val
            180                 185                 190

Cys Val Thr Gly Asp Asp Arg Asn Ala Thr Ala Ser Phe Ile Tyr Asp
        195                 200                 205

Gly Lys Leu Val Asp Ser Ile Gly Ser Trp Ser Gln Asn Val Leu Arg
    210                 215                 220

Thr Gln Glu Ser Glu Cys Val Cys Ile Asn Gly Thr Cys Thr Val Val
225                 230                 235                 240

Met Thr Asp Gly Ser Ala Ser Gly Arg Ala Asp Thr Arg Ile Leu Phe
                245                 250                 255

Ile Lys Glu Gly Lys Ile Val His Ile Gly Pro Leu Ser Gly Ser Ala
            260                 265                 270
```

-continued

```
Gln His Val Glu Glu Cys Ser Cys Tyr Pro Arg Tyr Pro Asp Val Arg
        275                 280                 285

Cys Ile Cys Arg Asp Asn Trp Lys Gly Ser Asn Arg Pro Val Ile Asp
    290                 295                 300

Ile Asn Met Glu Asp Tyr Ser Ile Asp Ser Ser Tyr Val Cys Ser Gly
305                 310                 315                 320

Leu Val Gly Asp Thr Pro Arg Asn Asp Asp Ser Ser Ser Asn Ser Asn
                325                 330                 335

Cys Arg Asp Pro Asn Asn Glu Arg Gly Asn Pro Gly Val Lys Gly Trp
            340                 345                 350

Ala Phe Asp Asn Gly Asp Asp Val Trp Met Gly Arg Thr Ile Ser Lys
        355                 360                 365

Asp Leu Arg Ser Gly Tyr Glu Thr Phe Lys Val Ile Gly Gly Trp Ser
    370                 375                 380

Thr Pro Asn Ser Lys Ser Gln Val Asn Arg Gln Val Ile Val Asp Asn
385                 390                 395                 400

Asn Asn Trp Ser Gly Tyr Ser Gly Ile Phe Ser Val Glu Gly Lys Ser
                405                 410                 415

Cys Ile Asn Arg Cys Phe Tyr Val Glu Leu Ile Arg Gly Arg Pro Gln
            420                 425                 430

Glu Thr Arg Val Trp Trp Thr Ser Asn Ser Ile Val Val Phe Cys Gly
        435                 440                 445

Thr Ser Gly Thr Tyr Gly Thr Gly Ser Trp Pro Asp Gly Ala Asn Ile
    450                 455                 460

Asn Phe Met Pro Ile
465
```

(2) INFORMATION FOR SEQ ID NO: 39:

(i) SEQUENCE CHARACTERISTICS:
(A) LENGTH: 1566 base pairs
(B) TYPE: nucleic acid
(C) STRANDEDNESS: single
(D) TOPOLOGY: linear (ii) MOLECULE TYPE: RNA (genomic)

(vi) ORIGINAL SOURCE:
(A) ORGANISM: Influenza virus
(B) STRAIN: wild type A/Ann Arbor/6/60 (H2N2) Egg Passage 2(3)

(vii) IMMEDIATE SOURCE:
(B) CLONE: NP (ix) FEATURE:
(A) NAME/KEY: mutation
(B) LOCATION: replace(113, "a")
(D) OTHER INFORMATION: /note= "c in ca "master" strain; a in wt2(3); c in 1988 reported wild type E28-32 strain (manuscript) but a in 1988 reported wild type E28-32 strain
/citation= ([1][2])

(ix) FEATURE:
(A) NAME/KEY: conflict
(B) LOCATION: replace(146, "g")
(D) OTHER INFORMATION: /note= "g in ca "master" strain and in wt2(3); a in 1988 reported wild type E28-32 strain"
/citation= ([1][2])

(ix) FEATURE:
(A) NAME/KEY: conflict
(B) LOCATION: replace(627, "c")
(D) OTHER INFORMATION: /note= "c in ca "master" strain and in wt2(3); a in 1988 reported wild type E28-32 strain"
/citation= ([1][2])

-continued

```
(ix) FEATURE:
      (A) NAME/KEY: conflict
      (B) LOCATION: replace(909, "g")
      (D) OTHER INFORMATION: /note= "g in ca "master" strain and in
           wt2(3); c in 1988 reported wild type E28-32 strain"
           /citation= ([1][2])

(ix) FEATURE:
      (A) NAME/KEY: conflict
      (B) LOCATION: replace(1550, "a")
      (D) OTHER INFORMATION: /note= "a in ca "master" strain and in
           wt2(3); deletion in 1988 reported wild type E28-32
           strain"
           /citation= ([1][2])

(ix) FEATURE:
      (A) NAME/KEY: CDS
      (B) LOCATION: 46..1539
      (D) OTHER INFORMATION: /product= "Nucleoprotein"
           /gene= "NP"
           /note= "nucleoprotein"
           /citation= ([1][2])

 (x) PUBLICATION INFORMATION:
      (A) AUTHORS: Herlocher, M L
           Maassab, H F
           Webster, R W
      (B) TITLE: Molecular and biological changes in the cold
           adapted master strain A/AA/6/60 (H2N2) influenza
           virus
      (C) JOURNAL: Proceedings of the National Academy of Sciences
           of the USA
      (G) DATE: 1993
      (K) RELEVANT RESIDUES IN SEQ ID NO:39: FROM 1 TO 1566

 (x) PUBLICATION INFORMATION:
      (A) AUTHORS: Cox, N J
           Kitame, F
           Kendal, A P
           Maassab, H F
           Naeve, C
      (B) TITLE: Identification of sequence changes in the
           cold-adapted live attenuated influenza vaccine
           strain, A/Ann Arbor/6/60 (H2N2)
      (C) JOURNAL: Virology
      (D) VOLUME: 167
      (F) PAGES: 554-567
      (G) DATE: 1988
      (K) RELEVANT RESIDUES IN SEQ ID NO:39: FROM 1 TO 1566

(xi) SEQUENCE DESCRIPTION: SEQ ID NO: 39:

AGCAAAAGCA GGGUAGAUAA UCACUCACUG AGUGACAUCA AAAUC AUG GCG UCC         54
                                                  Met Ala Ser
                                                    1

CAA GGC ACC AAA CGG UCU UAU GAA CAG AUG GAA ACU GAU GGG GAA CGC      102
Gln Gly Thr Lys Arg Ser Tyr Glu Gln Met Glu Thr Asp Gly Glu Arg
      5                  10                  15

CAG AAU GCA AAU GAA AUC AGA GCA UCC GUC GGG AAG AUG AUU GGU GGA      150
Gln Asn Ala Asn Glu Ile Arg Ala Ser Val Gly Lys Met Ile Gly Gly
 20                  25                  30                  35

AUU GGA CGA UUC UAC AUC CAA AUG UGC ACC GAA CUU AAA CUC AGU GAU      198
Ile Gly Arg Phe Tyr Ile Gln Met Cys Thr Glu Leu Lys Leu Ser Asp
                 40                  45                  50

UAU GAG GGG CGG CUG AUC CAG AAC AGC UUA ACA AUA GAG AGA AUG GUG      246
Tyr Glu Gly Arg Leu Ile Gln Asn Ser Leu Thr Ile Glu Arg Met Val
             55                  60                  65

CUC UCU GCU UUU GAC GAG AGG AGG AAU AAA UAU CUG GAA GAA CAU CCC      294
Leu Ser Ala Phe Asp Glu Arg Arg Asn Lys Tyr Leu Glu Glu His Pro
         70                  75                  80

AGC GCG GGG AAG GAU CCU AAG AAA ACU GGA GGA CCC AUA UAC AAG AGA      342
Ser Ala Gly Lys Asp Pro Lys Lys Thr Gly Gly Pro Ile Tyr Lys Arg
     85                  90                  95
```

```
GUA GAU GGA AAG UGG AUG AGG GAA CUC GUC CUU UAU GAC AAA GAA GAA        390
Val Asp Gly Lys Trp Met Arg Glu Leu Val Leu Tyr Asp Lys Glu Glu
100                 105                 110                 115

AUA AGG CGA AUC UGG CGC CAA GCU AAU AAU GGU GAU GAU GCA ACA GCU        438
Ile Arg Arg Ile Trp Arg Gln Ala Asn Asn Gly Asp Asp Ala Thr Ala
                120                 125                 130

GGU CUG ACU CAC AUG AUG AUC UGG CAU UCC AAU UUG AAU GAU ACA ACA        486
Gly Leu Thr His Met Met Ile Trp His Ser Asn Leu Asn Asp Thr Thr
            135                 140                 145

UAC CAG AGG ACA AGA GCU CUU GUU CGC ACC GGA AUG GAU CCC AGG AUG        534
Tyr Gln Arg Thr Arg Ala Leu Val Arg Thr Gly Met Asp Pro Arg Met
        150                 155                 160

UGC UCU UUG AUG CAG GGU UCG ACU CUC CCU AGG AGG UCU GGA GCC GCA        582
Cys Ser Leu Met Gln Gly Ser Thr Leu Pro Arg Arg Ser Gly Ala Ala
    165                 170                 175

GGC GCU GCA GUC AAA GGA GUU GGG ACA AUG GUG AUG GAG UUG AUC AGG        630
Gly Ala Ala Val Lys Gly Val Gly Thr Met Val Met Glu Leu Ile Arg
180                 185                 190                 195

AUG AUC AAA CGU GGG AUC AAU GAU CGG AAC UUC UGG AGA GGU GAG AAU        678
Met Ile Lys Arg Gly Ile Asn Asp Arg Asn Phe Trp Arg Gly Glu Asn
                200                 205                 210

GGG CGG AAA ACA AGG AAU GCU UAU GAG AGA AUG UGC AAC AUU CUC AAA        726
Gly Arg Lys Thr Arg Asn Ala Tyr Glu Arg Met Cys Asn Ile Leu Lys
            215                 220                 225

GGA AAA UUU CAA ACA GCU GCA CAA AGA GCA AUG AUG GAU CAA GUG AGA        774
Gly Lys Phe Gln Thr Ala Ala Gln Arg Ala Met Met Asp Gln Val Arg
        230                 235                 240

GAA AGC CGG AAC CCA GGA AAU GCU GAG AUC GAA GAU CUC AUC UUU CUG        822
Glu Ser Arg Asn Pro Gly Asn Ala Glu Ile Glu Asp Leu Ile Phe Leu
    245                 250                 255

GCA CGG UCU GCA CUC AUA UUG AGA GGG UCA GUU GCU CAC AAA UCU UGU        870
Ala Arg Ser Ala Leu Ile Leu Arg Gly Ser Val Ala His Lys Ser Cys
260                 265                 270                 275

CUG CCU GCC UGU GUG UAU GGA CCU GCC GUA GCC AGU GGG UAC GAC UUC        918
Leu Pro Ala Cys Val Tyr Gly Pro Ala Val Ala Ser Gly Tyr Asp Phe
                280                 285                 290

GAA AAA GAG GGA UAC UCU UUA GUA GGG AUA GAC CCU UUC AAA CUG CUU        966
Glu Lys Glu Gly Tyr Ser Leu Val Gly Ile Asp Pro Phe Lys Leu Leu
            295                 300                 305

CAA AAC AGC CAA GUA UAC AGC CUA AUC AGA CCG AAU GAG AAU CCA GCA       1014
Gln Asn Ser Gln Val Tyr Ser Leu Ile Arg Pro Asn Glu Asn Pro Ala
        310                 315                 320

CAC AAG AGU CAG CUG GUG UGG AUG GCA UGC AAU UCU GCU GCA UUU GAA       1062
His Lys Ser Gln Leu Val Trp Met Ala Cys Asn Ser Ala Ala Phe Glu
    325                 330                 335

GAU CUA AGA GUA UCA AGC UUC AUC AGA GGG ACC AAA GUA AUC CCA AGG       1110
Asp Leu Arg Val Ser Ser Phe Ile Arg Gly Thr Lys Val Ile Pro Arg
340                 345                 350                 355

GGG AAA CUU UCC ACU AGA GGA GUA CAA AUU GCU UCA AAU GAA AAC AUG       1158
Gly Lys Leu Ser Thr Arg Gly Val Gln Ile Ala Ser Asn Glu Asn Met
                360                 365                 370

GAU ACU AUG GGA UCA AGU ACU CUU GAA CUG AGA AGC AGG UAC UGG GCC       1206
Asp Thr Met Gly Ser Ser Thr Leu Glu Leu Arg Ser Arg Tyr Trp Ala
            375                 380                 385

AUA AGG ACC AGA AGU GGA GGA AAC ACU AAU CAA CAG AGG GCC UCU GCA       1254
Ile Arg Thr Arg Ser Gly Gly Asn Thr Asn Gln Gln Arg Ala Ser Ala
        390                 395                 400

GGU CAA AUC AGU GUA CAA CCU ACG UUU UCU GUG CAA AGA AAC CUC CCA       1302
Gly Gln Ile Ser Val Gln Pro Thr Phe Ser Val Gln Arg Asn Leu Pro
    405                 410                 415
```

```
UUU GAC AAA CCA ACC AUC AUG GCA GCA UUC ACU GGG AAU GCA GAG GGA      1350
Phe Asp Lys Pro Thr Ile Met Ala Ala Phe Thr Gly Asn Ala Glu Gly
420                 425                 430                 435

AGA ACA UCA GAC AUG AGG GCA GAA AUC AUA AGG AUG AUG GAA GGU GCA      1398
Arg Thr Ser Asp Met Arg Ala Glu Ile Ile Arg Met Met Glu Gly Ala
                440                 445                 450

AAA CCA GAA GAA GUG UCC UUC CAG GGG CGG GGA GUC UUC GAG CUC UCG      1446
Lys Pro Glu Glu Val Ser Phe Gln Gly Arg Gly Val Phe Glu Leu Ser
            455                 460                 465

GAC GAA AAG GCA ACG AAC CCG AUC GUG CCC UCU UUU GAC AUG AGU AAU      1494
Asp Glu Lys Ala Thr Asn Pro Ile Val Pro Ser Phe Asp Met Ser Asn
        470                 475                 480

GAA GGA UCU UAU UUC UUC GGA GAC AAU GCA GAG GAG UAC GAC AAU          1539
Glu Gly Ser Tyr Phe Phe Gly Asp Asn Ala Glu Glu Tyr Asp Asn
    485                 490                 495

UAAGGAAAAA AUACCCUUGU UUCUACU                                        1566
```

(2) INFORMATION FOR SEQ ID NO: 40:

(i) SEQUENCE CHARACTERISTICS:
(A) LENGTH: 498 amino acids
(B) TYPE: amino acid
(D) TOPOLOGY: linear (ii) MOLECULE TYPE: protein (xi) SEQUENCE DESCRIPTION: SEQ ID NO: 40:

```
Met Ala Ser Gln Gly Thr Lys Arg Ser Tyr Glu Gln Met Glu Thr Asp
  1               5                  10                  15

Gly Glu Arg Gln Asn Ala Asn Glu Ile Arg Ala Ser Val Gly Lys Met
            20                  25                  30

Ile Gly Gly Ile Gly Arg Phe Tyr Ile Gln Met Cys Thr Glu Leu Lys
        35                  40                  45

Leu Ser Asp Tyr Glu Gly Arg Leu Ile Gln Asn Ser Leu Thr Ile Glu
     50                  55                  60

Arg Met Val Leu Ser Ala Phe Asp Glu Arg Arg Asn Lys Tyr Leu Glu
 65                  70                  75                  80

Glu His Pro Ser Ala Gly Lys Asp Pro Lys Lys Thr Gly Gly Pro Ile
                85                  90                  95

Tyr Lys Arg Val Asp Gly Lys Trp Met Arg Glu Leu Val Leu Tyr Asp
            100                 105                 110

Lys Glu Glu Ile Arg Arg Ile Trp Arg Gln Ala Asn Asn Gly Asp Asp
        115                 120                 125

Ala Thr Ala Gly Leu Thr His Met Met Ile Trp His Ser Asn Leu Asn
    130                 135                 140

Asp Thr Thr Tyr Gln Arg Thr Arg Ala Leu Val Arg Thr Gly Met Asp
145                 150                 155                 160

Pro Arg Met Cys Ser Leu Met Gln Gly Ser Thr Leu Pro Arg Arg Ser
                165                 170                 175

Gly Ala Ala Gly Ala Ala Val Lys Gly Val Gly Thr Met Val Met Glu
            180                 185                 190

Leu Ile Arg Met Ile Lys Arg Gly Ile Asn Asp Arg Asn Phe Trp Arg
        195                 200                 205

Gly Glu Asn Gly Arg Lys Thr Arg Asn Ala Tyr Glu Arg Met Cys Asn
    210                 215                 220

Ile Leu Lys Gly Lys Phe Gln Thr Ala Ala Gln Arg Ala Met Met Asp
225                 230                 235                 240
```

-continued

```
Gln Val Arg Glu Ser Arg Asn Pro Gly Asn Ala Glu Ile Glu Asp Leu
                245                 250                 255

Ile Phe Leu Ala Arg Ser Ala Leu Ile Leu Arg Gly Ser Val Ala His
            260                 265                 270

Lys Ser Cys Leu Pro Ala Cys Val Tyr Gly Pro Ala Val Ala Ser Gly
        275                 280                 285

Tyr Asp Phe Glu Lys Glu Gly Tyr Ser Leu Val Gly Ile Asp Pro Phe
    290                 295                 300

Lys Leu Leu Gln Asn Ser Gln Val Tyr Ser Leu Ile Arg Pro Asn Glu
305                 310                 315                 320

Asn Pro Ala His Lys Ser Gln Leu Val Trp Met Ala Cys Asn Ser Ala
                325                 330                 335

Ala Phe Glu Asp Leu Arg Val Ser Ser Phe Ile Arg Gly Thr Lys Val
            340                 345                 350

Ile Pro Arg Gly Lys Leu Ser Thr Arg Gly Val Gln Ile Ala Ser Asn
        355                 360                 365

Glu Asn Met Asp Thr Met Gly Ser Ser Thr Leu Glu Leu Arg Ser Arg
    370                 375                 380

Tyr Trp Ala Ile Arg Thr Arg Ser Gly Gly Asn Thr Asn Gln Gln Arg
385                 390                 395                 400

Ala Ser Ala Gly Gln Ile Ser Val Gln Pro Thr Phe Ser Val Gln Arg
                405                 410                 415

Asn Leu Pro Phe Asp Lys Pro Thr Ile Met Ala Ala Phe Thr Gly Asn
            420                 425                 430

Ala Glu Gly Arg Thr Ser Asp Met Arg Ala Glu Ile Ile Arg Met Met
        435                 440                 445

Glu Gly Ala Lys Pro Glu Glu Val Ser Phe Gln Gly Arg Gly Val Phe
    450                 455                 460

Glu Leu Ser Asp Glu Lys Ala Thr Asn Pro Ile Val Pro Ser Phe Asp
465                 470                 475                 480

Met Ser Asn Glu Gly Ser Tyr Phe Phe Gly Asp Asn Ala Glu Glu Tyr
                485                 490                 495

Asp Asn
```